(12) United States Patent
Chen et al.

(10) Patent No.: US 6,673,982 B1
(45) Date of Patent: Jan. 6, 2004

(54) ABSORBENT ARTICLE WITH CENTER FILL PERFORMANCE

(75) Inventors: Fung-jou Chen, Appleton, WI (US);
Julie M. Bednarz, Neenah, WI (US);
Jeffrey D. Lindsay, Appleton, WI (US);
Joseph DiPalma, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/165,875

(22) Filed: Oct. 2, 1998

(51) Int. Cl.[7] ................................................ A61F 13/15
(52) U.S. Cl. .................................. 604/378; 604/385.101
(58) Field of Search ................................. 604/358, 367, 604/378–383, 385.01, 385.101

(56) References Cited

U.S. PATENT DOCUMENTS 1,843,037 A    1/1932    Mathey (List continued on next page.)

FOREIGN PATENT DOCUMENTS

| CA | 803531 | 1/1969 | |
|---|---|---|---|
| EP | 0 360 285 A3 | 3/1990 | |
| EP | 0 391 727 A3 | 10/1990 | |
| EP | 0 441 064 A1 | 8/1991 | |
| EP | 0 483 592 A1 | 5/1992 | |
| EP | 0 549 784 B1 | 7/1993 | ........... A61F/13/15 |
| EP | 0 804 913 A1 | 11/1997 | ........... A61F/13/15 |
| GB | 2 233 235 A | 1/1991 | |
| WO | WO 83/03051 A1 | 9/1983 | |
| WO | WO 96/38232 A1 | 12/1996 | ........... B05D/3/02 |
| WO | WO 97/34558 A1 | 9/1997 | ........... A61F/13/15 |
| WO | WO 97/34559 A1 | 9/1997 | ........... A61F/13/46 |
| WO | WO 98/00081 A1 | 1/1998 | ........... A61F/13/15 |
| WO | WO 98/00082 A1 | 1/1998 | ........... A61F/13/15 |
| WO | WO 98/24389 A1 | 6/1998 | ........... A61F/13/15 |
| WO | WO 98/31318 A1 | 7/1998 | |

OTHER PUBLICATIONS

American Society for Testing Materials (ASTM) Designation: D 4032–82, "Standard Test Method for Stiffness of Fabric by the Circular Bend Procedure," pp. 702–706, published Aug. 1982.

American Society for Testing Materials (ASTM) Designation: D 3574–91, "Standard Test Methods for Flexible Cellular Materials—Slab, Bonded, and Molded Urethane Foams," Procedures C and H, published Mar. 1992.

Chatterjee, P.K., Editor, Absorbency, published by Elsevier, 1985, pp. 42–44.

(List continued on next page.)

*Primary Examiner*—Weilun Lo
*Assistant Examiner*—Jamisue A. Webb
(74) *Attorney, Agent, or Firm*—Pauley Petersen & Erickson

(57) ABSTRACT

An absorbent article comprising a central absorbent member and a lateral wicking barrier for inhibition of wicking from the central regions of the article to an outlying outer absorbent member. The wicking barrier has a vertical component for prevention of radial wicking in the plane of the article and thus promotes center filling of the article with fluid and reduces the likelihood of leaks from the sides of the article. The wicking barrier can also have a horizontal component to prevent leakage, redirect fluid flow, and improve fit and performance of the article. In one embodiment, the central absorbent member is a concentric absorbent structure having alternating rings of barrier material and absorbent material, including a spiral wound composite formed from a layer of barrier material wound with a layer of absorbent material and then sliced to provide a thin absorbent layer having high permeability in the thickness direction but low permeability in the plane due to the barrier material.

57 Claims, 26 Drawing Sheets

U.S. PATENT DOCUMENTS

| | | | |
|---|---|---|---|
| 2,331,355 A | 10/1943 | Strongson | |
| 2,952,260 A | 9/1960 | Burgeni | 128/290 |
| 3,029,817 A | 4/1962 | Harwood et al. | 128/290 |
| 3,036,573 A | 5/1962 | Voigtman et al. | 128/290 |
| 3,211,147 A | 10/1965 | Pherson et al. | 128/284 |
| 3,230,955 A | 1/1966 | Joa et al. | 128/290 |
| 3,343,543 A | 9/1967 | Glassman | 128/290 |
| 3,468,311 A | 9/1969 | Gallagher | 128/296 |
| 3,556,932 A | 1/1971 | Coscia et al. | 162/166 |
| 3,556,933 A | 1/1971 | Williams et al. | 162/167 |
| 3,592,194 A | 7/1971 | Duncan | 128/287 |
| 3,595,235 A | 7/1971 | Jespersen | 128/284 |
| 3,612,054 A | 10/1971 | Matsuda et al. | 128/287 |
| 3,700,623 A | 10/1972 | Keim | 260/80.3 R |
| 3,772,076 A | 11/1973 | Keim | 117/155 R |
| 3,885,158 A | 5/1975 | Flutie et al. | 250/440 |
| 3,886,941 A | 6/1975 | Duane et al. | 128/287 |
| 3,889,679 A | 6/1975 | Taylor | 128/287 |
| 3,899,388 A | 8/1975 | Petrovich et al. | 162/164 |
| 3,903,890 A | 9/1975 | Mesek et al. | 128/287 |
| 3,954,107 A | 5/1976 | Chesky et al. | 128/290 R |
| 4,015,604 A | 4/1977 | Csillag | 128/287 |
| 4,029,101 A | 6/1977 | Chesky et al. | 128/290 R |
| 4,059,114 A | 11/1977 | Richards | 128/287 |
| 4,062,362 A | 12/1977 | Schaar | 128/287 |
| 4,069,822 A | 1/1978 | Buell | 128/294 |
| 4,100,324 A | 7/1978 | Anderson et al. | 428/288 |
| 4,129,135 A | 12/1978 | Petrovich et al. | 260/823 |
| 4,147,586 A | 4/1979 | Petrovich et al. | 162/135 |
| 4,200,103 A | 4/1980 | Black et al. | 128/290 W |
| 4,222,921 A | 9/1980 | Van Eenam | 260/29.6 H |
| 4,282,874 A * | 8/1981 | Mesek | 128/287 |
| 4,324,246 A | 4/1982 | Mullane et al. | 128/287 |
| 4,340,058 A | 7/1982 | Pierce et al. | 128/287 |
| 4,342,314 A | 8/1982 | Radel et al. | 128/287 |
| 4,397,644 A | 8/1983 | Matthews et al. | 604/378 |
| 4,405,326 A | 9/1983 | Lenaghan | 604/385 |
| 4,410,324 A | 10/1983 | Sabee | 604/368 |
| 4,463,045 A | 7/1984 | Ahr et al. | 428/131 |
| 4,476,180 A | 10/1984 | Wnuk | 428/220 |
| 4,490,147 A | 12/1984 | Pierce et al. | 604/378 |
| 4,522,967 A | 6/1985 | Sheldon et al. | 524/377 |
| 4,524,474 A | 6/1985 | Svensson | 5/484 |
| 4,556,146 A | 12/1985 | Swanson et al. | 206/440 |
| 4,568,341 A | 2/1986 | Mitchell et al. | 604/368 |
| 4,573,986 A | 3/1986 | Minetola et al. | 604/366 |
| 4,578,070 A | 3/1986 | Holtman | 604/378 |
| 4,578,071 A | 3/1986 | Buell | 604/379 |
| 4,589,876 A | 5/1986 | Van Tilburg | 604/385.1 |
| 4,627,848 A | 12/1986 | Lassen et al. | 604/370 |
| 4,636,209 A | 1/1987 | Lassen | 604/378 |
| 4,643,726 A | 2/1987 | Gegelys | 604/368 |
| 4,657,538 A | 4/1987 | Becker et al. | 604/381 |
| 4,675,394 A | 6/1987 | Solarek et al. | 536/43 |
| 4,676,784 A | 6/1987 | Erdman et al. | 604/368 |
| 4,676,786 A | 6/1987 | Nishino | 604/378 |
| 4,678,464 A | 7/1987 | Holtman | 604/385 R |
| 4,681,793 A | 7/1987 | Linman et al. | 428/138 |
| 4,687,478 A | 8/1987 | Van Tilburg | 604/387 |
| 4,723,953 A | 2/1988 | Rosenbaum et al. | 604/369 |
| 4,753,644 A | 6/1988 | Cottenden et al. | 604/378 |
| 4,758,240 A | 7/1988 | Glassman | |
| 4,773,905 A | 9/1988 | Molee et al. | 604/378 |
| 4,781,711 A | 11/1988 | Houghton et al. | 604/378 |
| 4,787,896 A | 11/1988 | Houghton et al. | 604/385.1 |
| 4,795,452 A | 1/1989 | Blaney et al. | 604/385.1 |
| 4,879,170 A | 11/1989 | Radwanski et al. | 428/233 |
| 4,936,839 A | 6/1990 | Molee et al. | 604/378 |
| 4,950,264 A | 8/1990 | Osborn, III | 604/385.1 |
| 4,963,139 A | 10/1990 | Dabroski | 604/378 |
| 4,973,325 A | 11/1990 | Sherrod et al. | 604/368 |
| 4,981,557 A | 1/1991 | Bjorkquist | 162/168.2 |
| 4,988,344 A | 1/1991 | Reising et al. | 604/368 |
| 5,008,344 A | 4/1991 | Bjorkquist | 525/328.2 |
| 5,009,653 A | 4/1991 | Osborn, III | 604/385.1 |
| 5,048,589 A | 9/1991 | Cook et al. | 162/109 |
| 5,085,736 A | 2/1992 | Bjorkquist | 162/168.2 |
| 5,104,396 A | 4/1992 | Oatley et al. | 604/379 |
| 5,147,343 A | 9/1992 | Kellenberger | 604/368 |
| 5,151,091 A | 9/1992 | Glaug et al. | 604/385.1 |
| 5,167,654 A | 12/1992 | Yang | 604/385.2 |
| 5,188,625 A | 2/1993 | Van Iten et al. | 604/383 |
| 5,242,435 A | 9/1993 | Murji et al. | 604/374 |
| 5,267,992 A | 12/1993 | Van Tilburg | 604/387 |
| 5,275,591 A | 1/1994 | Mavinkurve | 604/387 |
| 5,281,208 A | 1/1994 | Thompson et al. | 604/378 |
| 5,300,358 A | 4/1994 | Evers | 428/286 |
| 5,342,337 A | 8/1994 | Runeman et al. | |
| 5,348,547 A | 9/1994 | Payne et al. | 604/378 |
| 5,350,624 A | 9/1994 | Georger et al. | 428/219 |
| 5,356,405 A | 10/1994 | Thompson et al. | 604/384 |
| 5,360,422 A | 11/1994 | Brownlee et al. | 604/385.2 |
| 5,399,175 A | 3/1995 | Glaug et al. | 604/385.1 |
| 5,399,412 A | 3/1995 | Sudall et al. | 428/153 |
| 5,401,267 A | 3/1995 | Couture-orschner et al. | 604/384 |
| 5,405,342 A | 4/1995 | Roessler et al. | 604/364 |
| 5,423,786 A | 6/1995 | Fung et al. | 604/367 |
| 5,429,629 A | 7/1995 | Latimer et al. | 604/378 |
| 5,429,686 A | 7/1995 | Chiu et al. | 139/383 A |
| 5,460,623 A | 10/1995 | Emenaker et al. | 604/368 |
| H1511 H | 12/1995 | Chappell et al. | 604/383 |
| 5,490,846 A | 2/1996 | Ellis et al. | 604/366 |
| 5,509,913 A | 4/1996 | Yeo | 604/364 |
| 5,514,104 A | 5/1996 | Cole et al. | 604/366 |
| 5,522,809 A | 6/1996 | Larsonneur | 604/361 |
| 5,527,300 A | 6/1996 | Sauer | 604/378 |
| 5,533,991 A | 7/1996 | Kirby et al. | 604/383 |
| H1585 H | 8/1996 | Ahr | 604/378 |
| 5,545,156 A | 8/1996 | DiPalma et al. | 604/385.1 |
| 5,562,645 A | 10/1996 | Tanzer et al. | 604/367 |
| 5,562,650 A | 10/1996 | Everett et al. | 604/378 |
| H1614 H | 11/1996 | Mayer et al. | 604/385.1 |
| 5,575,786 A | 11/1996 | Osborn, III | 604/387 |
| 5,578,025 A | 11/1996 | May | |
| 5,591,148 A | 1/1997 | McFall et al. | 604/378 |
| 5,591,150 A | 1/1997 | Olsen et al. | 604/385.1 |
| 5,599,337 A | 2/1997 | Mccoy | 604/385.1 |
| 5,603,707 A | 2/1997 | Trombetta et al. | 604/383 |
| 5,607,551 A | 3/1997 | Farrington, Jr. et al. | 162/109 |
| 5,611,790 A | 3/1997 | Osborn, III et al. | 604/391 |
| 5,624,423 A | 4/1997 | Anjur et al. | 604/385.1 |
| 5,643,238 A | 7/1997 | Baker | 604/368 |
| 5,643,653 A | 7/1997 | Griesbach, III et al. | 428/120 |
| 5,647,863 A | 7/1997 | Hammons et al. | 604/378 |
| 5,649,916 A | 7/1997 | DiPalma et al. | 604/378 |
| 5,662,633 A | 9/1997 | Doak et al. | 604/378 |
| 5,672,248 A | 9/1997 | Wendt et al. | 162/109 |
| 5,681,303 A | 10/1997 | Mills et al. | 604/385.2 |
| 5,688,259 A | 11/1997 | Osborn, III et al. | 604/385.1 |
| 5,692,939 A | 12/1997 | DesMarais | 442/373 |
| 5,695,487 A | 12/1997 | Cohen et al. | 604/384 |
| 5,746,732 A | 5/1998 | Olsson et al. | 604/385.2 |
| 5,752,947 A | 5/1998 | Awolin | 604/387 |
| 5,769,835 A | 6/1998 | Fell et al. | 604/385.2 |
| 5,779,860 A | 7/1998 | Hollenberg et al. | 162/206 |
| 5,792,129 A | 8/1998 | Johansson et al. | 604/387 |
| 5,792,130 A | 8/1998 | Widlund et al. | 604/385.1 |
| 5,807,365 A | 9/1998 | Luceri | 604/367 |
| 5,807,367 A | 9/1998 | Dilnik et al. | 604/369 |
| 5,810,798 A * | 9/1998 | Finch et al. | 604/378 |

| | | | |
|---|---|---|---|
| 5,865,824 A | | 2/1999 | Chen et al. .................. 604/378 |
| 5,990,377 A | * | 11/1999 | Chen et al. .................. 604/381 |
| 6,103,953 A | * | 8/2000 | Cree et al. ................... 604/365 |

OTHER PUBLICATIONS

Dullien, F. A. L., Porous Media: Fluid Transport and Pore Structure, Academic Press, New York, 1979, pp. 78–83.

Federal Specification UU–T–595b, "Towel, Wiping, Paper: Industrial And Institutional," Apr. 4, 1967, 8 pages.

Federal Specification UU–T–595C, "Towel, Wiping, Paper: Industrial And Institutional," Jul. 27, 1976, 8 pages.

Kallmes, O.J. et al., "The Gravimetric Absorbency Testing System (GATS)," Tappi Symposium—1985 Nonwovens Symposium, pp. 231–235.

* cited by examiner

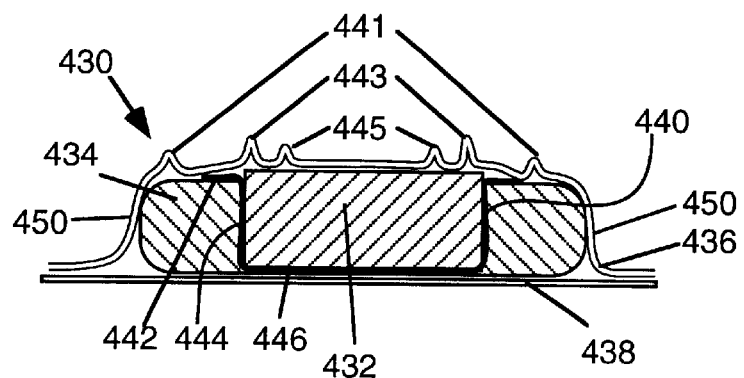
FIG. 19A
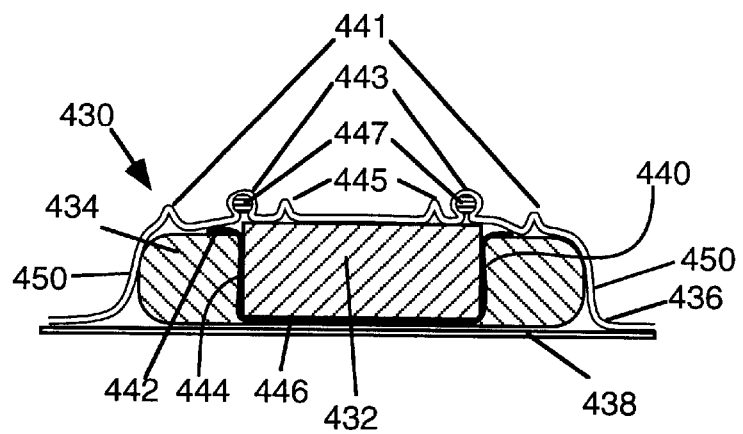
FIG. 19B
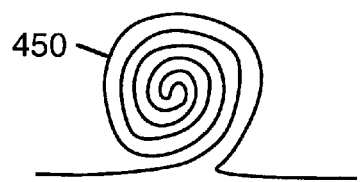 
FIG. 20A  FIG. 20B

ABSORBENT ARTICLE WITH CENTER FILL PERFORMANCE

BACKGROUND OF THE INVENTION

To prevent leakage of body exudates from absorbent articles such as feminine care pads or napkins and disposable diapers, it is desirable that the exudates not reach the edges of the absorbent material in the article. A "center fill" strategy is desirable for leakage control, wherein fluids are preferentially held in a central region of the article. Further, absorbent articles with center fill strategies are desirable for the clean appearance they offer and the reduced wetted area in contact with skin. Unfortunately, in traditional absorbent articles, there is generally no barrier to bulk flow or capillary wicking from the target region to the edges of the article.

Efforts to prevent leakage from the sides of absorbent articles include using fluid impervious cuffs and flaps. These added barriers are costly and do not prevent fluid from reaching the edge of the absorbent article, though they can be effective in reducing leakage in some absorbent articles.

Central meltblown strips and other narrow strips of absorbent material have been added to the body side of absorbent articles to promote center filling of the articles. However, meltblown strips interfere with absorption of fluid into the absorbent cellulosic portions of the article and can hold wet fluid near the skin. Other efforts at controlling fluid intake to promote central filling have used narrow strips of cellulosic or other absorbent material with a horizontal barrier between the strip and the underlying absorbent core. The horizontal barrier material for delaying wicking provides vertical isolation of the central strip from the absorbent core, but does not prevent flow out of the sides of the wetted strip or toward the sides of the article. Further, the horizontal fluid barrier often occupies a significant portion of the article's surface area and can result in ineffective use of the underlying absorbent core.

Embossing has also been used to promote longitudinal fluid flow, but embossments generally are not successful in preventing lateral wicking and in promoting true center fill. Furthermore, heavy embossing can be an ineffective use of absorbent material since the embossed regions are typically highly densified, generally having little pore volume for absorption of fluid.

Longitudinal chambers have also been used wherein each channel or chamber of absorbent material is completely isolated from the next by means of impervious or flow restricting walls. In some cases, however, isolated chambers represent a poor use of absorbent material as one chamber may become overloaded and overflow onto the cover, resulting in smearing and inefficient use of the absorbent material in other chambers. Successful use of isolated chambers requires improvements for prevention of chamber overflow, prevention of undesirable surface transport and smearing, and improved use of the absorbent material in the absorbent article. Further, prior attempts at isolated flow chambers are generally complex in execution, costly, and may suffer from poor product integrity. Improved approaches are needed that can be mass produced for low cost while achieving high levels of performance.

In general, what is needed is an improved means for promoting center fill and reducing flow toward the edges of the absorbent article for leakage reduction that offers improved feel and appearance of the article while also reducing smearing or other forms of failure.

SUMMARY OF THE INVENTION

In one aspect, the present invention resides in an absorbent article having a longitudinal direction, a transverse direction, a vertical direction substantially normal to both the longitudinal and transverse directions, and a body side, the absorbent article comprising:

a) an absorbent core having a body side surface, the core comprising an outer absorbent member having a central void open toward the body side of the absorbent article, and a central absorbent member disposed over the central void of the outer absorbent member and extending into the void; and b) a wicking barrier disposed between the outer absorbent member and the central absorbent member, the wicking barrier comprising a vertical component and a horizontal component, the vertical component spanning a vertical distance between the outer absorbent member and the central absorbent member, and the horizontal component spanning a horizontal distance on the body side surface of the absorbent core.

In another aspect, the invention resides in an absorbent article having a body side, the absorbent article comprising an absorbent core having a body-side surface and comprising an outer absorbent member and a central absorbent member having a perimeter, and a wicking barrier spanning a vertical distance disposed along at least a portion of the perimeter of the central absorbent member, the wicking barrier also comprising a horizontal component residing on the body-side surface of the absorbent core.

In another aspect, the invention resides in an absorbent article having a longitudinal direction, a transverse direction, and a vertical direction substantially normal to both the longitudinal and transverse directions, a crotch region, and a body side, the absorbent article comprising:

a) an absorbent core having a body side surface, the absorbent core comprising a central absorbent member surrounded by a outer shaping member with a central void for receiving the central absorbent member;

b) a baffle layer beneath the central absorbent member; and c) a wicking barrier disposed between the outer shaping member and the central absorbent member, the wicking barrier comprising a vertical component and a horizontal component, and the horizontal component spanning a horizontal distance on the body side surface of the outer shaping member.

In another aspect, the invention resides in an absorbent article with a longitudinal direction, a transverse direction, a vertical direction substantially normal to both the longitudinal and transverse directions, a body side, and a garment side, the absorbent article comprising:

a) an absorbent core having a central absorbent member and an outer absorbent member, the outer absorbent member having a central void defined therein for receiving at least a portion of the central absorbent member, whereby an interface is defined between the central absorbent member and the outer absorbent member; and b) a wicking barrier, desirably a single-ply wicking barrier, disposed along the interface between the central absorbent member and the outer absorbent member, the wicking barrier spanning a vertical distance in the absorbent article and having a variable liquid permeability such that the liquid permeability of the wicking barrier is lower near the body side and higher near the garment side.

The wicking barrier can extend downward from the surface of the absorbent core to span a vertical distance less than the vertical distance of the interface, or, alternatively, can extend substantially along the entire vertical distance of the interface and is provided with apertures or openings away from the body side of the absorbent core such that fluid passing through the wicking barrier must follow an elongated or tortuous path to pass out of the central absorbent member. The wicking barrier can also be provided with a horizontal component on or near the surface of the absorbent core spanning a horizontal distance to reduce the likelihood of contact between the outer absorbent member and the central absorbent member when the article is laterally compressed or bunched together in use.

In another aspect, the invention resides in an absorbent article with a crotch region, a longitudinal direction, a transverse direction, and a vertical direction substantially normal to both the longitudinal and transverse directions, the absorbent article comprising:

a) an absorbent core having a central absorbent member and an outer shaping member, the outer shaping member having a central void defined therein for receiving at least a portion of the central absorbent member, whereby an interface is defined between the central absorbent member and the outer shaping member, the interface spanning a vertical distance, the outer shaping member suitably having a thickness of at least about 1 mm, an edge width of at least about 2 mm, and a basis weight of at least about 100 gsm; and b) a wicking barrier disposed along the interface between the central absorbent member and the outer absorbent member.

In another aspect, the invention resides in an absorbent article comprising an absorbent core comprising an outer absorbent member and a central absorbent member, the outer absorbent member having a central void therein for receiving an insert, and the central absorbent member being inserted into the central void, and a wicking barrier between the outer absorbent member and the central absorbent member, the wicking barrier spanning a vertical distance that can be substantially as great as the thickness of the central absorbent member or can be less than the thickness of the central absorbent member. The central void can be a hole that passes completely through the outer absorbent member, or can be a depressed region within a contiguous, uninterrupted outer absorbent member. Desirably, the wicking barrier comprises a horizontal component that serves as a ledge on the surface of the absorbent core. In one embodiment, the central void longitudinally divides the outer absorbent member into two noncontiguous sections. In other embodiments, the outer absorbent member is divided by the central void in the crotch region, but the outer absorbent member may be contiguous in the front or back portions of the article (i.e., the central void does not extend substantially beyond the crotch region).

In another aspect, the present invention resides in an absorbent article comprising a composite absorbent core having a center, the absorbent core having a body side surface and comprising a central absorbent member and a surrounding outer absorbent member, wherein a plurality of vertically oriented segments of hydrophobic material in the central absorbent member define liquid wicking pathways from the center of the central absorbent member to the outer absorbent member.

In another aspect, the invention resides in an absorbent article comprising a backsheet and a concentric absorbent structure attached to the backsheet, the concentric absorbent structure having a thickness and comprising multiple alternating concentric layers of barrier material and absorbent material, wherein the barrier material substantially spans the thickness of the concentric absorbent structure.

In another aspect, the invention resides in a method for producing an absorbent article having a central absorbent member, the method comprising:

a) preparing an outer absorbent member, wherein the outer absorbent member has a central void;

b) deposing a layer of a flexible barrier material over the central void; and c) inserting a section of absorbent material into the central void and over the barrier material to form a central absorbent member, such that a portion of the barrier material separates the central absorbent member from the outer absorbent member along a vertical distance.

The above method may further comprise deposing a backsheet beneath the absorbent core; deposing a topsheet above the absorbent core; and attaching a portion of the topsheet to a portion of the backsheet.

In another aspect, the invention resides in a method for producing an absorbent article having a central absorbent member, a garment side, and a body side, the method comprising:

a) preparing an outer shaping member having a first portion and a second portion with a central void between the first portion and the second portion, wherein the central void has a vertical depth and the outer shaping member has a surface comprising a wicking barrier that spans at least a portion of the vertical depth of the central void; and b) inserting an absorbent material into the central void of the outer shaping member to form a central absorbent member.

In yet another aspect, the invention resides in a method of preparing an absorbent article comprising a concentric absorbent structure with multiple vertical wicking barriers interposed between layers of absorbent material, the method comprising:

a) superposing at least one layer of a barrier material onto at least one layer of absorbent material to form a multilayered structure;

b) rolling the multilayered structure about a rolling axis to form a spiral wound roll;

c) slicing a portion of the spiral wound roll substantially normal to the rolling axis to form a substantially concentric absorbent structure; and d) attaching the substantially concentric absorbent structure to a backsheet.

BRIEF DESCRIPTION OF THE DRAWINGS

FIG. 19 shows cross-sections of an absorbent article comprising multiple protruding loops of cover material to form runoff barriers on the body-side surface.

FIG. 20 shows two exemplary forms of loops of cover material having multiple folds.

DETAILED DESCRIPTION OF THE INVENTION

Figure 1A:
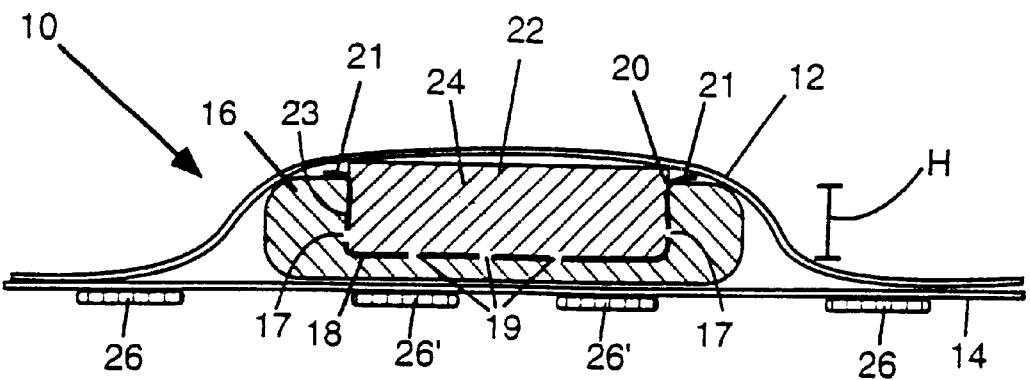
FIG. 1 depicts a cross-section of a sanitary napkin of the present invention.

To fully achieve a center-fill effect for fluid in an absorbent article such as a sanitary napkin or diaper, it has been discovered that excellent results are obtained when a central absorbent member is properly isolated from a surrounding outer absorbent member of the article, such that fluid communication between the absorbent members is reduced, impeded, or prevented. The isolation can be achieved with barrier material spanning a vertical distance between a central absorbent member and a surrounding outer absorbent member to interfere with wicking of fluid (or other forms of flow) from the center of the absorbent article toward the edges of the article. Alternatively, the outer absorbent member may be replaced with a resilient outer shaping member that need not be absorbent. Further, the barrier material desirably can also span a horizontal distance on the surface of the absorbent core of the article for reduced leakage and improved control of fluid flow. The horizontal component of the wicking barrier serves as a ledge on the absorbent core with multiple desirable functions, hereafter described.

The vertical wicking barriers isolate absorbent members of the absorbent core for reduced leakage to the side without the disadvantage offered by horizontal barriers or horizontal transfer delay layers of making absorbent material in the center of the article less accessible to incoming flow. Specifically, the wicking barriers isolate or partially isolate a central absorbent member from the surrounding portions of an outer absorbent member such that in-plane or lateral wicking of fluid is impaired, and thus can be termed "wicking barriers to lateral flow." The term "lateral," as used herein, refers to the in-plane flow directions in an absorbent article, particularly the direction of flow from the central portions of an absorbent core toward the outer edges of the article, particularly the longitudinal edges. More specifically, in-plane flow from the center to the outer regions of an absorbent core can be termed "radially outward flow." The use of vertical wicking barriers permits any desired portions of the body side surface of each absorbent component to remain available for fluid intake and generally provides for more efficient use of absorbent material.

In most embodiments of the present invention, the flow isolating effect within the absorbent core is achieved at least in part because the wicking barrier spans a vertical distance between the central absorbent member and the surrounding portion of the absorbent core (i.e., the outer absorbent member, which may surround the entire central absorbent member or only surround its edges in the crotch region or other region where lateral leakage is likely), thus giving a vertical component to the barrier. Therefore, the barriers can also be termed "vertical wicking barriers" due to the vertical component of the geometry. The vertical component of the wicking barrier spans a vertical distance that is desirably of at least about 20 percent, more desirably of at least about 50 percent, suitably of at least about 70 percent, and up to about 100 percent of the average thickness of the central absorbent member.

The central absorbent member can lie within a depression or void within a surrounding outer absorbent member or can lie substantially above the outer absorbent member and can also serve as the primary absorbent material of the absorbent article. It has also been discovered that isolation of a central absorbent member can be achieved without promoting overflow of liquid entering the central absorbent member due to excessive saturation and without promoting surface smearing. This can be achieved by providing tortuous pathways for fluid flow from the target area to the surrounding absorbent material, thus permitting fluid to move toward the outer absorbent member when the absorbent capacity of the central absorbent member is approached, but whereby such radially outward flow is delayed or impeded by the tortuous pathways. Wicking barriers with vertical components establish the tortuous or labyrinth-like flow pathways by which fluid in the center of an absorbent core can gradually move toward the outer absorbent member of the pad in a way that reduces leakage and enhances utilization of the absorbent material.

In one class of related embodiments, the wicking barrier does not completely separate the adjacent zones of absorbent material but prevents radially outward flow (flow from the center of the pad to the edges, especially the longitudinal edges of the article) in the upper regions of the absorbent zones near the user's body, while permitting some degree of radially outward flow through tortuous pathways or labyrinth-like pathways, preferably pathways remote from the body side or upper surface of the absorbent core, such that the outer absorbent member or regions of the article can serve a useful absorbent function, such as providing a source of additional absorbent capacity when the main absorbent capacity of the central absorbent member is exceeded, or serving as an indicator that the article should be replaced. For example, a wicking barrier comprising an impervious film may form a wall around a central absorbent insert placed within a hole in an outer absorbent member, but still permit some radially outward flow away from the body side surface if the lower portions of the film away from the body side surface are provided with apertures through which fluid can flow when the central absorbent member becomes saturated.

While the wicking barriers can interfere with wicking flow, wherein capillary forces move the fluid, the wicking barriers naturally can impede more rapid flow as well, including gushes of flow driven by hydraulic pressure or gravitational force. Thus, the flow isolation effect of the wicking barrier is not limited to wicking flow alone.

One problem known with previous attempts at isolating longitudinal chambers of absorbent material has been surface smearing of the fluid, typically due to a single isolated chamber becoming saturated with fluid and then forcing additional fluid to flow along the surface of the article to other chambers or to the edges of the article. If the primary fluid pathway from one absorbent region or member to the next is along the surface of the article, smearing is likely. Likewise, complete isolation of an absorbent member can keep that member wet and provide discomfort to the user and result in inefficient use of the absorbent material of the article. Accordingly, surface smearing and oversaturation of the target region of the absorbent article can be reduced by any or all of the following: 1) redistributing the mass and/or the absorbent capacity in the absorbent article such that the central absorbent member has substantially greater basis weight and/or absorbent capacity than the outer absorbent member of the absorbent article, and desirably also has a greater thickness to ensure preferential contact of fluid with the central absorbent member; 2) providing flow pathways from the central absorbent member to the surrounding or adjacent outer absorbent member or regions that are remote from the surface of the absorbent article such that fluid flow from one member to the next is possible by a route other than along the surface, such as by openings in the wicking barrier away from the upper surface of the article, and desirably by a tortuous route that delays lateral wicking enough for effective center fill without promoting overflow or oversaturation; 3) providing a horizontal component to the barrier material such that a portion of the barrier material resides on the surface of the absorbent core in addition to the portion spanning a vertical distance between adjacent absorbent members, thus forming "ledges" of barrier material near the surface of the absorbent article (desirably beneath the cover but above the absorbent core).

The development of vertical wicking barriers with horizontal components on the body-side surface of the absorbent core of an absorbent article is believed to offer many advantages previously unavailable in absorbent articles. First, the horizontal component is especially effective in preventing wicking contact between the central absorbent member and the adjacent outer absorbent member. If a vertical barrier ends abruptly at the surface between two adjacent chambers, there is the possibility that wicking contact between the two chambers will be established at the upper surface of the article, especially if the article is laterally compressed or bunched together in use or if the article experiences in-plane shear that can move the upper layers of one absorbent member toward other absorbent members in the absorbent article. Even a small region of contact between adjacent absorbent members can result in undesired lateral wicking, and since the fluid flow between the two members in that case will be primarily along the surface, surface smearing is a possibility. A horizontal component, or ledge, at the top of the vertical wicking barrier can greatly increase the effectiveness of the wicking barrier and isolate the upper regions of the adjacent absorbent members, thus reducing the chances of surface smearing and preventing undesired flow toward the edges of the article, from whence the fluid may leak and soil the wearer's clothes.

Second, the ledge can redirect flow toward the central absorbent member, increase the center-fill effect, and increase the effective size of the central absorbent member. Particularly desirable is a hydrophobic ledge around or along the central absorbent member extending away from the central absorbent member and toward the edges of the article, spanning a short horizontal distance, and preferably a distance approximately equal to a characteristic drop size of the fluid being absorbed. For many absorbent articles, the horizontal distance spanned is desirably between about 0.3 millimeters (mm) and about 5 mm, and specifically between about 0.5 mm and about 3 mm, more specifically between about 1 mm and about 2.5 mm, and alternatively between about 0.2 mm and about 2 mm. When fluid is deposited on such a ledge, the fluid can be redirected toward the central absorbent member instead of flowing into the underlying outer absorbent member. Desirably, the ledge lies on the outer absorbent member and helps redirect fluid toward the central absorbent member. This is especially effective when the central absorbent member is more elevated than the outer absorbent member, so that fluid on the ledge is likely to contact the elevated, adjacent central absorbent member. However, in one embodiment, the ledge can extend substantially all the way to the longitudinal edges of the crotch region of the outer absorbent member. In a related embodiment, the ledge can substantially cover all of the body side surface of the outer absorbent member outside the perimeter of the central absorbent member. This is particularly helpful when the central absorbent member is sufficiently sized and placed to receive essentially all of the liquid received by the absorbent article so essentially none falls on the ledge. In this manner, the ledge can provide excellent wicking isolation of the central absorbent member from the outer absorbent member even under extreme bunching of the article during dynamic use.

Third, the ledge can provide increased stability, strength, and resiliency to an absorbent article. This is particularly so when the ledge is adhesively or otherwise attached to the cover or topsheet of an absorbent article and/or to one or more elements of the absorbent core. A problem in some previous attempts at providing isolated chambers in an absorbent article is that a film or other barrier between adjacent chambers eliminates the fiber-fiber bonding or entanglement between fibers that holds an absorbent core together, resulting in an absorbent core which can come apart, separate, or fail either in tension or compression or during bending. In the present invention, the ledge of the wicking barrier is easily attached to the cover and can further be attached to either or both of the central absorbent member and the outer absorbent member adhesively, by thermal or ultrasonic bonds, or by other attachment means known to one skilled in the art. By geometric considerations alone, a wicking barrier with a ledge can effectively hold the central absorbent member in place between the wicking barrier and the cover when the ledge is attached to the cover or to the surface of the outer absorbent member.

Fourth, the ledge of the wicking barrier can serve important visual roles. It can help the wearer with proper placement by clearly marking the intended target zone, particularly if the wicking barrier has a color such as pink or blue that contrasts well with the absorbent material of the core. It can provide an important visual cue to the user that a central absorbent member exists and that the article provides a center fill strategy. The visible "protection zone" can increase user confidence in the article and can provide an improved clean appearance to the article, even after use. Further, if the ledge is at least somewhat opaque, it can mask incipient lateral flow from the central absorbent member to the outer absorbent member. Thus, a desirable wicking barrier material can be a thin, flexible polyolefin film or nonwoven layer, such as a web having a basis weight less than 40 grams per square meter (gsm) and desirably less than 25 gsm, optionally comprising coloring agents and desirably comprising pigments or fillers such as titanium dioxide or calcium carbonate for opacity.

In addition, surface smearing can be reduced with the use of a cover material that is especially well suited for the vertical barriers and vertical barriers with horizontal components of the present invention. Such a cover material comprises an inherently hydrophilic basesheet with a three-dimensional topography, further comprising hydrophobic matter deposited on the uppermost portions of the basesheet. Such covers are disclosed in the commonly owned copending U.S. patent application Ser. No. 08/997,287, "Dual-zoned Absorbent Webs," filed Dec. 22, 1997, by Chen et al., herein incorporated by reference in its entirety. A three-dimensional, wet resilient tissue, for example, with a crosslinked silicone material on the uppermost regions of the surface, can provide an excellent dry feel while permitting good fluid entry into an absorbent basesheet. If the upper region of the underlying central absorbent member comprises a densified airlaid strip or other material having higher capillary pressure than the hydrophilic basesheet of a dual-zoned cover, then fluid can be pulled effectively from the basesheet of the cover into the absorbent core, resulting in small stain sizes and exceptionally dry feel.

Tortuous pathways from the central absorbent member to the outer absorbent member can be provided in a variety of ways. A single layer of hydrophobic barrier material between the central absorbent member and the surrounding outer absorbent member can comprise small apertures, slits, or holes remote from the body side of the absorbent article such that fluid entering the central absorbent member must travel downward through a substantial portion of the thickness of the central absorbent member before having access to openings leading to absorbent material outside the central absorbent member. The apertures or flow openings desirably are not present in the crotch region of the article, but can be placed closer to the longitudinal ends of the central absorbent member such that wicking through the apertures only occurs after fluid has been wicked longitudinally in the central absorbent member toward its ends, and then the fluid will still be remote from the crotch region where leakage tends to be more problematic in most absorbent articles. More complex and tortuous pathways can be created through the use of barrier material arranged in a spiral design from the central portions of the absorbent article to the outer regions, such that fluid in the center must wick along a spiral path in the plane of the article to reach the outer regions of the article. Likewise, barrier material may be arranged to define a labyrinth-like pathway from the central portions of the article to the outer regions, such that in-plane wicking can occur but only along a complex route. Combinations of labyrinth-like pathways and apertures or openings in selected portions of the barrier material can be used.

The barrier material may be impervious or may be permeable to liquid or, in one embodiment, has a variable permeability, particularly a vertical gradient in permeability and/or porosity such that the lowest permeability or porosity of the barrier material is found near the body side of the absorbent core or the absorbent article and the highest permeability is near the garment side of the absorbent core or the absorbent article, with the permeability or porosity of the barrier material increasing with vertical distance from the body side to the garment side such that lateral flow is most strongly hindered near the body side and least hindered near the garment side.

Possible uses of the present invention include absorbent articles for intake, distribution, and retention of human body fluids. Examples include feminine care pads and related catamenial devices or sanitary napkins, including "ultrathin" pads and pantiliners and maxipads. Examples of ultrathin sanitary napkins are disclosed in U.S. Pat. Nos. 4,950,264 and 5,009,653 issued to Osborn; and U.S. Pat. No. 5,649,916, issued Jul. 22, 1997 to DiPalma et al., each of which are herein incorporated by reference in their entireties. Likewise, the present invention can be applied to diapers, disposable training pants, other disposable garments such as swimming garments, incontinence articles, bed pads, sweat absorbing pads, shoe pads, bandages, helmet liners, wipes and wipers, or other absorbent articles. The present invention can also be incorporated in articles adapted for particular portions of garments to be worn on the human body, gaskets for ostomy bags, and medical absorbents and wound dressings. The articles of the present invention provide significant leakage protection, fluid center-fill absorptive performance, and other desirable attributes for absorbent articles.

For feminine care pads in particular, the present invention offers surprising advantages in terms of comfort and fit. When the central absorbent member and the outer absorbent member are physically separate members, the transverse compressive stiffness of the article is greatly reduced. In other words, the article can bend between the user's thighs more easily and feels less stiff. Placing longitudinal slits in the central absorbent member is also helpful in reducing transverse stiffness. Further, the presence of a wicking barrier between the two absorbent members can enhance the ability of one absorbent member to move relative to another, as by sliding along the wicking barrier during transverse compression, especially if the wicking barrier is not adhesively attached to both absorbent members across the wicking barrier's entire surface, or if the wicking barrier is adhesively attached to no more than one absorbent member. Thus, the wicking barrier can provide additional freedom of movement and freedom of deformation to the absorbent members for reduced stiffness and better body fit. The presence of a wicking barrier with a vertical component in the crotch region, which separates the central absorbent member and outer absorbent member and allows folding or motion therebetween, appears especially useful in promoting a W-shape geometry of sanitary napkins when compressed in use which can rise toward the body for better intake of fluid and better fit in general. Further still, the center-fill strategy made possible by the present invention can be used to generally ensure that the outer absorbent member remains dry under typical usage conditions, which in turn allows the outer absorbent member to better maintain its shape and to help hold the pad in a comfortable and effective position.

Indeed, recognizing that the primary absorbent material in the central absorbent member can provide substantially all of the absorbent capacity needed for many absorbent articles such as a feminine care pad (typically 7 milliliters (ml) of fluid will be absorbed, with a high end of about 15 ml), the outer absorbent member can be used to achieve several important functions other than absorbency. Either as a ring of material around the central absorbent member or as a pair of longitudinal bands surrounding the central absorbent member longitudinally, the outer member helps define the shape of the article, particularly when attached adequately to the wearer's panties. In conventional sanitary napkins, the article can become excessively bunched or compressed when wetted, but by maintaining the outer absorbent member in a dry state, it can maintain its shaping and body fit functions throughout use. Thus, the outer absorbent member can serve as a shaping and body fit element as well as a "cradle" to hold the central absorbent member and the wicking barrier in place. In fact, these functions can be achieved whether the outer member is absorbent or not, though it is desirable that the outer member be absorbent to take up fluid that might not be successfully held by the central absorbent member. Nevertheless, in one embodiment of an absorbent article such as a feminine care pad designed to maintain good body fit and provide leakage protection, the outer member need not be absorbent at all but can be a flexible frame member capable of holding the wicking barrier and central absorbent member in place. Thus, an outer shaping member can be used instead of an outer absorbent member, though it is preferred that the outer member be absorbent.

The shaping member can be porous, such as a ring of a polyurethane foam; a polyethylene foam such as the product known as VOLARA™ 2a polyethylene foam, obtained from Voltek Corp., of Lawrence, Mass.; or a foam rubber material (e.g., foamed styrene butadiene), foamed silicones, or foamed vinyl plastics. Several such foams can be obtained from Woodbridge Foam Fabricating, Inc., located in Chattanooga, Tenn., from the E. N. Murray Company, Inc., located in Denver, Colo., and Astro-Valcour, Inc., located in Glens Falls, N.Y. Foam materials desirably have a density of about 0.02 grams per cubic centimeter (g/cc) to about 0.1 g/cc. The foam material desirably is treated to be absorbent and/or hydrophilic, but need not be hydrophilic. In the case of a closed-cell foam or a foam with an impervious skin on the outer surface, the surface of the foam itself can serve as a wicking barrier having both a vertical component and a horizontal component on the bodyside surface of the shaping member. Thus, in general, the shaping member can comprise an integral wicking barrier or can have an additional polymeric barrier provided on its surface, or can be separated from the central absorbent member by a separate layer of barrier material serving as a wicking barrier.

In one related embodiment, the wicking barrier and the outer shaping member are also integral with a backsheet and can be composed from a single piece of impervious material. The backsheet then also can serve as the baffle layer beneath the central absorbent member. For example, a single section of shaped flexible closed cell foam, desirably comprising an external impervious skin, can be shaped to provide a thin central layer under the central absorbent member, expanding away from the longitudinal centerline to provide thicker regions outside the central absorbent member that serve as the outer portions of the outer shaping member. (The thin central portion is a bridging portion between the outer portions.) Since the central absorbent member is contained by the outer shaping member (within the central sides of the outer portions and above the underlying thin bridging region of the foam body), there is no need for an additional backsheet, assuming the foam is truly impervious or comprises an impervious skin.

In general, for embodiments with an impervious or non-absorbent outer shaping member, a separate backsheet is not necessary. Nevertheless, some form of a baffle layer must exist beneath the central absorbent member to prevent leakage. If a substantially liquid impervious outer shaping member is used and is contiguous, e.g., comprises first and second outer portions joined by a relatively thin (thinner than the outer portions) bridging member, then the outer shaping member itself can serve as the baffle layer and can replace the function of a backsheet, if desired. If a complete hole rather than merely a depression exists in the central portion of the outer shaping member for receiving the central absorbent member, then a separate baffle layer must be used. This can be a liquid impervious backsheet, a portion of which serves as the baffle layer beneath the central absorbent member, or it can be the wicking barrier if it runs beneath the central absorbent member to prevent leakage of fluid toward the garment side of the article, or it can be a separate layer of impervious or hydrophobic material such as a flexible polymer film, including material integrally attached to the central absorbent member such as a thermoplastic film, or an impervious coating or layer of adhesive. In any case, the construction of the article generally serves to isolate fluid in the central absorbent member for a true center-fill effect and prevent or reduce substantial fluid contact with the outer shaping member, while providing a conformable article that can fit against the body in use.

An outer shaping member comprising foam or other materials can be preshaped to conform suitably to the body.

Examples of materials and methods for preparing conformable, resilient shaped members are disclosed in U.S. Pat. No. 5,591,150, issued Jan. 7, 1997 to Olsen et al., herein incorporated by reference in its entirety. The outer shaping member can comprise absorbent materials, particularly cellulose, such as a regenerated cellulose foam or stabilized fluff pulp or air laid wood fibers, stabilized with thermoplastic fibers, crosslinkers, or wet strength agents, and may be preshaped or can be planar. Desirably, the outer absorbent member comprises densified fluff pulp, stabilized air laid pulp, or the soft pulp sheets disclosed in U.S. Pat. No. 5,562,645, issued Oct. 8, 1996 to Tanzer et al., herein incorporated by reference in its entirety, and desirably has a density less than 0.2 g/cc and more specifically less than 0.1 g/cc, and most specifically less than 0.07 g/cc. Coform, a meltblown air-formed combination of meltblown polymers, such as polypropylene, and absorbent staple fibers, such as cellulose, can also be used. The outer shaping member can be a composite element, such as a layer of cellulosic fibers joined to a polymeric foam layer. In one embodiment, the outer shaping member is extensible such that its size can be adjusted for improved fit. The outer shaping member can also be biodegradable and/or flushable, if desired. Further, the central absorbent member can be detachable to permit disposal and replacement with a new central absorbent member, rather than discarding the entire article.

In one embodiment, the outer shaping member can comprise gas-filled bubbles sealed inside polymeric material, such as air bubbles sealed between two layers of a polymeric film similar to a bubble wrap material commonly used for protection of articles during shipment. The gas-filled bubbles can be optimized in size and shape to conform to the body and provide shaping, cushioning, and gasketing functions, while preventing wicking from the central absorbent member. In such embodiments, the width of the central absorbent member desirably should be no more than 2 to 4 cm, and the shaping member should have a thickness of at least about 2 mm, desirably from about 2.5 mm to 7 mm, with a width (distance from the edge of the outer absorbent member to the outer longitudinal side of the shaping member) of at least 1 mm and desirably at least about 3 mm. The shaping member in such embodiments can comprise one or more gas-filled bubbles having a volume of at least about 0.2 cubic centimeters, desirably at least about 0.5 cubic centimeters, and more desirably at least about 1 cubic centimeter.

As with the outer absorbent member, the outer shaping member desirably promotes good body conformability. When used in sanitary napkins or feminine pads, for example, the outer shaping member desirably promotes a W-fold geometry in the crotch region when the pad is worn. Thus, the size, thickness, stiffness, and geometry of the outer shaping member should be adjusted to permit it to flex in use into a W-fold when combined with the other components of the absorbent article. Design principles given herein for embodiments comprising an outer absorbent member can generally be applied to embodiments comprising an outer shaping member, in addition to explicit teachings herein for the outer shaping member.

For best comfort, the outer shaping member or outer absorbent member desirably should be soft, resilient and easily compressible. The resiliency should be in the range of about 15 percent to about 60 percent rebound, preferably about 15 percent to about 50 percent and more preferably about 15 percent to about 35 percent, as determined by the ASTM Test Method D3574-91 procedure H. Compressibility should be in the range of about 0.69 kPa (0.1 pounds per square inch (psi)) to about 13.8 kPa (2 psi) at 50% compression, preferably from about 2.1 kPa (0.3 psi) to about 11.7 kPa (1.7 psi) at 50% compression and most preferably from about 3.45 kPa (0.5 psi) to about 10.3 kPa (1.5 psi) at 50% compression, as determined by the ASTM Test Method D3574-91 procedure C.

Generally, the outer shaping member has a thickness of at least about 1 mm, specifically at least about 2 mm, more specifically at least about 3 mm, and most specifically from about 3 mm to about 7 mm. Desirably, the average thickness of the shaping member is at least about 20 percent of the average thickness of the central absorbent member, and more specifically is at least about 30 percent of the average thickness of the central absorbent member. The thickness of the outer shaping member can also be greater than that of the central absorbent member. For example, the average thickness of the central absorbent member can lower by at least about 20 percent or at least about 50 percent than the average thickness of the outer shaping member.

The "edge width" of the outer shaping member, defined herein as the lateral distance along a continuous portion of the outer shaping member along the transverse centerline, specifically from the inner edge (adjacent the central absorbent member) of the outer shaping member to the outer edge thereof, is desirably at least about 2 mm and specifically at least about 3 mm, more specifically at least about 4 mm. For example, a 7 cm wide rectangular foam section with a 5 cm wide central depression therein for receiving a central absorbent member would have an edge width of 1 cm.

In a preferred embodiment, the outer shaping member is also an outer absorbent member comprising cellulosic fibers, the outer absorbent member being substantially surrounded by impervious material (e.g., the wicking barrier and the backsheet) such that the absorbent material remains substantially dry in use. In one embodiment, the wicking barrier completely covers the body-side surface of the outer absorbent member and forms a seal with the backsheet in the region between the outer absorbent member and the central absorbent member and, optionally, is attached to the backsheet adjacent the outer periphery of the outer absorbent member. Small apertures may be provided in the wicking barrier to permit some fluid intake into the outer absorbent member when the central absorbent member is heavily saturated, but ordinarily the outer absorbent member will remain dry. The apertures may be provided only near the longitudinal ends of the central absorbent member such that fluid cannot wick directly toward the crotch region of the outer absorbent member. Thus, the outer absorbent member primarily serves to provide comfort and body fit, while providing a substrate on which the wicking barrier can rest to resist fluid flowing out of the article.

The absorbent articles of the present invention can comprise a topsheet or a backsheet or both a topsheet and a backsheet, or other means to provide integrity to the article and comfort on the body side surface. An article can be made without a topsheet and/or without a backsheet, particularly if other components are present to provide suitable integrity of the product and liquid barrier functions. For example, a wicking barrier can be attached to the central absorbent member by attachment means including adhesives, ultrasonic bonds, threads, fiber-fiber entanglement, hook and loop structures, embossments, thermal bonds, elastic ligaments, and other means known in the art to hold the central absorbent member in place. The wicking barrier may also be attached to the outer absorbent member or outer shaping member by similar attachment means to hold it in place. Thus, the restraining or integrity-providing effect of the topsheet and backsheet in normal absorbent articles could be replaced by a wicking barrier suitably attached to the other components of the article. The wicking barrier may also wrap the outer absorbent member or outer shaping member to hold it in place and provide a liquid barrier function around or beneath that member. Comfort, softness, and dry feel functions of a conventional topsheet can be replaced by using suitable absorbent materials, particularly those that have been provided with additional hydrophobic material on the surface of the absorbent material to permit fluid intake yet provide a dry feel against the skin. Tufts of hydrophobic fibers attached to the absorbent core or spaced apart, elevated mounds of silicone material or other hydrophobic material on the surface may simulate the function of apertured films or nonwoven webs without necessarily forming a separate topsheet. Densified airlaid webs with sufficient integrity and optionally a portion of hydrophobic fibers on the surface can also be used for direct contact with the skin. Traditional topsheet materials such as nonwoven webs or apertured films can also be used to cover only a portion of the absorbent article, such as covering only the central absorbent member or only the outer absorbent member or outer shaping member. Likewise, backsheet material may be present on only a portion of the garment side of an article, such as beneath the central absorbent member where it can serve as a baffle layer. In many embodiments of the present invention, however, it is likely that topsheets and backsheets will be used. Useful guidelines for both topsheets and backsheets now follow.

The topsheet has a body-facing side and a core-facing side. The body-facing side of the topsheet generally forms at least a portion of the body surface of the article. The topsheet should permit liquids to readily transfer through its thickness toward the absorbent core. The topsheet can comprise any fluid pervious cover material known in the art, such as nonwoven webs or apertured films, or other materials such as hydrophilic wet laid basesheets treated with portions of hydrophobic matter, including those of Chen et al. in commonly owned copending application, "Dual-zoned Absorbent Webs", Ser. No. 08/997,287, filed Dec. 22, 1997, previously incorporated by reference. Nonwoven webs used to produce a topsheet can include layers of spunbond material, meltblown material, and combinations thereof. The nonwoven webs may be apertured or slitted webs or provided with treatments for improved wettability, including corona discharge treatment, or treatments for improved flow permeability, such as hydroentangling or aperturing or microembossing. Creping of the nonwoven web using methods known in the art can desirably improve softness, appearance, and performance of the topsheet. The topsheet can comprise a layer of a perf-embossed or apertured film on the body side bonded to a layer of a nonwoven web, preferably treated to be hydrophilic, on the core side. Similarly, the topsheet can comprise two or more nonwoven layers or film and nonwoven layers that have been co-apertured to provide apertures suitable for rapid intake of viscous or viscoelastic fluids and to improve wicking contact with underlying absorbent materials. Examples of suitable co-apertured materials are disclosed in U.S. Pat. No. 5,188,625, issued Feb. 23, 1993 to Van Iten et al., herein incorporated by reference in its entirety. If apertured, the topsheet can have about 5 to about 60 percent open area and a thickness of about 0.01 to about 0.1 mm for a film or from about 0.03 to 0.5 mm for a fibrous nonwoven web.

The topsheet desirably is flexible and nonirritating to the wearer's skin. As used herein the term "flexible" refers to materials which are compliant and readily conform to the shape of the body or respond by easily deforming in the presence of external forces. Preferably the topsheet is not noisy, to provide discretion for the wearer. The topsheet desirably can be somewhat opaque to hide the bodily discharges collected in and absorbed by the absorbent core. The topsheet can further exhibit good strikethrough and a reduced tendency to rewet, permitting bodily discharges to rapidly penetrate the topsheet to the core, but not allowing such discharges to flow back through the topsheet to the skin of the wearer.

If desired, the topsheet can be sprayed with a surfactant to enhance fluid penetration to the absorbent core. The surfactant should typically be nonionic and should be nonirritating to the skin. A surfactant density of about 0.01 milligrams per square centimeter of topsheet area is suitable. A suitable surfactant is sold by the Glyco Chemical, Inc. of Greenwich, Conn., as PEGOSPERSE™ 200 ML surfactant.

Exemplary topsheets can be made in accordance with U.S. Pat. No. 5,533,991, issued Jul. 9, 1996 to Kirby et al.; U.S. Pat. No. 4,342,314 issued Aug. 3, 1982 to Radel et al. and U.S. Pat. No. 4,463,045 issued Jul. 31, 1984 to Ahr et al., all of which are incorporated herein by reference. The topsheet may comprise an additional transfer layer to help direct fluid into the absorbent core, as disclosed, for example, in U.S. Pat. No. 4,397,644, issued Aug. 9, 1983 to Matthews et al., herein incorporated by reference.

The topsheet need not have uniform properties but can be preferentially more permeable or liquid pervious or wettable over the central absorbent member than it is elsewhere. For example, the topsheet may be substantially porous and wettable over the central absorbent member but substantially nonwetting over the outer absorbent member. Particularly when the topsheet is adhesively attached to the outer absorbent member such that it remains in contact with the body-side surface of the outer absorbent member when in use, an impervious or nonwettable or low permeability section of the topsheet over the outer absorbent member can also serve the role of a horizontal component in the wicking barrier, though it is more desirable that the horizontal component of the wicking barrier be integral with the vertical component.

The topsheet and the backsheet may be adhesively attached to the absorbent core. Useful principles for adhesively attaching topsheets or other lamina to absorbent cores comprising comminuted fibers are disclosed in U.S. Pat. No. 4,573,986, issued Mar. 4, 1986 to Minetola et al., herein incorporated by reference in its entirety.

In the embodiments requiring a separate backsheet, the backsheet should strong enough for handling and flexible enough to fit body contours comfortably. The backsheet has a core-facing side and a garment side. At least a portion of the core-facing side of the backsheet will ordinarily face the core. The backsheet may be any flexible, liquid impervious material that prevents discharges collected by the absorbent article, such as a sanitary napkin, from escaping the absorbent article and soiling the undergarments and clothing of the wearer. Preferably, the backsheet is not noisy, to provide discretion for the wearer. The backsheet can also be impervious to malodorous gases generated by bodily discharges, so that the malodors do not escape and become noticed by the wearer and others. The backsheet can comprise any material known in the art of absorbent articles, including polymeric films, low-permeability nonwoven webs, cloth layers desirably comprising an impervious layer or film, or polymer-tissue composites.

The backsheet can comprise two layers such as a first layer of a lofted material on the garment-facing side of the backsheet bonded to a second layer such as a polymeric film on the core-facing side. The lofted layer provides a comfortable, non-irritating surface against the body of the wearer. The lofted layer may be comprised of any suitable material, such as a nonwoven material. Desirably, the lofted layer comprises a hydrophobic nonwoven material. The second layer on the core-facing side can comprise a fluid impervious film. A low density polyethylene material about 0.01 to about 0.05 millimeters in thickness, such as about 0.02 millimeters in thickness, can work well as this second layer. The backsheet may also be made of a soft, cloth-like material which is hydrophobic relative to the topsheet. An exemplary cloth-like backsheet material is a laminate of a polyester nonwoven material and a film such as is described in U.S. Pat. No. 4,476,180 issued to Wnuk on Oct. 9, 1984, which is herein incorporated by reference. Another exemplary multi-layered backsheet is that of Linman et al. in U.S. Pat. No. 4,681,793, issued Jul. 21, 1987, herein incorporated by reference, wherein an outer layer with a three-dimensional macroscopically expanded surface is used for better comfort. Desirably, the backsheet is a polyethylene film having a thickness of from about 0.012 mm to about 0.051 mm. Exemplary polyethylene films are manufactured by Clopay Corporation of Cincinnati, Ohio, under the designation P18-0401 and by Tredegar Film Products of Terre Haute, Ind., under the designation XP-39385.

The backsheet and other components may be biodegradable and/or flushable. A flushable article is one that can be directly discarded into a toilet and flushed without clogging piping and without harm to septic systems. Thus, in one embodiment, the backsheet is an impermeable sheet material that rapidly dissolves in cold tap water, and is thereby released from the absorbent core to help render the article flushable. Likewise, the topsheet and the wicking barrier can comprise flushable and/or biodegradable materials. Suitable materials for a flushable backsheet can include polyvinyl alcohol (PVA), starches, rice paper, guar gum, or polylactic acid polymers or copolymers. Other materials and methods for construction of a flushable article are disclosed in U.S. Pat. No. 5,300,358, issued Apr. 5, 1994 to Evers; U.S. Pat. No. 5,509,913, issued Apr. 23, 1996 to Yeo; U.S. Pat. No. 5,405,342, issued Apr.11, 1995 to Roessler et al.; and U.S. Pat. No. 4,522,967, issued Jun. 11, 1985 to Sheldon et al.; all of which herein incorporated by reference in their entireties.

Since flushable structures must be small enough or break down in the toilet water to small enough pieces to flush, in larger flushable articles the core may be segmented into unconnected individual pieces of a flushable size. The division of the absorbent core into a central absorbent member and an outer absorbent member is helpful in achieving such segmentation.

Because an impervious wicking barrier can be beneath the central absorbent member in many embodiments of the present invention, it is not imperative that the backsheet itself be absolutely impervious, at least not over its entire area, for adequate constraint of fluid in the central absorbent member by an impervious wicking barrier may make the primary function of the backsheet to be providing integrity to the article. Nevertheless, for best results, it is desired that the backsheet be substantially impervious, though it can be breathable to permit transmission of water vapor for comfort.

Generally, the topsheet is joined to the core-facing side of the backsheet along the longitudinal edges of the topsheet and can be joined along at least one transverse line such as an end edge.

When a baffle layer beneath the central absorbent member is required, the materials described herein for the backsheet or for the wicking barrier can generally be used, and either the backsheet or wicking barrier can serve as the baffle layer.

The absorbent core comprises two primary sections, a central absorbent member and an outer absorbent member (or, in some embodiments, an outer shaping member, previously described) with a central void or depression therein which can at least partially receive the central absorbent member such that an interface is established between the two sections that spans a finite vertical distance. Desirably, the central absorbent member has at least one in-plane dimension smaller than the corresponding dimension of the outer absorbent member. Generally, the transverse width of the central absorbent member will be less than the transverse width of the outer absorbent member at least in the crotch region. For purposes of the present invention, the absorbent core generally is considered to be a separate component from any flaps or wings added to the article, even if they also comprise absorbent material.

The absorbent materials of the absorbent core, including either the central absorbent member or the outer absorbent member or both, can comprise one or more plies of wetlaid or airlaid tissue; cellulosic airlaid webs of comminuted fibers (commonly termed "airfelt"); other dry laid webs; cellulose-superabsorbent mixtures or composites; hydroentangled webs comprising cellulosic fibers; composites of synthetic fibers and papermaking fibers; cellulosic foams including regenerated cellulose foams; hydrophilic flexible foams; fiber-foam composites; absorbent nonwoven webs; the foam-structured fibrous absorbent materials of F.-J. Chen et al. disclosed in the commonly owned, copending U.S. patent application "Fibrous Absorbent Material and Methods of Making the Same," Ser. No. 09/083,873, filed May 22, 1998, herein incorporated by reference; or absorbent foams produced from high internal phase emulsions (HIPE), such as the foams disclosed in U.S. Pat. No. 5,692,939, issued Dec. 2, 1997 to DesMarais, herein incorporated by reference. The absorbent materials of the absorbent core can also comprise corrugated absorbent materials for enhanced longitudinal transport of fluid, such as the materials disclosed in U.S. Pat. No. 4,578,070, issued Mar. 25, 1986 to Holtman, herein incorporated by reference in its entirety.

A commercially available air-laid web is AIRTEX™ 395 air-laid web sold by Georgia-Pacific Corporation located in Green Bay, Wis. AIRTEX 395 air-laid web is 100% virgin softwood held together by an acrylic binder. Concert Fabrication Ltee, of Quebec, Canada, also produces a variety of densified airlaid webs held together with thermoplastic binder material.

A particularly useful cellulose-polymer composite material is coform, a hydraulically entangled mixture of pulp fibers and polymer, such as the materials disclosed in U.S. Pat. No. 4,879,170, issued Nov. 7, 1989 to Radwanski et al.; U.S. Pat. No. 4,100,324 to Anderson et al. and U.S. Pat. No. 5,350,624 to Georger et al., the contents of which are incorporated herein by reference in their entireties.

Any suitable form of cellulosic material can be incorporated in the absorbent materials of the absorbent core, including wood fibers, such as bleached kraft softwood or hardwood, high yield wood fibers, and chemithermomechanical pulp fibers; bagasse; milkweed; wheat straw; kenaf; hemp; or peat moss. The fibers can also be crosslinked, sulfonated, mercerized, heat treated, mixed with thermoplastic stabilizer fibers, or treated with wet strength agents. Mixtures of various fibers can be used, including coform, which comprises thermoplastic fibers and wood fibers deposited together in an airlaying process.

In one embodiment, the absorbent core comprises a molded, three-dimensional high bulk wet laid cellulosic web, such as an uncreped through-air dried web as taught by F.-J. Chen et al. in commonly owned U.S. patent application Ser. No. 08/912,906, "Wet Resilient Webs and Disposable Articles Made Therewith," filed Aug. 15, 1997; U.S. Pat. No. 5,429,686, issued to Chiu et al. on Jul. 4, 1995; U.S. Pat. No. 5,399,412, issued to S. J. Sudall and S. A. Engel on Mar. 21, 1995; U.S. Pat. No. 5,672,248, issued to Wendt et al. on Sep. 30, 1997; and U.S. Pat. No. 5,607,551, issued to Farrington et al. on Mar. 4, 1997; all of which are herein incorporated in their entirety by reference. Such uncreped structures can offer a plurality of flow channels along the surface of the web. When stacked or layered with other planar materials such as a polymer film, void space can still exist adjacent the surface of the tissue web to permit rapid flow of fluid parallel to the plane of the tissue web. Further, the uncreped tissues show excellent wet resiliency and high bulk under load when wet. Without wishing to be limited by theory, it is believed that the three-dimensional surface structures of such textured webs can maintain their shape and bulk when wet because the hydrogen bonds defining the arrangement of the fibers are formed in the molded, three-dimensional state, so the structure does not relax to a flat state when wetted.

Dimensions of the components of the absorbent article can be suited and optimized for particular functions. For feminine care pads, for example, the outer absorbent member can have a transverse width (distance from one outer longitudinal side to the other across the transverse centerline, not the smaller edge width defined previously) of from about 4 cm to about 8 cm and a length of from about 15 cm to about 30 cm. The central void in the outer absorbent member may have a transverse width of from about 2 cm to about 6 cm, more specifically from about 3 cm to about 5 cm, and can have a length of from about 4 cm to about 30 cm, more specifically from about 6 cm to about 20 cm, resulting in a desirable distance from the longitudinal edge of the central absorbent member to the nearest outer longitudinal edge of the outer absorbent member (which can also be the edge width of the outer absorbent member, assuming no significant gap between the outer absorbent member and the central absorbent member) of from about 0.3 cm to about 2.5 cm, and more specifically from about 0.5 cm to about 2 cm, and more specifically still from about 0.7 cm to about 1.5 cm. Appropriately larger dimensions would be desirable for diapers and many other absorbent articles. For example, the central absorbent member may be from about 4 cm to about 10 cm in width in a diaper.

Basis weights of the components of the absorbent core can be adjusted and optimized for particular purposes over a wide range. Generally, it is desirable that the basis weight of the central absorbent member be greater than the outer absorbent member because the central absorbent member is intended to contain the primary source of absorbent material for the article, and the outer absorbent member can desirably function as a secondary source of absorbent material when the absorbent capacity of the central absorbent member is exceeded. Thus, the basis weight of the central absorbent member can range, for example, from about 100 grams per square meter (gsm) to about 2500 gsm, more specifically from about 200 gsm to about 1200 gsm, and more specifically still from about 300 gsm to about 800 gsm. The basis weight of the outer absorbent member (or, in some embodiments, of the outer shaping member) can range from about 100 gsm to about 2000 gsm, more specifically from about 200 gsm to about 1000 gsm, and most specifically from about 200 gsm to about 600 gsm.

The absorbent capacity of either the central absorbent member or the outer absorbent member can be optimized for the intended use of the article. In diapers, the absorbent capacity of the central absorbent member generally should be greater than 60 ml and can be about 300 ml or less of fluid, more specifically about 200 ml or less, more specifically still about 150 ml or less, with exemplary ranges of from about 80 ml to about 250 ml or from about 100 ml to about 300 ml. For some uses, such as in sanitary napkins, it is desirable that the absorbent capacity of the central absorbent member be at least 7 ml of fluid, specifically at least 10 ml, more specifically at least 16 ml, more specifically still at least 20 ml, and most specifically from about 15 ml to about 35 ml. In one embodiment, the absorbent capacity of the outer absorbent member is less than the absorbent capacity of the central absorbent member. For example, the outer absorbent member can have an absorbent capacity of about 5 to about 100% of the absorbent capacity of the central absorbent member, or the ratio can be about 90% or less, more specifically about 70% or less, and more specifically still about 30% or less. If desired, however, the outer absorbent member can have a higher absorbent capacity than the central absorbent member. In a less preferred embodiment, the outer absorbent member can have relatively little absorbent capacity, such as between about 1 ml to about 5 ml, but can primarily serve to provide a body-fitting shape to the article and to retain the central absorbent member and the wicking barrier. A ring of a flexible polyurethane foam would be an example of a less absorbent outer member that could serve such a purpose, even if it were a closed-cell foam, but it is preferred that the outer member be relatively absorbent to provide additional protection and absorbency to the article, in addition to optionally serving other functions such as body fit, comfort, integrity of the article, and wetness indication.

For ultrathin pads and other absorbent articles, it is desirable that the dry components of the absorbent core have a total thickness between about 2 mm and about 15 mm, and more specifically from about 3 mm to about 8 mm. When wetted, the central absorbent member and/or the outer absorbent member may increase substantially in thickness and void volume, such as a thickness increase of about 100% or greater, more specifically about 200% or greater, and more specifically still about 300% or greater. An example of a low-cost cellulosic component capable of increasing in thickness when wet is the absorbent material of Chen and Lindsay disclosed in commonly owned copending U.S. application Ser. No. 08/848,353, "Self-texturing Absorbent Structure and Absorbent Articles Made Therefrom," filed Apr. 21, 1997, or the densified structures of Hollenberg et al. in U.S. Pat. No. 5,779,860, "High-density Absorbent Structure," issued Jul. 14, 1998, both of which are herein incorporated by reference in their entireties. Regenerated cellulose sponge materials are also capable of expanding significantly when wet and can be used to enhance body fit and conformability by providing nonuniform basis weights that expand in a three-dimensional shape.

Either the central absorbent member or the outer absorbent member or both, or individual plies thereof, may be embossed for improved control over fluid wicking, if desired. The absorbent members likewise may be apertured, slitted for improved flexibility and body conformability, perf-embossed, calendered, or pleated. A central slit in the central absorbent member can be especially useful in products for feminine care, for the slit can result in deformation of the article in use that enhances contact with the body for better absorption of menses.

Other components may be combined with the cellulosic materials of the absorbent core or added as separate layers or portions of the article. Such other components include odor absorbing components such as baking soda, talc powder, cyclodextrin, ethylenediamine tetra-acetic acid, zeolites, activated silica, and activated carbon granules, fabrics or fibers; superabsorbent particles and fibers; antimicrobial agents including the silver-loaded zeolites of BF Technologies, located in Beverly, Mass., sold under the trademark HEALTHSHIELD™, as well as triclosan products, chitosan or chitin derivatives; polycarboxylic acids; encapsulated perfumes; emollients such as lanolin; or skin wellness agents such as aloe vera extract or vitamin E. Thermoplastic binder fibers may be added, with or without subsequent heat treatment for improved stability. Foam layers, foam shape-defining components, or foam particles may also be present. Plastic inserts to define shape or maintain integrity may also be used.

The central absorbent member generally can be of any shape such as circular, elliptical, rectangular, triangular, polygonal, dog-bone shaped, hourglass shaped, or diamond shaped, and is inset or inserted into a depression or void in an outer absorbent member having either a width or length, or both, greater than the respective width or length of the central absorbent member. The central absorbent member desirably has a longitudinal length greater than the width, with the length extending desirably across 30% or more of the length of the article, more specifically 50% or more, more specifically still 75% or more, and most specifically 90% or more of the length of the absorbent article, including 100% of the length of said article. The maximum width of the central absorbent member can be 100% of the width of the absorbent article but desirably is no more than about 90%, more specifically no more than about 75%, and more specifically still no more than about 60% of the width of the absorbent article.

The central depression or void of the outer absorbent member is desirably a region of reduced basis weight relative to the other regions of the outer absorbent member, but can also be a region which has been compressed in thickness substantially such that a depression is defined which can receive an absorbent insert to serve as a central absorbent member.

The center strip or strips that replace a portion of the surrounding outer absorbent member, or are inset into a depression or void in the outer absorbent member, can offer a z-direction gradient in material properties to achieve desired objectives in fluid transport, dryness, odor control, and/or fluid retention. For example, the central absorbent material may be two or more strips of cellulosic material, such as an upper strip of an airlaid or wetlaid material having a first density or mean pore size and a second lower strip of an airlaid or wetlaid material having a second density or mean pore size. Desirably, the mean pore size of the lower strip is smaller than that of the upper strip such that capillary forces will preferentially remove fluid from the upper strip into the lower strip for an improved dry feel. In one embodiment, the lower strip is a wet laid material such as a through-dried tissue having a density greater than 0.1 grams per cubic centimeter (g/cc) and suitably greater than about 0.15 g/cc, while the upper strip is an air laid material having a density less than about 0.15 g/cc and specifically less than about 0.1 g/cc. The combined basis weight of the central absorbent strip or strips can be greater than, less than, or about the same as that of the surrounding outer absorbent member, with characteristic values between about 50 and 500 gsm, specifically between about 100 and 400 gsm, and more specifically between about 150 and 300 gsm. Desirably, though, the central absorbent member has a substantially higher basis weight than the outer absorbent member for better efficiency in material usage.

If two or more strips are present in the central absorbent member, the basis weight of the lower strip can be about the same, less than, or greater than that of the upper strip. Two or three layers with differing wicking capacities can be used, as disclosed in U.S. Pat. No. 5,401,267, issued Mar. 28, 1995 to Couture-Dorschner et al., herein incorporated by reference in its entirety. The strips can be textured or three-dimensional webs, such as webs that have been wet-molded, dry-molded, embossed, apertured, co-apertured, folded, pleated, scored, perforated, perf-embossed, or spot bonded. For sanitary napkins, the central absorbent member desirably comprises at least one layer with a longitudinal slit therein to promote a W-shape fold in the pad when it is laterally compressed between the thighs of the user, such that the central absorbent member folds upward toward the body for improved fit and fluid intake. Alternatively, "brick slits" can be used wherein a series of short slits are spaced apart and staggered on two or more parallel longitudinal lines, or other slit patterns can be used, desirably with a predominantly longitudinal orientation. Score marks or embossing lines can also be applied to promote proper bending of the article in use.

The central inserts for placement in the central depression or void of the outer absorbent member can also be fully wrapped in nonwoven or other material, with the proviso that a portion of the wrap must serve to delay wicking relatively significantly more than does the horizontal surface of the wrapped insert to reduce edge wicking. In many embodiments, the sides of the wrapped insert desirably are substantially impermeable. For some absorbent articles, the central inserts desirably rise above the plane of the surrounding outer absorbent member to provide an elevated central region for improved body fit. The stiffness of elements in the central absorbent member can be adjusted relative to the outer absorbent member such that good body fit is maintained in use and that undesirable bunching of the article is prevented. Densified zones for improved bending can be included in the present invention, as well as wings, tabs, extensible components, cuffs or flaps.

The outer absorbent member can comprise the same absorbent materials as the central absorbent member or other absorbent materials known in the art, with cellulosic fibers being desirable for their low cost, good visual and tactile properties, good absorbent capacity, and biodegradability. Desirably, the outer absorbent member is fibrous with fibers that are essentially noncontiguous with the central absorbent member (i.e., the central absorbent member and the outer absorbent member do not share fibers that join the two members). The outer absorbent member desirably has a lower basis weight than the central absorbent member but still provides several important functions. Generally, it is intended that the outer absorbent member remain unwetted except in cases of heavy flow. The unwetted structure of the outer absorbent member does not collapse but maintains high integrity in the dry state, which helps maintain the shape and fit of the article. When it does become wetted, the outer absorbent member can serve as an indicator that the absorbent article needs to be replaced. The indicator function can be visual (e.g., the user sees that flow has reached the outer absorbent member, indicating the need to replace the article), tactile (e.g., fluid reaching the outer absorbent member can react with an agent that produces cold or heat in the outer absorbent member, or the decreased stiffness of the outer absorbent member when wetted may result in a noticeable change in the feel of the article when compressed by the user's legs), olfactory (e.g., microencapsulated perfumes in the outer absorbent member may be released upon wetting to provide a pleasant smell as a cue for changing the article), or auditory (dry particles may swell and emit a crackling sound when wetted, analogous to puffed rice cereal, or a small electronic circuit may emit a beep when conductive fluid contacts one or more electrodes).

In one embodiment, the outer absorbent member is replaced with an outer shaping member whose primary function is not to absorb fluid but to provide shape and stability to the article as it cradles or holds in place the wicking barrier and the central absorbent member. These functions are desirably achieved with an absorbent material such as cellulose fibers or a hydrophilic foam, but when the absorbent capacity of the central absorbent member is adequate, the outer absorbent member will generally not be needed for its liquid absorbent capacity and thus can be replaced with a material such as a less absorbent polymeric foam (e.g., foam rubber) for comfort, fit, shape, and product integrity.

The wicking barrier can comprise any barrier material between two segments of material that reduces lateral wicking of fluid from the central absorbent member to the surrounding outer absorbent member. The barrier spans a finite vertical distance in the absorbent article, such as about 2 mm or greater, specifically about 3 mm or greater, more specifically about 5 mm or greater, and most specifically from about 4 mm to about 15 mm. The barrier material can be a polymeric film or plastic film; a nonwoven web; a layer of rubber, silicone, or other non-absorbent materials; or a less pervious paper sheet including, for example, glassine, wax paper, impregnated papers, paper-polymer composites, densified tissue, tissue containing internal sizing to render it less hydrophilic or tissue treated with hydrophobic matter such as wax, silicone, thermoplastic material, or polyolefins. Flexible hydrophobic foams may also be used, such as a closed-cell polyurethane foam or a silicone foam. A low density hydrophobic web such as a bonded carded web of a polyolefin (such as materials commonly used for surge layers in diapers, but without surfactants or other hydrophilic treatments) can also be used, including the transfer delay barrier materials disclosed in the commonly owned U.S. patent application Ser. No. 60/079,657, "An Absorbent System for Personal Care Products Having Controlled Placement of Visco-Elastic Fluids" by A. S. Burnes et al., herein incorporated by reference in its entirety. Desirably, the barrier material will have a porosity less than 90%, specifically less than 50%, more specifically less than 30%, and more specifically the barrier material will be substantially nonporous or substantially impermeable, though a small number of apertures or small openings can be provided in selected portions of the barrier material to prevent oversaturation of the central absorbent member. With apertures added, it is still desirable that the average open area of the barrier material be less than 20% and more specifically less than about 10%. Suitably, the thickness of the wicking barrier can be about 5 mm or less, specifically about 2 mm or less, more specifically about 1 mm or less, and most specifically about 0.5 mm or less. In some cases, such as when a barrier material in the form of a flexible polymer sheet is used, including a polypropylene or polyethylene web, the barrier material can have a thickness of about 0.2 mm or less, more specifically about 0.1 mm or less, and most specifically about 0.08 mm or less, with an exemplary range of from about 0.02 mm to about 0.3 mm.

The barrier material can also comprise hydrophobic matter that is used to impregnate a portion of the outer absorbent member or a portion of the central absorbent member to reduce lateral wicking. Such hydrophobic matter can include adhesives and particularly hot melt adhesives added to the absorbent article while molten; wax; pastes or emulsions comprising waxes; silicone-based fluids, gels, pastes, or caulk; phenolic resins or other resins which are cured after impregnating the fibrous material of the central absorbent member or outer absorbent member; polyolefins or other plastic or hydrophobic material added as powder, particularly sintered powder, or held in place by adhesives, or by thermal bonding. In addition to the impregnating material, which helps prevent lateral fluid flow in the article, it is also desirable that there be a distinct break, gap, or slit between the central absorbent member and the outer absorbent member in the crotch region to further impede fluid communication, especially by removing or severing fibrous pathways between the central absorbent member and the outer absorbent member.

Desirably, the Intrinsic Absorbent Capacity of the barrier material is about 1 or less, more specifically less than about 0.5, more specifically still less than about 0.3, and most specifically less than about 0.1.

The barrier material can be placed along a portion of the perimeter of a central absorbent member to reduce or prevent wicking to the surrounding outer absorbent member. In such an embodiment, the wicking barrier desirably can comprise a thin layer of a hydrophobic material such as a polymeric film, a nonwoven web, a thermoplastic material, a layer of hot melt adhesive, or a flexible material such as a wax impregnated in the fibers adjacent the perimeter of the central absorbent member. When the wicking barrier is a polymeric film or nonwoven web, it desirably has radial dimensions when set in place slightly greater than the radial dimensions of the central absorbent member such that a strip of the material rests on the surface of the absorbent core to define a visible barrier along at least a portion of the perimeter of the central absorbent member.

The barrier can also comprise material from the backsheet of the absorbent article which is embossed, deformed, pleated, or stretched so as to rise above the conventional plane of the backsheet into the barrier zone between the central absorbent member and the surrounding absorbent material. Likewise, the wicking barrier can comprise material from the topsheet that penetrates into the absorbent core to separate the central absorbent member from the outer absorbent member or from an outer shaping member, particularly when the topsheet material is rendered impervious or hydrophobic by chemical treatment, impregnation of adhesive or thermoplastic material, or heat sealing.

The barrier material can also be an adhesive such as a hot melt, a fluoropolymer, a wax, latex, or other known hydrophobic materials which are added or deposited on at least one side and preferably both longitudinal sides of a central absorbent member to hinder lateral wicking, particularly wicking normal to the longitudinal direction of the absorbent article.

In one embodiment, the wicking barrier is integral or unitary with the backsheet, and comprises an extended portion of the backsheet which wraps a portion of the outer absorbent member and penetrates into the absorbent core, separating the outer absorbent member from the central absorbent member and desirably becoming attached to itself under the central absorbent member. In one embodiment, the horizontal component of the wicking barrier comprises a portion of the backsheet that is wrapped around the outer absorbent member. The vertical component of the backsheet may also comprise a portion of the backsheet that is wrapped around the outer absorbent member.

In a related embodiment, the effect of the wicking barrier is augmented with a moat, wherein a strip or ring of finite thickness essentially void of absorbent material separates two or more zones of absorbent material to reduce lateral wicking from one zone to the other, and optionally to provide a channel or channels to redirect macroscopic flow of fluid acting under the influence of gravity, inertia, or hydraulic pressure. For example, a central absorbent member of a diaper with an hourglass or rectangular shape can be physically separated from the surrounding outer absorbent member by a moat-like void region having a desirable gap width of from about 0.3 mm to about 15 mm, more specifically at least about 1 mm. The moat-like void region can form a concentric ring around the central absorbent member or can isolate the central absorbent member from the outer absorbent member by one or more strait or curved elongated separation zones.

In another embodiment, the vertical component of the wicking barrier can be substantially above the outer absorbent member, covering a portion of the longitudinal sides of a central absorbent member that resides above the outer absorbent member. In one such embodiment, for example, the outer absorbent member may comprise a substantially flat layer of absorbent material having a first width. A central absorbent member having a second width less than the first width resides above the outer absorbent member, with a layer of wicking barrier material sandwiched therebetween, the wicking barrier material having a width intermediate the first and second widths. A portion of the wicking barrier rises vertically along a portion of the longitudinal sides of the central absorbent member to prevent lateral flow therefrom, and may optionally further wrap a portion of the upper surface of the central absorbent member to form a more complete barrier to hinder fluid communication from the sides of the central absorbent member to the underlying outer absorbent member (or an underlying outer shaping member).

The central absorbent member can comprise the same material as the surrounding outer absorbent member or can be a multi-ply assembly of wet laid tissue or a mixture of wet laid and air laid components, desirably also comprising superabsorbent material which may be laminated in pockets, adhesively attached to the plies, embedded in an airlaid layer, or present as fibers or films.

Optionally, a surge layer can be disposed between the topsheet and the absorbent core, specifically above the central absorbent member, to enhance intake of fluid, particularly urine and particularly in absorbent articles intended for urine management such as diapers, training pants, or incontinence pads. The surge layer is typically a non-absorbent or marginally absorbent (e.g., having an Intrinsic Absorbent Capacity less than about 0.9 and specifically less than about 0.3) high-loft nonwoven web, such as a bonded carded web, of synthetic materials such as polyethylene or polypropylene, which does not retain liquid but helps to distribute it into the underlying absorbent core. Basis weights for such a surge layer are desirably between about 15 gsm and about 100 gsm, with porosities above about 96%. Exemplary surge layers are described in U.S. Pat. No. 5,562,650, issued Oct. 8, 1996 to Everett et al.; U.S. Pat. No. 5,527,300, issued Jun. 18, 1996 to Sauer; U.S. Pat. No. 5,490,846, issued Feb. 13, 1996 to Ellis et al.; and U.S. Pat. No. 5,429,629, issued Jul. 4, 1995 to Latimer; all of which are herein incorporated by reference in their entireties.

In one embodiment, an absorbent article according to the present invention can be created by placing a central absorbent strip into a depression in an outer absorbent member wherein a substantially vertical barrier material is at the edges of the central absorbent strip to reduce lateral flow. For example, a depression or stamped out region can be formed in an absorbent pad and the depression or stamped out region is lined with a meltblown barrier layer, a polymeric film, or other barrier material, whereafter a central absorbent strip is placed in the depression or stamped out region to serve as a central absorbent member having barrier to lateral leakage toward the surrounding outer absorbent member. The barrier material may permit z-direction transport toward the outer absorbent member more readily than it permits lateral flow, as can be achieved, for example, by providing perforation in the middle of an impervious film whose unapertured sides block lateral flow into the surrounding outer absorbent member.

Related embodiments can be produced by simply stamping out the region of the absorbent core that lies underneath the air laid strips (thus forming an outer absorbent member with a void therein) and placing a meltblown barrier layer, which is slightly wider than the airlaid strips, over the resulting hole such that most of the meltblown barrier layer is in contact with the backsheet and a recess is defined in the outer absorbent member. The air laid strips, optionally with other absorbent materials, are then pressed into the recess in the outer absorbent member. The meltblown barrier layer deforms around the air laid strips to form a substantially vertical barrier between the strips and the surrounding core. Excess width of the meltblown barrier layer will result in a band of meltblown material around the center strips, which may offer a visual cue (especially if the meltblown is colored) of a protective ring around the central absorbent area. The band can form a complete ring around the central absorbent zone, or can form longitudinal bands separating the sides of the article from the central target region.

Numerous other embodiments of the present invention are possible wherein a web, film, or sheet of limited or relatively reduced fluid permeability serves as a barrier for flow of fluid from a central absorbent member to a surrounding absorbent member. The barrier need not be completely liquid impervious, but can offer substantial flow resistance by virtue of pore size or flow path tortuosity, or can offer capillary resistance by virtue of surface chemistry, such that wicking of fluid from the central absorbent member is substantially reduced in rate relative to a similar absorbent article without the barrier material. For example, the barrier material can be a polymeric apertured film or nonwoven web such as a meltblown web, which can permit fluid flow under gradients of hydraulic pressure but which limits spontaneous wicking out of the central absorbent member. Importantly, the barrier material provides a barrier effect across a finite vertical distance in the absorbent article such that the barrier material acts as a barrier for lateral flow rather than solely as a barrier for vertical flow from one superposed layer to another.

In embodiments using an apertured film for the wicking barrier, the film should be oriented to hinder flow from the central absorbent member toward the outer absorbent member. Many apertured films provide flow directionality, wherein flow passes through the film most easily when fluid is deposited on one side of the film. For example, many films have tapered or conical apertures with large openings on one side and narrow openings on the other, wherein fluid on the side with the large openings passes readily through the film, whereas fluid on the side with the narrow openings is more likely to be hindered from passing through the film. When a film provides such directionality, it is desirable that the side most likely to hinder fluid flow be placed toward the central absorbent member. In this manner, wicking flow from the central absorbent member to the outer absorbent member may be delayed until the central absorbent member is substantially saturated.

Leakage prevention in sanitary napkins and related absorbent articles for feminine care pose particular problems due to the wide range of forces the article will experience in actual use. In particular, transverse compression of the pad by the legs of the user can result in lateral "bunching" with a wide variety of possible deformations in the product. While the use of vertical barriers between absorbent zones according to the present invention yields excellent center fill results and leakage reduction in lab tests and in theory, the dynamic conditions of actual use can sometimes interfere with the effectiveness of the vertical barriers between absorbent zones. Most importantly, if transverse compression or bunching of the absorbent article causes the edges of the outer absorbent member to fold into contact with the central absorbent member, then wicking contact can be established between the two zones in spite of the vertical wicking barrier, resulting in fluid transport to the outer absorbent member and possible leakage out the side of the article. To maintain a center fill strategy in sanitary napkins under the dynamic conditions of actual product use, it is desirable to implement strategies to prevent bypassing of the wicking barrier and to maintain isolation of the absorbent members.

The presence of a horizontal component or ledge on the body surface of the absorbent material attached to the vertical component of the wicking barrier is one useful means of preventing contact of the central absorbent member with the outer absorbent member during transverse compression. In one embodiment, the ledge has increased width in the crotch region of the article such that the horizontal component of the wicking barrier along the transverse axis of the article covers about 30% or more, specifically about 50% or more and most specifically about 80% or more of the surface of the outer absorbent member along the transverse axis of the article, with essentially 100% coverage in the crotch region being desirable in some embodiments. In some embodiments, it is desirable that the ledge be relatively narrow (e.g., less than 4 mm or less than 3 mm) except in the crotch region, where the ledge can expand to cover a significant portion (about 30% or more, about 50% or more, or about 80% or more) of the distance between the central absorbent member and the longitudinal edges of the outer absorbent member, such that complete folding of the edges of the article into contact with the central absorbent member will not result in wicking contact between the absorbent material of the outer absorbent member with that of the central absorbent member.

Other means can also be employed to prevent wicking contact during bunching of the absorbent article. The topsheet or cover itself can play an important role. In one embodiment, the cover can be rendered substantially impervious over the outer absorbent member in the crotch region such that wicking between absorbent members is impeded even when the outer absorbent member is folded into contact with the central absorbent member. An apertured film, for example, can simply be made free of apertures in regions where imperviousness is desired such as over the outer absorbent member in the crotch region or over the entire outer absorbent member. To selectively render an otherwise pervious nonwoven material impervious, it can be coated or sprayed with water repellent materials, including those which form a film or can occlude openings. Waxes, acrylic coating materials, and silicone compounds that form gels or films, for example, may be used.

In one embodiment, the topsheet is provided with loops, folds or pleats on the surface to provide regions that are elevated above the absorbent material of the absorbent core, no longer in direct contact with the absorbent material of the core and desirably running in a longitudinal direction, as disclosed by U. Hagrud et al. in PCT publication WO 98/24389, "Absorbent Article with Improved Leakage Security," published Jun. 11, 1998. Hagrud et al. disclose air-filled material folds on the surface of an absorbent article having a longitudinal direction which serve as barriers to fluid flow on the surface of the article and which are said to provide improved comfort to the wearer. The folds can be provided by an impervious fabric applied to the edges of the article or can be formed from the liquid-pervious cover material. The material used to make the folds must be adhered or otherwise attached to an underlying layer, such as a tissue or airlaid strip, at a number of discrete points or along parallel discrete lines or bands between which the folds are formed from material having a length greater than the distance between adjoining points or bands of contact. Such loops, folds or pleats of material, for purposes of the present invention, can be adapted to also help prevent wicking contact of the central absorbent member with the outer absorbent member during conditions of dynamic use.

Desirably, the loops, pleats, or folds are given increased bulk and body by bunching a larger quantity of material together than is necessary to make a single loop. More particularly, it is desirable to have multiple folds or a spiral winding pattern to take up additional material in the fold, pleat, or loop, to increase the body thereof and provide more wet stable resistance to fluid leakage. Thus, the cover material can be wound with multiple turns, or provided with multiple folds and pleats within a small area to increase the bulk of the section, and then stabilized or sealed into place with heat, ultrasound, mechanical pressure, or application of adhesive. The loop or fold can also be provided with additional matter therein to increase its thickness and flow restraining or comfort properties. For example, a length of a fibrous tow or yarn with a diameter of about 0.5 to about 3 mm may be enclosed in a loop or fold of a nonwoven topsheet along the perimeter of the central absorbent member or superposed over the outer absorbent member to help provide a gasketing function against the body of the wearer, particularly if the loop or fold is treated to be impervious or hydrophobic. Further, the loop or fold filled with fibrous material can better conform to the body and provide a cushiony feel for improved comfort, while serving as a flow controlling agent that prevent wicking contact between the central absorbent member and the outer absorbent member.

In one embodiment, the cover or topsheet of the article is provided with an air-filled or hydrophobic fiber-filled loop or fold of material substantially centered along or running over the boundary between the outer absorbent member and the central absorbent member, particularly in the crotch region. Desirably, the wicking barrier in the boundary also has a horizontal component serving as a ledge residing over a portion of the outer absorbent member, and the cover is adhesively attached just outside the ledge toward the nearest longitudinal edge of the article and is also adhesively attached a distance inside the central absorbent member to define a loop of unattached material substantially over the boundary between the two segregated members of absorbent material. The unattached portion of the fold or pleat over the boundary can buckle away from the boundary as the outer absorbent member is folded toward the central absorbent member with the boundary zone acting approximately as a hinge or hinge region. The outwardly buckled unattached material of the cover provides two additional layers of cover material which can interfere with wicking between the two segregated members, extending the protection offered by the ledge to a greater distance to more fully interfere with wicking to the edges even when the article is severely bunched or transversely compressed during use.

Additionally or alternatively, a loop of material over the central absorbent member slightly inside the boundary can act to help prevent wicking contact of the outer absorbent member with the central absorbent member when the two members are folded toward each other.

The loops, folds, or pleats in the cover material or other material added to the cover to form pleats can be treated to be hydrophobic or impervious in the regions not in contact with the absorbent core to further enhance the ability of the loops, folds, or pleats to prevent undesired fluid transport to the outer absorbent member.

Means can also be applied to reduce the tendency of a pad or sanitary napkin to bunch or fold over onto itself during transverse compression. Wings and tabs that fold over the edge of undergarments are useful in helping to maintain the shape of a pad and can reduce undesirable bunching of the article. Even without tabs or wings, related advantages can be obtained with proper placement of adhesives on the backsheet of the absorbent article. In many commercial articles, the articles are provided with adhesive strips on the backsheet protected with a layer of release paper that can be removed to permit adhesive attachment of the article to the user's panties. The adhesive strips or zones are typically near the center of the article, permitting the use of narrow strips of release paper. However, placement of the adhesive strips nearer to the edge of the pad or napkin can be more effective in holding the edges of the article in place and reducing the tendency of the article to fold over on itself, and particularly in preventing the outer absorbent member from contacting the central absorbent member. Wider release paper may be needed, or two narrow strips of release paper may be used to cover adhesive strips on the longitudinal sides of the article, but the improved placement and stability of the article attached to the edges of the user's undergarments is believed to offer significant performance advantages.

Preshaping of a pad can be useful, including the means disclosed in U.S. Pat. No. 5,545,156, issued Aug. 13, 1996 to DiPalma et al., herein incorporated by reference in its entirety.

It is also desirable to provide the absorbent core of the article with cuts, embossments, or score lines to direct the manner in which the article bends or buckles when in use such that good body fit is achieved. Examples of such an approach are disclosed in U.S. Pat. No. 5,514,104, issued May. 7, 1996 to Cole et al., herein incorporated by reference in its entirety. Embossments in the central absorbent member are desirable to promote a fold along the longitudinal centerline in sanitary napkins. Desirably, the embossments (densified areas) should rise toward the body rather than descend away from the body to encourage the central absorbent member to fold up toward the body when compressed from the sides in use.

One embodiment of the central absorbent member of the present invention comprises multiple layers of barrier material sandwiched between regions of absorbent material to form a composite structure wherein multiple barrier regions interfere with radial or lateral wicking (i.e., with horizontal fluid transport) either by imposing impervious barriers or by directing flow in tortuous pathways. As such, in one embodiment, the barrier material of a composite structure may be a wicking barrier as previously discussed herein. The composite structure forms a primary or central absorbent member which need not be surrounded by additional absorbent material but which may comprise substantially all of or a major portion of the absorbent material in an absorbent article, or can comprise an entire layer of absorbent material in such an article. Desirably, the composite structure is a concentric absorbent structure wherein multiple layers of vertically oriented barrier material alternate between multiple layers of absorbent material either in complete loops such as circles or ellipses, or in a spiral structure. The spiral embodiment of the concentric absorbent structure is analogous to a thinly sliced portion of the "jelly roll" of cake and fruit filling that is well known among bakers and confectioners in the United States and Switzerland, wherein a sheet of flexible cake is coated with the filling and then rolled into a spiral wound structure with concentric bands of cake and filling. The similarity to a jelly roll is due to the concentric absorbent structure comprising a plurality of concentric bands of absorbent material, preferably spiral wound, with each band of absorbent material being adjacent to a thin barrier layer. The resulting composite structure with multiple barrier layers intrinsically offers the highest permeability in the z-direction (the thickness direction of the structure, also the direction substantially parallel to the plane of the wound barrier material), while permeability in the radial direction is relatively lower due in part to the orientation of fibers in the concentric bands and due to the presence of wicking barrier material between the bands to restrict flow. If the barrier material is impermeable, which it can be, then the barriers define a labyrinth-like spiral path for fluid being wicked from central regions of the composite structure to outer regions of the structure. The labyrinth-like pathway restricts the radial expansion of fluid and helps prevent leakage out of the sides of the article.

The multiple regions of barrier material provide multiple vertical barriers to isolate successive zones of the central absorbent member from the longitudinal sides of the article and from any outer absorbent member. The presence of such multiple barriers of generally hydrophobic material or non-absorbent material reduces the need for a horizontal component or ledge on the surface of the absorbent core, though the wicking barrier can still desirably be provided with a horizontal component for improved protection against leakage or surface smearing. Desirably, a horizontal component or ledge is provided only on the radially outermost section of the wicking barriers, and particularly at the boundary of the central absorbent member and the outer absorbent member. Thus, the wicking barrier between the composite central absorbent member and the outer absorbent member can be provided with both a vertical component and a horizontal component, the latter forming a ledge on the body-side surface of the absorbent core.

A spiral-wound absorbent structure can be formed from any layer of absorbent material placed adjacent to a layer of barrier material, followed by rolling of the absorbent material and barrier material about a rolling axis (e.g., rolled in a specified direction) to form a parent roll, whereupon the parent roll is sliced substantially normal to the rolling axis to give a disk-like layer having a spiral characteristic with alternating concentric bands of absorbent material and barrier material similar to a jelly roll.

The absorbent material of concentric absorbent structures of the present invention can be any of the materials previously mentioned for use in the absorbent core or other materials known by those skilled in the art. The absorbent material can comprise one of more layers that can be overlapped. Alternatively, two or more layers of absorbent material can be butted or spliced prior to forming the concentric absorbent structure such that the absorbent material varies in composition or properties from the center toward the outer edges of the concentric absorbent structure. Likewise, one or more layers of absorbent material may be treated to have spatial gradients in properties such as density, contact angle or wettability, superabsorbent content, or the content of other additives, such that material properties in the absorbent vary with position in the concentric absorbent structure. Further, non-layered materials such as lengths of yarn, bands of absorbent tow, or other materials may be combined with the absorbent material at various locations as it is wound and incorporated into the concentric absorbent structure.

When a molded, three-dimensional sheet is used to form the concentric absorbent structure of the present invention, and particularly uncreped through-dried tissues, substantial flow channels exist for enhanced fluid flow in the thickness direction, thus permitting rapid intake of fluid from urine insults or menses gushes, while also providing absorbency and fluid retention capacity due to the absorbency of the tissue itself.

The concentric absorbent structure can be formed by rolling absorbent material and barrier material around itself, or can be wrapped around a central absorbent member. For example, a roll of cotton material, fluff pulp, or other absorbent material could serve as a central core around which additional absorbent material and barrier material could be wrapped to form a concentric absorbent structure surrounding a first central absorbent member. In this manner, the concentric absorbent structure could serve as an extension of the first concentric absorbent structure, thus being a second central absorbent member which, together with the absorbent central core, forms a composite central absorbent member, or the concentric absorbent structure could comprise an outer absorbent member around the central absorbent member.

The barrier material is a thin layer of material such as a polymeric film or hydrophobic matter which can serve to reduce liquid transport from one absorbent layer to another, as can a polymer film or hydrophobic material placed on a surface of the absorbent material before it is wound into a parent roll. Desirably, the barrier material is flexible to permit winding with the adjacent absorbent material without significant damage to the barrier material. The structure is useful as an intake component in an absorbent article, or as a portion of a primary absorbent core, or as a multifunctional component offering both intake and fluid retention capabilities. The structure is especially well suited for enhancing transport of fluids in the thickness direction (z-direction) of the structure and reducing fluid leakage to the edges of the absorbent article.

The barrier material may be impervious or may be permeable to liquid or, in one embodiment, has an in-plane gradient in permeability and/or porosity such that the highest permeability or porosity is found in the center portions of the concentric absorbent structure, with the permeability or porosity decreasing with radial distance from the center of the absorbent structure such that lateral flow is most strongly hindered as the edges of the absorbent structure are approached, thus reducing the tendency for wetted absorbent articles to leak toward the edges of the article.

In one embodiment, the barrier material serves to reduce friction between adjacent layers of absorbent material such that the coils or layers of the spiral-like material can move relative to one another in the z-direction of the absorbent structure, resulting, for example, in a telescoping type of action. The possibility for out-of-plane motion of the bands in the concentric absorbent structure permits improved body conformability and reduced stiffness. The barrier material itself can comprise multiple plies.

In one embodiment, the barrier material is a web or film having a first surface that is fixedly attached by adhesive or thermal bonding to a first surface of a tissue web prior to forming a parent roll, and further having a small quantity of adhesive material at discrete and widely separated points or lines on the opposing second surface of the barrier material, such that the resulting concentric absorbent structure can still flex and exhibit a degree of telescoping motion, but wherein the degree of telescoping or z-direction deformation is restrained by the discrete spots of bonding between the second surface of the barrier material and the adjacent second surface of the tissue web in the wound structure.

For example, a polymer film having a basis weight less than 10 grams per square meter (gsm) and preferably less than 3 gsm may be adhesively bonded on its lower surface with a uniform application of adhesive to the upper surface of an underlying through-dried tissue web, desirably uncreped, having a basis weight of about 20 gsm to about 100 gsm, preferably from about 35 gsm to about 60 gsm, and having a bulk at 0.344 kPa (0.05 pounds per square inch) measured by a 7.62-centimeter (3-inch) diameter platen of from about 6 cc/g to about 40 cc/g, and specifically from about 10 cc/g to about 25 cc/g. The upper surface of the polymer film may be printed with discrete lines of contact adhesive running parallel to the axis of winding of the polymer-tissue composite. The thin lines of contact adhesive may be spaced apart by about 0.5 cm to about 2.5 cm. The wound structure, when sliced, yields concentric absorbent structures wherein the barrier material is fixedly attached to one surface of the wound tissue web and loosely attached by the spaced apart adhesive lines to small portions of the opposing surface of the tissue web, still permitting some z-direction deformation for improved body conformability but restraining the telescoping motion to maintain high integrity of the concentric absorbent structure under shear and compressive stresses.

In another embodiment, the barrier material may comprise two plies of polymeric material with low friction between the two. Such a structure could be formed by laminating a polymeric web or adding other hydrophobic material to both sides of a tissue ply or both the upper and lower surfaces of a multi-ply tissue or cellulosic structure and then rolling or folding the composite to form a parent roll from which the concentric absorbent structure may be sliced. Likewise, simply two layers of a polymeric web could be laid adjacent a cellulosic structure and then rolled or folded to create the parent roll in whatever shape is desired. In this manner, improved mobility of the bands may be achieved by virtue of the low friction between the adjacent barrier material plies. Alternatively, a second ply or layer of barrier material may be added to only selected regions of an already present barrier material ply or layer in contact with tissue before formation of the parent roll to provide increased barrier function or mobility in selected zones of the concentric absorbent structure.

The shape of the concentric absorbent structure can be customized to correspond to the shape of the absorbent article. In one embodiment, the parent roll is formed by folding the tissue-barrier composite about a flat length of the composite to form non-circular parent roll which can then be compressed near the middle region to have an hourglass shape.

In addition to multilayered concentric absorbent structures, central absorbent members can comprise other absorbent structures with multiple vertical layers of barrier material. For example, a stack of multiple layers of absorbent material alternating with layers of barrier material can be assembled without rolling the structure and sliced normal to the plane of the individual layers to create a stratified composite having absorbent zones separate by wicking barriers. Such a stratified composite can be used as a central absorbent member, desirably lined with an additional layer of barrier material to reduce fluid escape from the ends of the layers of absorbent material.

The absorbent articles of the present invention can be combined with other functional materials internally (as by adding material into the absorbent material or on the barrier material) or externally (as by joining with additional layers), including but not limited to odor absorbents, activated carbon fibers and particles, baby powder, zeolites, perfumes, fire retardants, superabsorbent particles, nonwoven materials, plastic films or apertured films, extruded webs, closed cell foams, adhesive strips and tapes, tissue webs, electronic devices such as alarms indicating wetness or leakage and other wetness indicators, opacifiers, fillers, aerogels, sizing agents, antimicrobial agents, enzymes such as those capable of modifying and particularly reducing the viscosity of menses, ion exchange material, or enzyme inhibitors for prevention of damage to skin by digestive enzymes.

Skin comfort can be enhanced with the addition to the topsheet or body side surface of the absorbent core of other desirable materials such as aloe vera derivatives, lotions, emollients, silicone compounds, vitamin E, or derivatives of tallow and vegetable oils for softness and lubricity. Agents to reduce or prevent itching and skin redness can be included on the topsheet, backsheet, or absorbent members of the present invention, and can include the product sold as ENTELINE 2® by Presperse, Inc. (Piscataway, N.J.) which comprises butylene glycol, glycerin, and enteromorpha compressa extract. In general, additional layers, films, particulates, and chemicals can be added through the articles of the present invention.

Shape enhancing elements may be added to improve body fit, including contoured foams, regenerated cellulose structures that expand when wetted, air-filled pouches (including an air filled pouch formed by the wicking barrier and backsheet joined together beneath the central absorbent member), elasticized gathers and other elastic elements. Fluid control elements may be added such as cuffs, waist bands, leg gathers, or surge layers. Additional tissue layers may be added to restrain particulates (e.g., forming a multilayer laminate with superabsorbent particles), improve wicking, or provide integrity for the absorbent core. Adhesives such as construction adhesive or latex, including hydrophobic and hydrophilic varieties, may be used to attach adjoining layers and provide improved integrity and functionality. Fiber-foam composites can be included and can be a component of the outer absorbent member and/or the central absorbent member.

In one embodiment, the absorbent structure comprises a portion of activated carbon fibers to yield a fibrous structure having excellent odor absorbing abilities due to the high permeability of the structure to gas and due to the high fraction of accessible surface area of the fibers. The surface chemistry of the activated carbon fibers should be tailored for optimum absorption or wicking of the target fluids or gases of the fibrous structure and can be rendered hydrophilic. For example, acidic groups on the activated carbon fibers can be desirable for absorbing basic compounds comprising ammonium moieties. Acidic groups can be added by treating the fibers at elevated temperature in the presence of steam, carbon dioxide, or nitric acid. Basic groups, useful for absorbing acidic compounds such as hydrochloric acid, can be introduced by treatment with ammonia at elevated temperatures or by other treatments known in the art. Suitable fibers and fiber treatment methods include those disclosed in PCT patent application, "Coated Absorbent Fibers," by James Economy and Michael Daley of the University of Illinois, published as WO 96/38232, Dec. 5, 1996, and on the Univ. of Illinois Web site at "http://www.students.uiuc.edu/~ahall/activated carbon fabrics.html" as of January 1998, which discloses a variety of gas treatments at elevated temperature to activate the fibers and control the surface chemistry.

In embodiments comprising fibrous cellulosic absorbent materials, other additional additives and agents commonly known in the papermaking arts can be used. Wet strength agents, dry strength agents, crosslinking agents, surface chemistry modifiers, biocides or antimicrobials, or softeners can be present. When recycled fibers or other papermaking fibers are used, a quantity of filler materials such as calcium carbonate or titanium dioxide can be present. For absorbent articles intended to absorb body fluids, it is desirable that post-consumer recycled fibers not be used, though opacifiers, fillers, and other agents can be present or deliberately added. In most cases, virgin papermaking fibers are desirable for their mechanical properties and lack of contaminants. For example, odor-removing additives can be desirably present in the structures of the present invention, including activated carbon granules or fibers, activated silica particulates, ethylenediamine tetra-acetic acid, zeolites, polycarboxylic acids, anti-bacterial agents, talc powder, sodium bicarbonate, encapsulated perfumes, cyclodextrin, chitosan or chitin.

The absorbent core and particularly the absorbent material of the central absorbent member can comprise cellulosic fibers stabilized with a binder material. Likewise, the multiple layers that can be used in the outer absorbent member or the central absorbent member can be joined together with a binder material, or a binder material can attach the topsheet and/or the backsheet to the adjoining outer absorbent member or central absorbent member to improve pad integrity. The binder material may be water swellable or not water swellable. For best results in absorbent articles, the binder material desirably is substantially water insoluble, even when the binder material is water swellable. Preferably, the binder material provides not only good dry stability but also good wet stability and wet resiliency to the absorbent fibrous structure when wetted with liquid water. For applications where wet resiliency is needed to maintain high void volume even under compressive loads, the binder material desirably is not water swellable, is desirably water insoluble, and desirably has a binder wet strength to dry strength ratio of about 10% or greater, specifically about 20% or greater, more specifically about 40% or greater, and most specifically about 50% or greater. The same desirable ranges for binder wet strength to dry strength ratio apply to swellable binder materials as well.

For swellable binder materials, carboxymethylcellulose is a useful material capable of binding fibers and absorbing water. Aside from carboxymethylcellulose, polymers which are also suitable for use, particularly for freeze drying and other embodiments of the present invention, include a wide variety of anionic, cationic, and nonionic materials. Suitable polymers include polyacrylamides, polyvinyl alcohols, ethylene maleic anhydride copolymer, polyvinylethers, polyacrylic acids, polyvinylpyrrolidones, polyvinylmorpholines, polyamines, polyethyleneimines, polyacrylamides, polyquaternary ammoniums, natural based polysaccharide polymers such as carboxymethyl celluloses, carboxymethyl starches, hydroxypropyl celluloses, algins, alginates, carrageenans, acrylic grafted starches, acrylic grafted celluloses, chitin, and chitosan, and synthetic polypeptides such as polyaspartic acid, polyglutamic acid, polyasparagins, polyglutamines, polylysines, and polyarginines, as well as the salts, copolymers, and mixtures of any of the foregoing polymers. Polyglucan succinate or glutarate, for example, can also be used, particularly when cross-linked to form diester-crosslinks.

Other polymeric materials useful as binder materials include anionic and cationic latexes, wet strength agents, hydrocolloids, pectin, sodium carboxymethylcellulose, thrombin, collagen, amylose derivatives, algin, guar gum, or synthetic gums.

The absorbent core and particularly the central absorbent member fibrous structure can have gradients in material properties extending in the thickness direction or in directions in the plane of the article. Gradients or variations in basis weight and thickness can readily be provided, but other material properties such as fiber composition, pore size, or wettability can have gradients as well. For example, a planar absorbent member suitable for use in an absorbent article may have large pores and large open cells near a top surface, with cells that become progressively smaller near the opposing back surface, optionally terminating in a skin on the back surface which can be partially or substantially liquid impervious. Such a structure with a porosity gradient may be suitable for liquid intake on the top surface but can prevent liquid leakage from the back surface. Articles may be provided with gradients in hydrophilicity as well, with more hydrophilic binder material and fibers in one region (e.g., a top surface) than elsewhere (e.g., a back surface). Gradients may extend in the plane, giving, for example, an article with large cells or pores in a central target region but with more closed cells or smaller pores near the side edges of the absorbent fibrous structure to prevent lateral leakage of fluid.

For feminine care articles, tabs and wings can be added to the sides of the absorbent article. The wicking barrier can extend to the beginning of the tab or wing or beyond, though desirably the wicking barrier prevents lateral wicking of fluid into the region of the tab or wing. In one embodiment, the wicking barrier comprises a transverse section which extends laterally past the absorbent core to form a component of wings or tabs. Such a section can be an integral part of the wicking barrier or can be a second wicking barrier member in addition to a first wicking barrier member contained within the absorbent core.

The absorbent article can also be provided with densified zones or embossments that permit bending or folding of the article for improved fit or attachment to undergarments, or can be provided with elastic bands, cuffs, leg barriers, waist barriers, pockets for retaining feces, and other structural elements well known to those skilled in the art.

A variety of shaping elements can be added to control the folding or contours of the article in use, and to help maintain body fit. Elasticized regions and bands, for example, can be applied within the absorbent core or in longitudinal cuffs or along the backsheet to help direct curvature and contours of the article for improved fit.

Beneath the central absorbent member, it is possible to add soft, resilient or gas-filled shaping elements to raise the central absorbent member into contact with a body during use. For example, conformable foam or other material may be inserted underneath the central absorbent member, either in contact with the central absorbent member or between a layer of barrier material (i.e., the wicking barrier) and the backsheet. In one embodiment, the wicking barrier passes under the central absorbent member and contacts the backsheet, and is sealed against the backsheet around a periphery in a manner that encloses a volume of air to act as an air cushion beneath the central absorbent member for improved fit and comfort. Alternatively, a layer of material such as bubble wrap may be added to provide a cushion effect for comfort and fit.

As used herein, a material is said to be "absorbent" if it can retain an amount of water equal to at least 100% of its dry weight as measured by the test for Intrinsic Absorbent Capacity given below (i.e., the material has an Intrinsic Absorbent Capacity of at about 1 or greater). Desirably, the absorbent materials used in the absorbent members of the present invention have an Intrinsic Absorbent Capacity of about 2 or greater, more specifically about 4 or greater, more specifically still about 7 or greater, and more specifically still about 10 or greater, with exemplary ranges of from about 3 to about 30 or from about 4 to about 25 or from about 12 to about 40.

As used herein, "Intrinsic Absorbent Capacity" refers to the amount of water that a saturated sample can hold relative to the dry weight of the sample and is reported as a dimensionless number (mass divided by mass). The test is performed according to Federal Government Specification UU-T-595b. It is made by cutting a 10.16 cm long by 10.16 cm wide (4 inch long by 4 inch wide) test sample, weighing it, and then saturating it with water for three minutes by soaking. The sample is then removed from the water and hung by one corner for 30 seconds to allow excess water to be drained off. The sample is then re-weighed, and the difference between the wet and dry weights is the water pickup of the sample expressed in grams per 10.16 cm long by 10.16 cm wide sample. The Intrinsic Absorbent Capacity value is obtained by dividing the total water pick-up by the dry weight of the sample. If the material lacks adequate integrity when wet to perform the test without sample disintegration, the test method may be modified to provide improved integrity to the sample without substantially modifying its absorbent properties. Specifically, the material may be reinforced with up to 6 lines of hot melt adhesive having a diameter of about 1 mm applied to the outer surface of the article to encircle the material with a water-resistant band. The hot melt should be applied to avoid penetration of the adhesive into the body of the material being tested. The corner on which the sample is hung in particular should be reinforced with external hot melt adhesive to increase integrity if the untreated sample cannot be hung for 30 seconds when wet.

As used herein, "absorbent capacity" refers to the total mass of water that a specified quantity of absorbent material can hold, and is simply the Intrinsic Absorbent Capacity multiplied by the dry mass of the absorbent material. Thus 10 g of material having an Intrinsic Absorbent Capacity of 5 has an absorbent capacity of 50 g (or about 50 ml of fluid).

"Absorbency Under Load" (AUL) is a measure of the liquid retention capacity of a material under a mechanical load. It is determined by a test which measures the amount in grams of an aqueous solution, containing 0.9 weight percent sodium chloride, a gram of a material can absorb in 1 hour under an applied load or restraining force of about 2 kPa (0.3 pound per square inch).

The AUL apparatus comprises a Demand Absorbency Tester (DAT) as described in U.S. Pat. No. 5,147,343, issued Sep. 15, 1992 to Kellenberger, herein incorporated by reference, which is similar to a GATS (Gravimetric Absorbency Test System), available from M/K Systems, Danners, Mass. A level porous plate is used having ports confined within a 2.5 cm. diameter area to provide liquid saline solution, 0.9 (w/w) % sodium chloride, delivered from a reservoir to the porous plate such that there is no hydraulic head (neither positive pressure nor suction) at the top of the porous plate. Thus, fluid can be absorbed into the absorbent without overcoming a significant capillary pressure barrier to move liquid out of the porous plate. Fluid absorbed from the plate is replaced with liquid from the reservoir, which resides on an electronic balance that measures the amount of liquid removed from the reservoir and absorbed into the absorbent. The sample on the porous plate resides within a section of 2.54 cm (one-inch) inside diameter thermoplastic tubing machined-out slightly to be sure of concentricity. Stainless steel wire cloth with 0.15 mm openings (100 mesh) is fused on the bottom of the cylinder to restrain the sample and any particulates therein. Care must be taken to maintain a flat smooth bottom and not distort the inside of the cylinder. A 4.4 g piston is made from 2.54 cm (one inch) diameter solid material (e.g., a clear plastic) and is machined to closely fit without binding in the cylinder. A standard 100 gm weight placed on the piston is used to provide a 21,000 dyne/sq.cm. (about 0.3 psi) restraining load which is commonly experienced in infant diapers. To carry out the test with a foam-like fibrous material or a foam, a material sample is cut into circular discs with a diameter slightly smaller than 2.54 cm (one inch) to freely fit within the sample tube. The sample mass should be from about 0.05 g to about 0.16 g.

This test is initiated by placing a 3 cm diameter GF/A glass filter paper onto the porous plate (the paper is sized to be larger than the inner diameter and smaller than the outer diameter of the cylinder), to insure good contact while eliminating evaporation over the ports of the DAT and then allowing saturation to occur. The material to be tested is placed on the wire cloth at the bottom of the AUL apparatus. The sample is then covered with a plastic spacer disc, weighing 4.4 grams and having a diameter of about 2.527 cm (0.995 inch), which serves to protect the sample from being disturbed during the test and also to uniformly apply a load on the entire sample. After carefully placing the piston and weight on the sample in the cylinder, the AUL apparatus is placed on the glass filter paper. The amount of fluid pick-up is monitored as a function of time either directly by hand, with a strip chart recorder or directly into a data acquisition system.

The amount of fluid pickup measured after one hour is the AUL value, expressed as grams of liquid per dry gram of the tested material.

The AUL of the materials of the present invention can be above 6 grams/gram, more specifically about 10 grams/gram or greater, still more specifically about grams/gram or greater, and most specifically about 25 grams/gram or greater, with an exemplary range of from about 9 to about 40 grams/gram. While high AUL values can be achieved without the additional use of superabsorbent material or swellable binder material, especially high values of AUL are possible through incorporation of superabsorbent material into the absorbent structure. Superabsorbent material can be incorporated as loose particulates, particles bound to the hydrophilic fibers, superabsorbent fibers, or as a component of the binder material or structuring composition.

As used herein, "Free Swell Capacity" (FS) is the result of a test which measures the amount in grams of an aqueous solution, containing 0.9 weight percent sodium chloride, that a gram of a material can absorb in 1 hour under negligible applied load. The test is done as described above for the AUL test, except that the 100 gm weight is not placed on the sample.

The Free Swell Capacity of the materials of the present invention can be above 8, more specifically above 10, more specifically above 20, and most specifically above 30 grams/gram.

As used herein, "Free Swell:AUL Ratio" is the ratio of Free Swell Capacity to AUL. It will generally be greater than one. The higher the value, the more sensitive the material is to compressive load, meaning that the sample is less able to maintain its potential pore volume and capillary suction potential under load. Desirably, the materials of the present invention have "Free Swell:AUL Ratio" of about 4 or less, more specifically about 2 or less, more specifically still about 1.5 or less, and more specifically about 1.3 or less, with an exemplary range of from about 1.2 to about 2.5.

"Water retention value" (WRV) is a measure that can be used to characterize some fibers useful for purposes of this invention. WRV is measured by dispersing 0.5 gram of fibers in deionized water, soaking overnight, then centrifuging the fibers in a 4.83 cm (1.9 inch) diameter tube with an 0.15 mm (100 mesh) screen at the bottom at 1000 gravities for 20 minutes. The samples are weighed, then dried at 105° C. for two hours and then weighed again. WRV is (wet weight-dry weight)/dry weight. Fibers useful for purposes of this invention can have a WRV of about 0.7 or greater, more specifically from about 1 to about 2. High yield pulp fibers typically have a WRV of about 1 or greater.

As used herein, a "flexible film" is one that a bulk material (e.g., the absorbent components of the article or materials used to provide shape in an outer shaping member) is considered "flexible" if a straight, TAPPI-conditioned (50 percent relative humidity at 22.7° C.) strip of the material 25 cm long with a cross-section of 1 cm×1 cm can be bent 180° around a 5-cm diameter rod without breaking and without requiring application of more than about 6 Newtons of force to the ends of the strip to cause the bending over a 3-second span of time. The same material is "shape retaining," as used herein, if the strip is held in place on the rod for 5 seconds and then remains bent to an angle of at least 30° after the strip is removed from the rod (i.e., the strip is deformed such that the straight portions at the ends of the strip are at an angle relative to each other of at least 30°).

As used herein, "flexure resistance" is another means of expressing the flexibility of a material or article and is measured according to the Circular Bend Procedure described in detail in U.S. Pat. No. 5,624,423, issued Apr. 29, 1997 to Anjur et al., herein incorporated by reference in its entirety. Flexure resistance is actually a measurement of peak bending stiffness modeled after the ASTM D4032-82 Circular Bend Procedure. The Circular Bend Procedure of Anjur et al. is a simultaneous multidirectional deformation of a material in which one face of a specimen becomes concave and the other face becomes convex. The Circular Bend Procedure gives a force value related to flexure-resistance, simultaneously averaging stiffness in all directions. Desirably, the absorbent article has a flexure-resistance of less than or equal to about 1,500 grams, more specifically about 1000 grams or less, more specifically still about 700 grams or less and most specifically about 600 grams or less.

As used herein, the term "horizontal," refers to directions in the plane of the article that are substantially parallel to the body-side surface of the article, or, equivalently, substantially normal to the vertical direction of the article, and comprises the transverse direction and the longitudinal direction of the article, as well as intermediate directions.

As used herein, the "absorbent core" of an absorbent article refers to the combination of the central absorbent member and the outer absorbent member which together form substantially all of or a major portion of the absorbent material in the absorbent article. Generally, the absorbent core is held in a facing relationship with the region of the user's body that produces fluid exudates to be absorbed. While additional absorbent material may be incorporated in optional tabs, flaps, or wings that are generally folded away from the exudate-producing surfaces of the body and wrapped around undergarments on the absorbent article, such absorbent material is not considered as part of the absorbent core, as the term is used herein. It is particularly desired that flow from the target region (the insult point adjacent the user's body) toward the longitudinal sides of the absorbent core of the article be hindered by the wicking barrier. Additional means for hindering flow from the longitudinal sides of the absorbent core toward optional flaps, tabs, or wings can also be incorporated in the articles of the present invention, including the use of additional barrier material spanning a vertical distance in the article.

The term "sanitary napkin", as used herein, refers to an article which is worn by females adjacent to the pudendal region that is intended to absorb and contain the various exudates which are discharged from the body (e.g., blood, menses, and urine). While the present invention is shown and described in the form of a sanitary napkin, it should be understood that the present invention is also applicable to other feminine hygiene or catamenial pads such as panty liners, or other absorbent articles such as diapers or incontinence pads. The term "feminine care pad" as used herein is synonymous with sanitary napkin.

As used herein, the "crotch region" of an absorbent article refers to the generally central region that will be in contact with the crotch of the user, near the lowermost part of the torso, and resides between the front and rear portions of the article. Typically the crotch region contains the transverse centerline of the article and generally spans approximately 7 to 10 cm in the longitudinal direction.

"Papermaking fibers," as used herein, include all known cellulosic fibers or fiber mixes comprising cellulosic fibers. Fibers suitable for making the webs of this invention comprise any natural or synthetic cellulosic fibers including, but not limited to nonwoody fibers, such as cotton, abaca, kenaf, sabai grass, flax, esparto grass, straw, jute hemp, bagasse, milkweed floss fibers, and pineapple leaf fibers; and woody fibers such as those obtained from deciduous and coniferous trees, including softwood fibers, such as northern and southern softwood kraft fibers; hardwood fibers, such as eucalyptus, maple, birch, and aspen. Woody fibers can be prepared in high-yield or low-yield forms and can be pulped in any known method, including kraft, sulfite, high-yield pulping methods and other known pulping methods. If bleached, any known bleaching method can be used. Synthetic cellulose fiber types include rayon in all its varieties and other fibers derived from viscose or chemically modified cellulose. Chemically treated natural cellulosic fibers can be used such as mercerized pulps, chemically stiffened or crosslinked fibers, or sulfonated fibers. For good mechanical properties in using papermaking fibers, it is often desirable that the fibers be relatively undamaged and largely unrefined or only lightly refined. While recycled fibers can be used, virgin fibers are generally desirable for their mechanical properties and lack of contaminants. Mercerized fibers, regenerated cellulosic fibers, cellulose produced by microbes, rayon, and other cellulosic material or cellulosic derivatives can be used. Suitable papermaking fibers can also include recycled fibers, virgin fibers, or mixes thereof. In certain embodiments capable of high bulk and good compressive properties, the fibers can have a Canadian Standard Freeness of at least 200, more specifically at least 300, more specifically still at least 400, and most specifically at least 500.

As used herein, "high yield pulp fibers" are those papermaking fibers of pulps produced by pulping processes providing a yield of about 65 percent or greater, more specifically about 75 percent or greater, and still more specifically from about 75 to about 95 percent. Yield is the resulting amount of processed fiber expressed as a percentage of the initial wood mass. High yield pulps include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which contain fibers having high levels of lignin. Characteristic high-yield fibers can have lignin content by mass of about 1% or greater, more specifically about 3% or greater, and still more specifically from about 2% to about 25%. Likewise, high yield fibers can have a kappa number greater than 20, for example. The preferred high yield pulp fibers, after being prepared by pulping and optional bleaching steps and prior to being formed into dry bales or webs, in one embodiment can also be characterized by being comprised of comparatively whole, relatively undamaged fibers, high freeness (200 Canadian Standard Freeness (CSF) or greater, more specifically 250 CSF or greater, and still more specifically 400 CSF or greater), and low fines content (less than 25 percent, more specifically less than percent, still more specifically less that 15 percent, and still more specifically less than percent by the Britt jar test known to those skilled in the art of papermaking). In one embodiment, the high-yield fibers are preferably predominately softwood, more preferably northern softwood, and most preferably northern softwood BCTMP.

As used herein, the term "cellulosic" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose.

As used herein, the term "polymeric web" refers to a porous or nonporous layer primarily composed of polymeric material, and can be a nonwoven web, a plastic film, a polymeric film, an apertured film, or a layer of foam. Polymeric webs can be used as wicking barriers, baffle layers, backsheets, and, if sufficiently liquid pervious, as topsheets of absorbent articles. A polymeric web can consist of about 50 weight percent or more polymeric material, more specifically about 80 weight percent or more polymeric material, and most specifically about 90 weight percent or more polymeric material. Exemplary materials include polyolefins, polyesters, polyvinyl compounds, and polyamides.

As used herein, "bulk" and "density," unless otherwise specified, are based on an oven-dry mass of a sample and a thickness measurement made at a load of 0.34 kPa (0.05 psi) with a 7.62-cm (three-inch) diameter circular platen. Thickness measurements of samples are made in a TAPPI-conditioned room (50% relative humidity and 22.7° C.) after conditioning for at least four hours. Samples should be essentially flat and uniform under the area of the contacting platen. Bulk is expressed as volume per mass of fiber in cc/g and density is the inverse, g/cc.

As used herein, "Wet Bulk" is based on a caliper measurement of a sample according to the definition of "bulk" above (at 0.344 kPa), except that the conditioned sample is uniformly misted with deionized water until the moistened mass of the sample is approximately 250% of the dry mass of the sample (i.e., the added mass of the moisture is 150% of the dry sample weight). If the sample cannot absorb and retain enough moisture from misting to increase the mass by 150%, then the highest level of achievable moisture add-on below 150% but still above 100% moisture add on should be used. The Wet Bulk is calculated as the thickness of the substantially planar moistened sample under a load of 0.344 kPa (0.05 psi) divided by the oven-dry sample basis weight in g/cc. Absorbent materials in the absorbent members of the present invention can have a Wet Bulk of about 4 cc/g or greater, more specifically about 6 cc/g or greater, more specifically still about 10 cc/g or greater, more specifically still about 10 cc/g or greater, and most specifically about 15 cc/g or greater, with an exemplary range of from about 5 cc/g to about 20 cc/g.

As used herein, a material will be considered to be "water soluble" when it substantially dissolves in excess water to form a solution, thereby losing its initial form and becoming essentially molecularly dispersed throughout the water solution. As a general rule, a water-soluble material will be free from a substantial degree of crosslinking, as crosslinking tends to render a material water insoluble. A material that is "water insoluble" is one that is not water soluble according to the above definition.

As used herein, the term "extensible" refers to articles that can increase in at least one of their dimensions in the x-y plane. The x-y plane is a plane generally parallel to the faces of the article. The term extensible includes articles that are stretchable and elastically stretchable (defined below). In the case of a sanitary napkin comprising an absorbent core, for example, the article and the absorbent core are desirably extensible both in length and width. The absorbent article, however, may only be extensible in one of these directions. Preferably, the article is extensible at least in the longitudinal direction. Examples of extensible materials and articles, and their methods of preparation, are disclosed in U.S. Pat. No. 5,611,790, issued Mar. 18, 1997 to Osborn, herein incorporated by reference in its entirety.

The absorbent article comprising an absorbent core can, in addition to being extensible, also be stretchable. The term "stretchable", as used herein, refers to articles that are extensible when stretching forces are applied to the article and offer some resistance to stretching. The terms "elastically stretchable" or "elastically extensible" are intended to be synonymous. These terms, as used herein, mean that when in-plane stretching forces are removed, the article or absorbent fibrous structure will tend to return toward its unextended or unstretched dimensions (or original dimensions). It need not return all the way to its unstretched dimensions, however. It may return to relaxed dimensions between its unstretched dimensions and extended (or stretched dimensions).

As used herein, "critical density" refers to the density at which a fibrous mat or pad will neither collapse nor expand when fully saturated with deionized water at 25° C. For papermaking fibers, the critical density is generally quoted as 0.2 grams/cc but actually ranges from about 0.17 to about 0.25 grams/cc. Wet-laid paper sheets tend to have densities near the critical density. The absorbent materials for the absorbent members of the present invention can be produced at an initial density well below the critical density, such that the critical density is at least 2, 4, 6, 10, 20, or 30 times greater than the dry absorbent structure density. However, after calendering or other forms of mechanical compression, the density of the absorbent fibrous structure can approach the critical density or be above it, such that the density of the central absorbent member or the outer absorbent member can be greater than the critical density by a factor of about 1.2 or greater, more specifically 1.5 or greater, and more specifically still about 2 or greater. The outer absorbent member can have a density significantly below the critical density, such as below about 0.1 g/cc. Desirably, at least one layer of the central absorbent member has a density near or below the critical density, such as about 0.2 g/cc.

As used herein, "biodegradable" refers to the ability of a compound to ultimately be degraded completely into carbon dioxide and water or biomass by microorganisms and/or natural environmental factors. In one embodiment, the outer absorbent member and central absorbent member are substantially biodegradable. In another embodiment, the outer absorbent member, the central absorbent member, and the wicking barrier all comprises biodegradable materials or are substantially biodegradable.

As used herein, the term "hydrophobic" refers to a material having a contact angle of water in air of at least 90 degrees. In contrast, as used herein, the term "hydrophilic" refers to a material having a contact angle of water in air of less than 90 degrees.

As used herein, the term "surfactant" includes a single surfactant or a mixture of two or more surfactants. If a mixture of two or more surfactants is employed, the surfactants may be selected from the same or different classes, provided only that the surfactants present in the mixture are compatible with each other. In general, the surfactant can be any surfactant known to those having ordinary skill in the art, including anionic, cationic, nonionic and amphoteric surfactants. Examples of anionic surfactants include, among others, linear and branched-chain sodium alkylbenzene-sulfonates; linear and branched-chain alkyl sulfates; linear and branched-chain alkyl ethoxy sulfates; and silicone phosphate esters, silicone sulfates, and silicone carboxylates such as those manufactured by Lambent Technologies, located in Norcross, Ga. Cationic surfactants include, by way of illustration, tallow trimethylammonium chloride and, more generally, silicone amides, silicone amido quaternary amines, and silicone imidazoline quaternary amines. Examples of nonionic surfactants, include, again by way of illustration only, alkyl polyethoxylates; polyethoxylated alkylphenols; fatty acid ethanol amides; dimethicone copolyol esters, dimethiconol esters, and dimethicone copolyols such as those manufactured by Lambent Technologies; and complex polymers of ethylene oxide, propylene oxide, and alcohols. One exemplary class of amphoteric surfactants are the silicone amphoterics manufactured by Lambent Technologies (Norcross, Ga.).

As used herein, "wet strength agents" are materials used to immobilize the bonds between fibers in the wet state. Typically, the means by which fibers are held together in paper and tissue products involve hydrogen bonds and sometimes combinations of hydrogen bonds and covalent and/or ionic bonds. In the present invention, it is desirable to provide a material that will allow bonding of fibers in such a way as to immobilize the fiber to fiber bond points and make them resistant to disruption in the wet state. In this instance, the wet state usually will mean when the product is largely saturated with water or other aqueous solutions, but could also mean significant saturation with body fluids such as urine, blood, mucus, menses, runny bowel movement, lymph and other body exudates.

There are a number of materials commonly used in the paper industry to impart wet strength to paper and board that are applicable to this invention. These materials are known in the art as "wet strength agents" and are commercially available from a wide variety of sources. Any material that when added to a paper web or sheet results in providing the sheet with a wet geometric tensile strength:dry geometric tensile strength ratio in excess of 0.1 will, for purposes of this invention, be termed a wet strength agent. Typically these materials are termed either as permanent wet strength agents or as "temporary" wet strength agents. For the purposes of differentiating permanent from temporary wet strength, permanent will be defined as those resins which, when incorporated into paper or tissue products, will provide a product that retains more than 50% of its original wet strength after exposure to water for a period of at least five minutes. Temporary wet strength agents are those which show less than 50% of their original wet strength after being saturated with water for five minutes. Both classes of material find application in the present invention. The amount of wet strength agent added to the pulp fibers can be at least about 0.1 dry weight percent, more specifically about 0.2 dry weight percent or greater, and still more specifically from about 0.1 to about 3 dry weight percent, based on the dry weight of the fibers.

Permanent wet strength agents will provide a more or less long-term wet resilience to the structure. In contrast, the temporary wet strength agents would provide structures that had low density and high resilience, but would not provide a structure that had long-term resistance to exposure to water or body fluids. The mechanism by which the wet strength is generated has little influence on the products of this invention as long as the essential property of generating water-resistant bonding at the fiber/fiber bond points is obtained.

Suitable permanent wet strength agents are typically water soluble, cationic oligomeric or polymeric resins that are capable of either crosslinking with themselves (homocrosslinking) or with the cellulose or other constituent of the wood fiber. The most widely-used materials for this purpose are the class of polymer known as polyamide-polyamine-epichlorohydrin type resins. These materials have been described in patents issued to Keim (U.S. Pat. Nos. 3,700,623 and 3,772,076) and are sold by Hercules, Inc., located in Wilmington, Del., as KYMENE 557H polyamine-epichlorohydrin resins. Related materials are marketed by Henkel Chemical Co., located in Charlotte, N.C., and Georgia-Pacific Resins, Inc., located in Atlanta, Ga.

Polyamide-epichlorohydrin resins are also useful as bonding resins in this invention. Materials developed by Monsanto and marketed under the SANTO RES™ label are base-activated polyamide-epichlorohydrin resins that can be used in the present invention. These materials are described in patents issued to Petrovich (U.S. Pat. Nos. 3,885,158; 3,899,388; 4,129,528 and 4,147,586) and van Eenam (U.S. Pat. No. 4,222,921). Although they are not as commonly used in consumer products, polyethylenimine resins are also suitable for immobilizing the bond points in the products of this invention. Another class of permanent-type wet strength agents are exemplified by the aminoplast resins obtained by reaction of formaldehyde with melamine or urea.

Suitable temporary wet strength resins include, but are not limited to, those resins that have been developed by American Cyanamid and are marketed under the name PAREZ™ 631 NC wet strength resin (now available from Cytec Industries, located in West Paterson, N.J.). This and similar resins are described in U.S. Pat. No. 3,556,932 to Coscia et al. and U.S. Pat. No. 3,556,933 to Williams et al. Other temporary wet strength agents that should find application in this invention include modified starches such as those available from National Starch and marketed as CO-BOND™ 1000 modified starch. It is believed that these and related starches are disclosed in U.S. Pat. No. 4,675,394 to Solarek et al. Derivatized dialdehyde starches may also provide temporary wet strength. It is also expected that other temporary wet strength materials such as those described in U.S. Pat. Nos. 4,981,557; 5,008,344 and 5,085,736 to Bjorkquist would be of use in this invention. With respect to the classes and the types of wet strength resins listed, it should be understood that this listing is simply to provide examples and that this is neither meant to exclude other types of wet strength resins, nor is it meant to limit the scope of this invention.

Although wet strength agents as described above find particular advantage for use in connection with this invention, other types of bonding agents can also be used to provide the necessary wet resiliency. They can be applied at the wet end of the basesheet manufacturing process or applied by spraying or printing after the basesheet is formed or after it is dried.

Figure 1B:
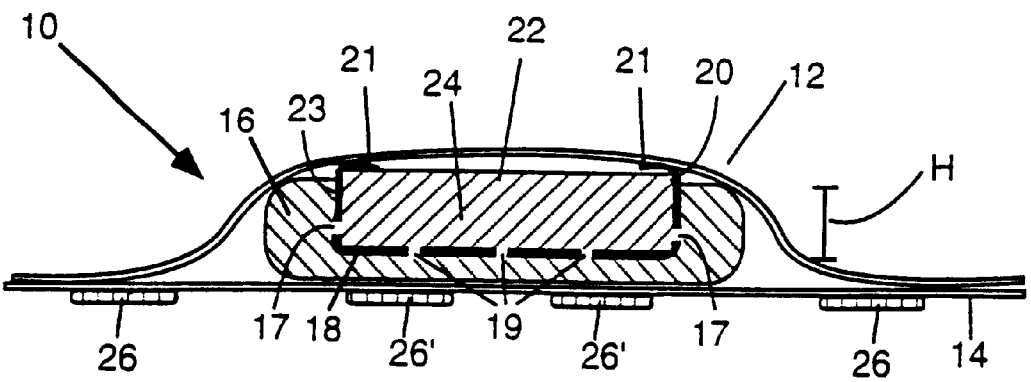

A cross section of one embodiment of an absorbent article of the present invention is depicted in FIGS. 1A and 1B. The absorbent article, labeled generally as 10, comprises a liquid pervious topsheet 12 on the body-side surface of the article, a liquid impervious backsheet 14 on the opposing garment-side surface of the article, an outer absorbent member 16 having a region of reduced basis weight or thickness having a surface 18 which defines the boundary of a central depression or void. The surface of the depression or void 18 is adjacent (i.e., is in contact with or is lined by) a wicking barrier 20 which serves to prevent or reduce lateral liquid flow, particularly wicking, from the central absorbent member 22 to the surrounding outer absorbent member 16 and which can also prevent or reduce wicking in the z-direction from the central absorbent member to the underlying region of the outer absorbent member. The wicking barrier spans a vertical distance H between the elevation of the body-side surface of the outer absorbent member and the elevation of the lowest portion of the surface of the central depression or void 18 in the outer absorbent member 16. The wicking barrier has a vertical component 23 (which need not be substantially vertical in orientation as shown but spans a vertical distance) and has a horizontal component 21 acting as a ledge and spanning a horizontal distance on the body-side surface of either the outer absorbent member 16 or the central absorbent member 22. (The absorbent core comprises the outer absorbent member 16 and the central absorbent member 22). In FIG. 1A, the horizontal component 21 of the wicking barrier 20 resides primarily on the body-side surface of the outer absorbent member 16, which is generally the more desirable configuration. In FIG. 1B, the horizontal component 21 of the wicking barrier 20 resides primarily on the body-side surface of the central absorbent member 22, which is also within the scope of the present invention. In FIG. 1A, the horizontal component 21 of the wicking barrier 20 may cover only a fraction of the exposed body-side surface of the outer absorbent member, as shown (e.g., less than 50% or less than 20% of the linear distance from the central absorbent member to the longitudinal edge of the outer absorbent member), or it can cover substantially all of the body-side surface of the outer absorbent member in any particular cross section, particularly in the crotch region of the article, to prevent wicking contact of the central absorbent member with the outer absorbent member when the article is bunched up in use. In both FIGS. 1A and 1B, the central absorbent member 22 comprises an absorbent strip or section 24 which may be a rectangular or other shaped insert suitably comprising hydrophilic fibers such as airlaid or wet laid cellulose, including a pad of fluff pulp, multiple layers of creped or uncreped tissue, peat moss, cotton, mixtures of absorbent fibers and superabsorbent particles or fibers, or layers of fluff separated by tissue layers. The absorbent section 24 may also comprise absorbent foams or foam-fiber composites. Desirably, the AUL value of the absorbent section 24 is about 10 grams/gram or greater. In use, the central absorbent member will tend to fill first with fluid, after which wicking or bulk flow of fluid to the surrounding or underlying regions of the outer absorbent member can take place if sufficient fluid enters the absorbent article.

Entry of fluid from the central absorbent member 22 to the outer absorbent member 16 is made possible by the presence of optional apertures or openings 17, 19 in the wicking barrier 20 remote from the body-side surface of the article. It is intended that body fluid will primarily enter the absorbent article in or immediately above the central absorbent member 22, passing through topsheet 12 into the central absorbent member 22. If fluid spreads radially from the central absorbent member 22 to the outer absorbent member 16, it is intended that such movement of fluid will occur by a tortuous pathway rather than by directly wicking from the body-side surface of the central absorbent member 22 to the body-side surface of the outer absorbent member 16. A tortuous path is established by the optional apertures or openings 17 and 19 in the wicking barrier 20 such that fluid entering the central absorbent member 20 must first migrate downward into the central absorbent member 20 through the openings in the wicking barrier and from thence into the radially outward sections of the outer absorbent member 16, still submerged beneath the body-side surface of the outer absorbent member 16, thus keeping fluid away from the exposed surfaces of the outer absorbent member 16. The depth, size, and number of the openings 17 and 19 can be adjusted to provide the proper balance between hindering radially outward or lateral flow toward the edges of the article and preventing oversaturation or overflowing of fluid from the central absorbent member 22. The openings 17 and 19 are not needed if the absorbent capacity of the central absorbent member 22 is adequate for the anticipated fluid loadings the absorbent article 10 will receive.

The topsheet 12 is liquid permeable and, when the article 10 is in use, is in close proximity to the skin of the user. Desirably, the topsheet 12 is compliant, soft and nonirritating to the user's skin. It can be made from any of the conventional materials for this type of use. Nonlimiting examples of suitable materials include woven and nonwoven polyester, polypropylene, nylon, rayon or the like, particularly in the form of formed or apertured thermoplastic films, including those described in U.S. Pat. No. 4,324,246 issued to Mullane and Smith on Apr. 13, 1982 and U.S. Pat. No. 4,342,314 issued to Radel and Thompson on Aug. 3, 1982, both of which are incorporated herein in their entirety by reference. Mechanically apertured forms can also be used.

Other known cover materials can be employed, including those made from textured cellulosic basesheets with hydrophobic matter added to selected portions of the basesheet, particularly the most elevated portions of the basesheet, as described in commonly owned copending U.S. application, "Dual-zoned Absorbent Webs", Ser. No. 08/997,287, filed Dec. 22, 1997, previously incorporated by reference.

The outer surface of topsheet 12 can be treated with a surfactant to improve liquid penetration, and can have gradients in wettability created having different chemical treatments on the two surfaces of the topsheet 12 or by having different regions in the plane of the topsheet 12 having differing surface chemistry, such that fluid is preferentially absorbed in targeted intake regions and repelled by other regions. Surfactant treatment can be accomplished by any of the common techniques known to those skilled in the art, including, for example, by spraying, by padding or by the use of transfer rolls.

Desirably, the inner surface of the topsheet 12 is secured in contacting relation to the absorbent core which comprises the central absorbent member 22 and the outer absorbent member 16. The topsheet 12 can be maintained in contact with the absorbent core by tensional forces, by ultrasonic or thermal bonding, by needling entanglement, or by application of adhesive, preferably in spaced limited areas, to the inner surface of the topsheet 12. Adhesives can be applied by the same methods as the surfactant can be applied to the outer surface of the topsheet 12, but desirably are applied in a spiral pattern or other fine pattern for good adhesion but low interference with fluid intake. Adhesives or other bonding methods can also join the horizontal component 21 of the wicking barrier 20 to the topsheet 12.

The outer absorbent member 16 is positioned between the topsheet 12 and the backsheet 14. The outer absorbent member 16 is generally compressible, conformable and nonirritating to the user's skin, comprising materials discussed herein.

The backsheet 14 is impervious to liquids and, thus, prevents menstrual fluid or other body exudates which may be released from the absorbent core (comprising the outer absorbent member 16 and the central absorbent member 22) from soiling the body or clothing of the user. Any backsheet material used in the art for such purpose can be utilized herein. Suitable materials are embossed or nonembossed polyethylene films and laminated tissue, desirably treated with sizing agents and wet strength agents. Breathable films that permit moisture transpiration to occur without significant condensation can also be used. The outer cover 13 may be embossed or provided with odor-controlling materials.

The outer surface of backsheet 14 can be coated with adhesive such as the pressure-sensitive adhesive strips 26,26' shown in FIGS. 1A and 1B. The adhesive, for example, can provide a means for securing the pad in the crotch portion of a panty. Any adhesive or glue used in the art for such purposes can be used herein, with pressure sensitive adhesives being preferred. Also, before sanitary napkin 10 is placed in use, the pressure sensitive adhesive should be covered with one or more removable release liners (not shown). Any commercially available release liners commonly used for such purposes can be utilized. In several embodiments, it is desirable that outer adhesive strips 26 be disposed as close as possible to the longitudinal sides of the article to provide better attachment of the article to the user's undergarments, thus reducing the tendency of side portions of the article to bunch and come into liquid communication with the surface of the central absorbent member 22. One or more additional inner adhesive strips 26' can also be used for improved security. The outer adhesive strips 26 can be any useful width, such as from about 1 mm to about 15 mm, and more specifically from about 3 mm to about 10 mm.

It is desirable that the width of the central absorbent member 22 be from about 1 to about 12 centimeters, more specifically from about 2 to about 7 centimeters, and most specifically from about 2 to about 5 centimeters.

Figure 2:
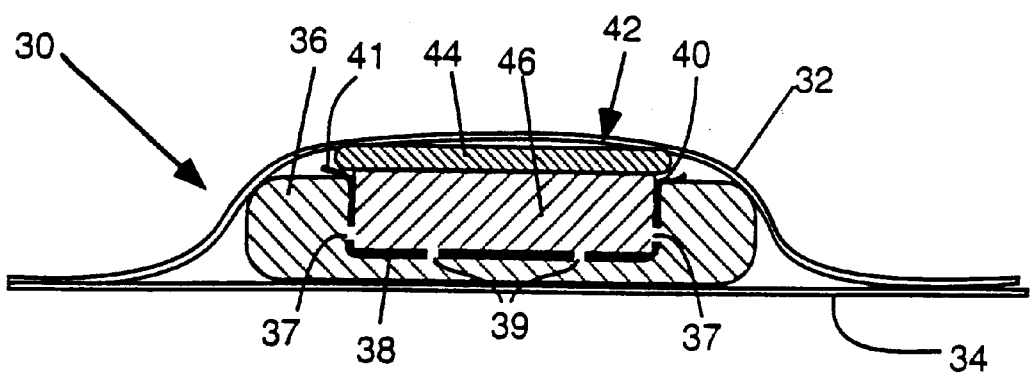
FIG. 2 depicts a cross-section of a sanitary napkin of the present invention having two absorbent components in the central absorbent member.

FIG. 2 shows a related embodiment for an absorbent article 30 similar to that of FIG. 1. The central absorbent member 42 comprises two layers of material, an upper layer 44 and a lower layer 46, wherein the lower layer desirably comprises at least one ply of wet laid tissue of higher density than the upper layer. The outer absorbent member 36 has a region of reduced thickness defining a central depression or void 38 in the outer absorbent member. The upper layer 44 can be smaller, larger, or identical in lateral dimensions than the lower layer, but is pictured as having a greater width. The upper layer 44 can fit into the depression or void of the outer absorbent member 36 on top of the lower layer 46 such that its upper surface is coplanar or aligned with the body side (upper) surface of the surrounding outer absorbent member 36, but as depicted in FIG. 2 rises above the surface of the outer absorbent member. A film of barrier material 40, which can comprise an impermeable, flexible polymeric film, a meltblown film, an apertured film, a hydrophobically treated tissue, a nonwoven web, or other wicking inhibiting layer, separates the lower layer 46 of the central absorbent member 42 from the outer absorbent member 36, particularly hindering lateral flow from the vertical sides of the lower layer 46 to the approximately vertical sides of the outer absorbent member 36 that define the depression 38. The permeability or porosity or surface chemistry of the barrier material 40 can vary with position along the barrier material such that wicking is delayed or hindered to differing extents at different locations. For example, the barrier material may deter lateral wicking but not deter or even promote wicking in the z-direction (from the lower layer 46 to the underlying portion of the outer absorbent member 36). This may be achieved, for example, by providing large apertures 37, 39 in the barrier material 40 in contact with the lower surface of the lower layer 46 of the central absorbent member 42, while the barrier material adjacent the sides of the central absorbent member 42 lacks apertures or has smaller or fewer apertures relative to the horizontal portion underneath said lower layer 46. The horizontal component 41 of the wicking barrier 40 desirably lacks substantial fluid permeability and desirably is impermeable or has a Darcian permeability less than $1\times10^{-15}$ m$^2$, more specifically less than $1\times10^{-16}$ m$^2$ as measured by standard permeability measurement techniques based on Darcy's law with steady-state water flow through a film of known thickness under a pressure differential of 1 kPa. (See, for example, *Porous Media: Fluid Transport and Pore Structure*, by F. A. L. Dullien, Academic Press, New York, 1979, pp. 78–83, and Absorbency, ed. by P. K. Chatterjee, Elsevier, 1985, pp. 42–44).

Figure 3A:
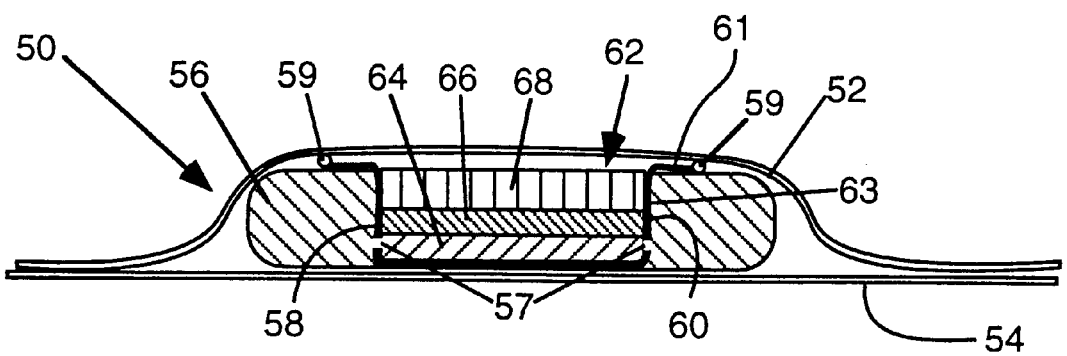
FIG. 3 depicts a cross-section of a sanitary napkin of the present invention having three absorbent components in the central absorbent member.
Figure 3B:
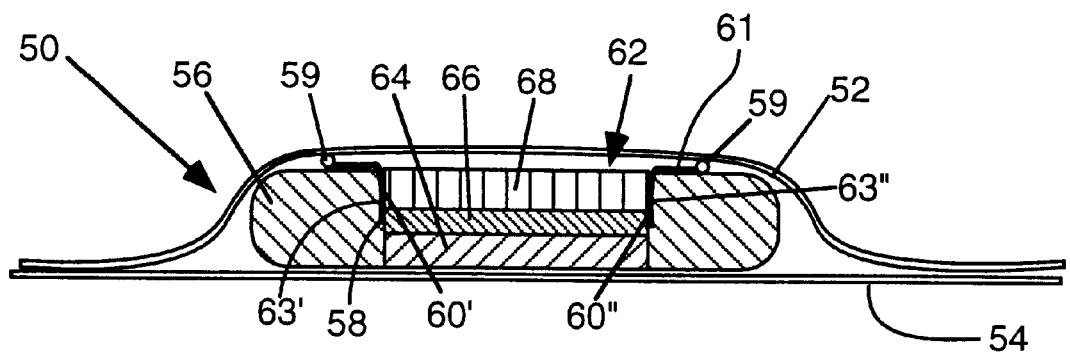

FIGS. 3A and 3B depict a related embodiment of a sanitary napkin 50 in which the central void 58 extends across the entire thickness of the outer absorbent member 56, as can be formed by stamping or cutting out the central portion of the outer absorbent member 56. The central void 58 is lined by a polymeric film, a meltblown layer or other suitable barrier material serving as a wicking barrier 60. The wicking barrier 60 has a vertical component 63 and a horizontal component 61 running on the body-side surface of the outer absorbent member 56 serving as a ledge between absorbent members 56, 62. In FIG. 3A, the entry of fluid from the central absorbent member 62 to the outer absorbent member 56 is made possible by the presence of optional apertures or openings 57. In FIG. 3A, the vertical extent of the vertical component 63 of the wicking barrier 60 is substantially the same as the thickness of the outer absorbent member 56. In FIG. 3B, an alternative form is shown in which the wicking barrier comprises two strips of material 60', 60'', one on each longitudinal side of the central absorbent member 62, both with vertical components 63', 63'' traversing only a portion of the vertical thickness of the absorbent core. In both FIG. 3A and FIG. 3B, the wicking barrier comprises a horizontal component 61 and a vertical component 63, and the horizontal component 61 overlaps a portion of the body-side surface of the outer absorbent member 56 to define a ledge encircling the central absorbent member 62 when the outer absorbent member 56 encircles the central absorbent member 62. The horizontal component 61 defines longitudinal side bands when the central absorbent member 62 extends along the full longitudinal length of the outer absorbent member 56. The ledge 60 of the wicking barrier is attached by adhesives 59 or other known means to the topsheet 52 for improved stability and flow control. In FIG. 3A, the wicking barrier 60 can also be attached by adhesives or other bonding methods to the backsheet 54.

In one embodiment, the wicking barrier 60 is colored, such as a peach or blue color to provide a distinctive indication of the barrier effect that results from having a central absorbent member 62 in partial fluid isolation from the surrounding outer absorbent member 56.

The central absorbent member 62 comprises three layers of material, desirably having decreasing density toward the bottom (remote from the body side) of the central absorbent member 62 for improved retention of absorbed fluid. In particular, the middle layer 66 desirably has a higher density or lower mean pore size or higher capillary pressure than the upper layer 68. Further, the bottom layer 64 desirably has a higher density or lower mean pore size or higher capillary pressure than the middle layer 66. The bottom layer 64 can be a wet-laid tissue having a density of about 0.2 g/cc or greater, while the middle layer 66 and the top layer 68 may be airlaid or wet laid materials or absorbent foams or fiber-foam composites, such as those disclosed in the commonly owned, copending U.S. patent application of F.-J. Chen et al., "Fibrous Absorbent Material and Methods of Making the Same," Ser. No. 09/083,873, filed May 22, 1998, previously incorporated by reference. Wet-laid and/or foam-formed composites of fibers and superabsorbent materials can be used. Any of the layers 64, 66, and 68 as well as the outer absorbent member 56 can be embossed or can comprise superabsorbents, menses viscosity modifiers such as enzymes and surfactants, or odor absorbents. Additionally, an apertured film (not shown) may be interposed between any two of the layers 64, 66, or 68 to further control flow, including delaying transfer or providing preferentially one-way flow from top to bottom, wherein the apertured film resists upward fluid flow from one layer to the superposed layer while permitting downward flow.

The topsheet 52 may be an apertured film, a nonwoven web, or a dual-zoned film wherein a textured hydrophilic basesheet is provided with hydrophobic matter on the uppermost regions, as disclosed in commonly owned, copending U.S. patent application of Chen et al., Ser. No. 08/997,287, filed Dec. 22, 1997. The backsheet 54 can be a breathable film, cloth, or a fiber-polymer composite and desirably is substantially impervious to liquid. It may also be provided with adhesives (not shown) on its outer surface for attachment to undergarments.

Figure 4A:
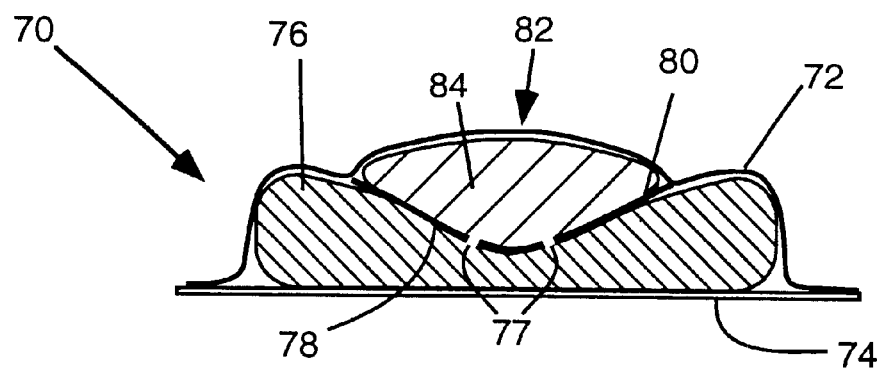
FIG. 4 depicts a cross-section of a sanitary napkin of the present invention having a contoured central absorbent member.
Figure 4B:
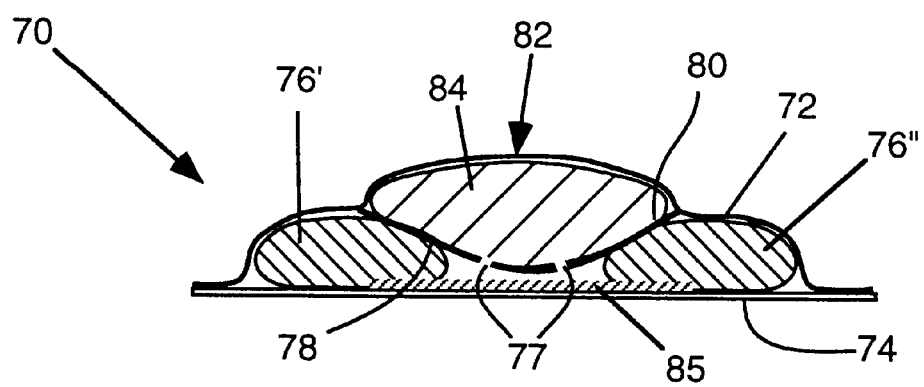

FIGS. 4A and 4B depict a related embodiment for a sanitary napkin or feminine pad 70 wherein the central depression or void 78 in the outer absorbent member 76 is not rectilinear but has contoured sides without a distinct vertical precipice along the boundaries of the depression or void 78. The depression penetrates into the outer absorbent member 76, relative to the maximum height of the side regions of the outer absorbent member, by at least about 10% of said maximum height, more specifically by at least about 25%, more specifically still by at least 50%, and most specifically from about 30% to 100% of the maximum height of the outer absorbent member along a cross-section of the absorbent article. In FIG. 4A the penetration of the central void 78 into the outer absorbent member 76 is partial, while in FIG. 4B the central void 78 extends completely through the outer absorbent member 76. A wicking barrier 80 comprising a nonabsorbent barrier material impedes fluid communication between the central absorbent layer 84 of the central absorbent member 82 and the outer absorbent member 76 such that lateral wicking to the surrounding outer absorbent member 76 is delayed or substantially prevented, resulting in center-fill performance and reduce leakage from the sides of the absorbent article 70. The central absorbent member 82 comprises a contoured layer 84 with a contoured profile adapted to provide improved body fit and comfort. Desirably, the contoured layer 84 comprises a wet resilient material with a wet bulk of about 8 cc/g or higher. As depicted, the wicking barrier 80 extends slightly beyond the edges of the central absorbent layer, though it can substantially cover the body-side surface of the outer absorbent member 76 or can be coextensive with the central layer 84 of the central absorbent member 82. Wicking barrier 80 can be provided with apertures 77 remote from the body-side surface of the central absorbent member. The wicking barrier 80 may be attached to the topsheet 72 for improved stability and integrity in use.

In FIG. 4B, an optional additional intake layer 85 such as a layer of tissue is attached to the backsheet 74 to provide fluid communication between the two divided portions 76', 76" of the outer absorbent member and to help retain or distribute fluid passing thought apertures 77 of the wicking barrier 80 into the void region below the wicking barrier.

Figure 5A:
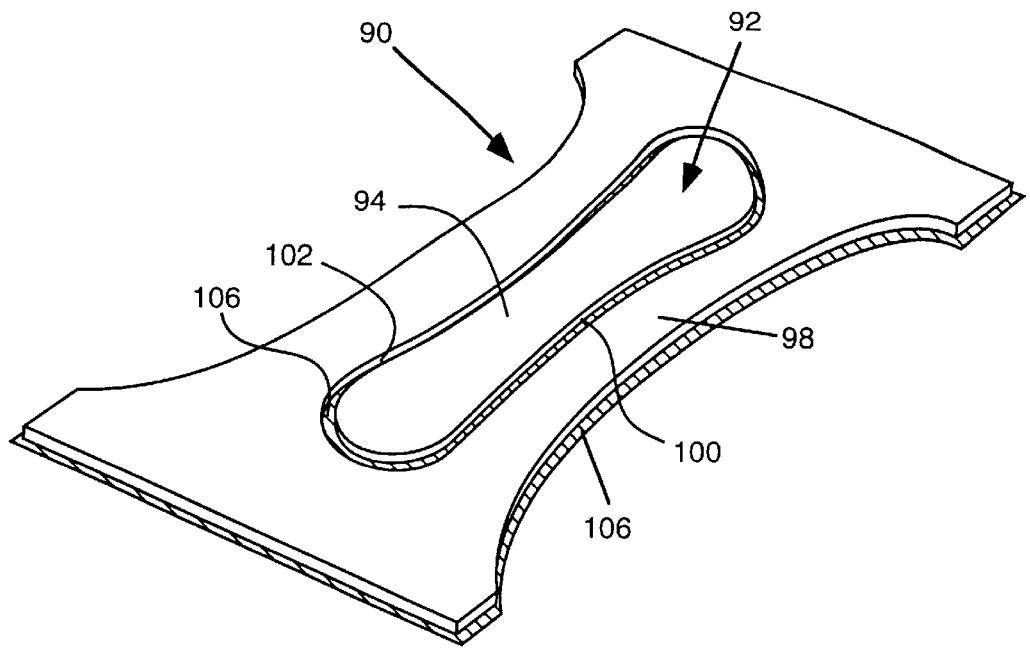
FIG. 5 shows a diaper having a central absorbent member surrounded by a moat.

FIG. 5 depicts certain components of a diaper 90 according to the present invention. In FIG. 5A, a shaped outer absorbent member 98 has a central region that has been cut out, defining a void with side edges 102. The outer absorbent member 98 resides on a liquid impervious backsheet 106. In the central void in the outer absorbent member 98 is a central absorbent member 92 comprising a central absorbent insert 94 slightly smaller in lateral dimensions than the central void and substantially concentric with the surrounding outer absorbent member 98. The central absorbent insert 94 has side edges 100. The finite gap between the side edges 100 of the central absorbent insert 94 and the side edges 102 of the outer absorbent member 98 serves as a moat to impede lateral wicking from the central absorbent member 92 to the surrounding outer absorbent member, thus promoting center fill of the central absorbent member rather than wicking throughout the diaper. The moat can also serve to channel runoff or fast-moving liquid urine, for example, to other portions of the outer absorbent member 98 and the central absorbent member 92 to reduce leakage during an insult. While a moat can reduce wicking, it still permits easy radial spreading of bulk fluid once fluid enters the channel. Therefore, it is desirable for effective center fill performance that an additional wicking barrier be present (not shown), such as a polymeric web, which spans a vertical distance.

Further, the wicking barrier should desirably have a horizontal component (not shown) as well on the surface of the outer absorbent member to prevent fluid communications between the outer absorbent member and the central absorbent member when the diaper is bunched together in use.

The central absorbent insert 94 may comprise the same material as the outer absorbent member but desirably has a density gradient and more than one layer (not shown) to retain fluid away from the body of the wearer. For example, a high-bulk layer of airlaid material or tissue could serve as an upper layer for effective fluid intake. An underlying lower layer of densified airlaid material or wet laid material, either being optionally combined with superabsorbent material, could then serve to retain fluid by virtue of its higher capillary suction away from the body of the wearer. The more porous upper layer could serve in effect as a surge layer or could be a surge layer of synthetic polymeric material in nonwoven form.

The central absorbent member 92 need not extend into the back portions of the diaper where collection of feces rather than urine may be the objective. The region most likely to receive feces, particularly runny bowel movement, may be provided with additional voids and gaps in the outer absorbent member 98 to provide space for receiving bowel movement and holding it away from the skin of the user.

Figure 5B:
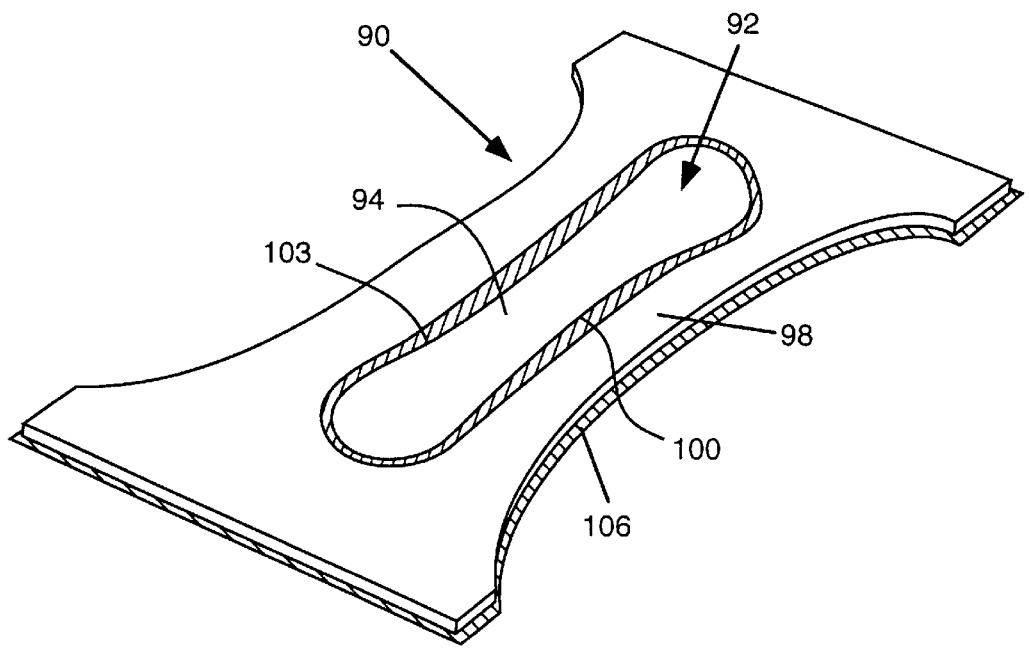

FIG. 5B depicts the same components as FIG. 5A except that instead of a moat, a polymeric film is used as the wicking barrier 103, having a horizontal component visible on the surface of the outer absorbent member 98. The horizontal component traverses a greater distance normal to the periphery of the central absorbent member 92 in the crotch region of the article 90 for additional leakage protection. The wicking barrier 103 also passes under the central absorbent member 92 and contacts the backsheet 106, where it may be fixedly attached or may be unattached and able to slidably move relative to the backsheet for reduced stiffness. The wicking barrier 103 may be adhesively attached to the topsheet (not shown).

Figure 6:
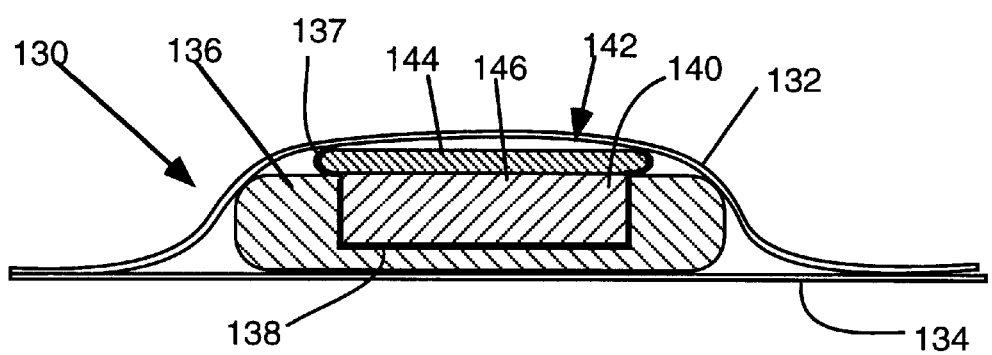
FIG. 6 depicts a cross-section of a sanitary napkin wherein barrier material is wrapped around the upper surface of the central absorbent member.

FIG. 6 depicts an embodiment of an absorbent article 130 in which a portion of an upper layer 144 of the central absorbent member 142 rises above the body-side surface of the surrounding or adjoining outer absorbent member 136 and is partially wrapped by an upper portion 137 of the wicking barrier 140 that lines the surface of the central void or depression 138 in the outer absorbent member 136 for receiving an insert. The upper portion 137 of the wicking barrier 140 can be attached to the topsheet 132. Said upper portion 137 includes a horizontal component spanning a horizontal distance on the body-side surface of the upper layer 144 of the central absorbent member 142. The upper portion of the barrier material 137 which wraps the edge of the upper layer 144 of the central absorbent member prevents liquid from spreading laterally onto the surface or top portions of the outer absorbent member 136 and promotes liquid flow downward into the lower layer 138 of the central absorbent member 142. The central void 138 may extend to the backsheet 134, but as depicted only extends a portion of the thickness of the outer absorbent member 136. If desired, additional barrier material (not shown) could be disposed on the exposed body-side surface of the outer absorbent member 136 to further prevent fluid communication with the central absorbent member 142.

The wicking barrier 140 need not be completely impervious but suitably permits liquid flow from the central absorbent member 142 to the surrounding outer absorbent member 136 when the central absorbent member 142 is nearly saturated. Thus, the wicking barrier 140 can be a polymeric film provided with apertures or small pores, or may be a meltblown web or other porous, desirably hydrophobic material. It can also be a hotmelt or thermoplastic material introduced between or onto the absorbent members of the absorbent core after their formation to provide fluid isolation between members.

Figure 7A:
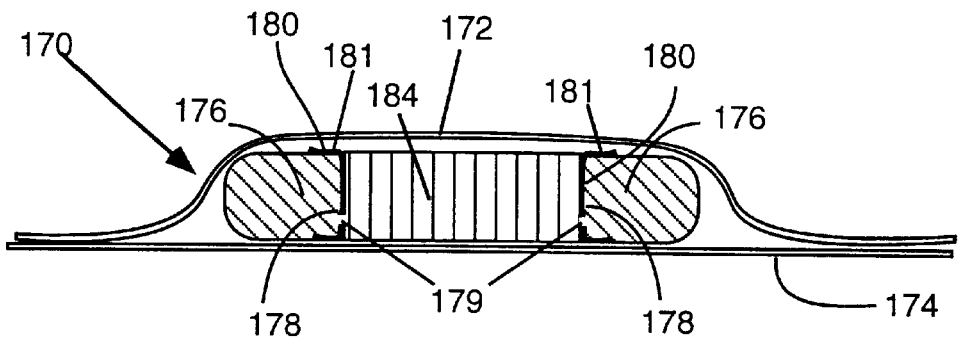
FIG. 7 depicts a cross-section of an absorbent article with a central absorbent member and an outer absorbent member, with a wicking barrier that does not pass beneath the central absorbent member.
Figure 7B:
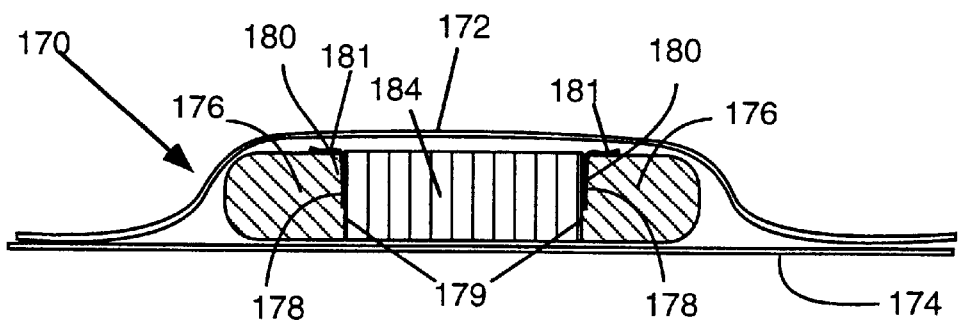
Figure 7C:
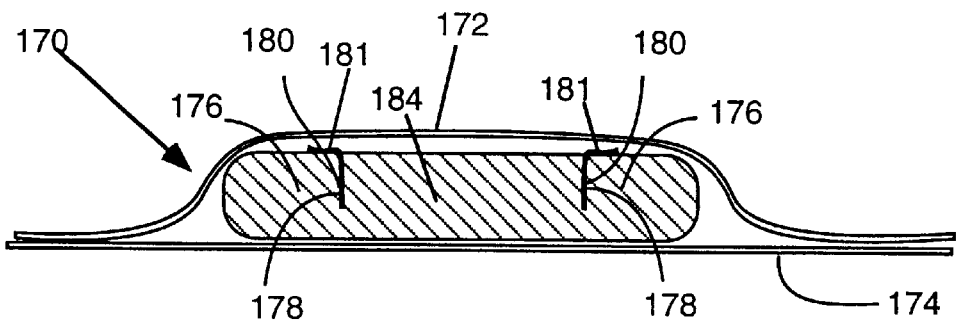

FIGS. 7A–7C depict embodiments of an absorbent article 170 in which the wicking barrier 180 is divided into two longitudinal strips that longitudinally separate the edges of a central absorbent member 184 from the outer absorbent member 176. An absorbent core comprising the central absorbent member 184 and the outer absorbent member 176 is disposed between a backsheet 174 and a topsheet 172, and the separate strips of the wicking barrier 180 at least partially separate the two members of the absorbent core. As shown here, the wicking barrier 180 comprises two strips 180 that do not extend substantially underneath the central absorbent member 172 (i.e., on the side away from the body-side surface). Each wicking barrier strip comprises a vertical component 178 and a horizontal component 181 on the body-side surface of the absorbent core. In FIG. 7A the wicking barrier strips 180 extend over the full thickness of the outer absorbent member 176 and wrap it on each side, forming a C-shape around each portion of the outer absorbent member 176. The wicking barrier 180 is optionally provided with apertures 179 substantially away from the body-side surface of the central absorbent member 184 to permit delayed fluid flow from the central absorbent member 184 to the outer absorbent member 176 but only by a significantly more tortuous route than would be available were the wicking barrier not present. In an alternative embodiment (not shown), the two portions of the wicking barrier 180 may substantially completely encase the outer absorbent member 176 such that the absorbent material of the outer absorbent member 176 is essentially completely isolated from all fluid communication with the central absorbent member 184. In that case, the outer absorbent member 176 may also function primarily as an outer shaping member, providing comfort and fit against the body of the wearer, particularly if the material encased therein is bulky, soft, and suitably deformable, such as high loft fluff pulp, a carded web, or a sponge.

In FIG. 7B, the vertical components 178 of the wicking barrier 180 extend downward from the body-side surface of the absorbent core for only a portion of the thickness of the outer absorbent member (e.g., 30% or more of the thickness of the outer absorbent member, alternatively 50% or more or 70% or more) to prevent lateral wicking transport of fluid from the upper portions of the central absorbent member 184 to the upper portions of the outer absorbent member 176, forcing any transport of fluid from the center of the article toward the longitudinal sides to occur by a more tortuous route beneath the wicking barrier 180. The horizontal component 181 and the vertical component 178 of the wicking barrier 180 are still present. In FIG. 7C, the configuration of the wicking barrier 180 is the same as in FIG. 7B, except here it is depicted that that central absorbent member 184 is substantially contiguous with the outer absorbent member 176, being formed from a single mat of absorbent material with partial flow isolation between the two regions provided by insertion of the strips of material forming the wicking barrier 180 between the central region 184 and the outer regions of the absorbent material. Such a configuration could be achieved by forming a fluff mat with strips of barrier material already present, or by inserting sections of barrier material into an already formed or partially formed fluff mat or mat of other absorbent material.

Figure 8:
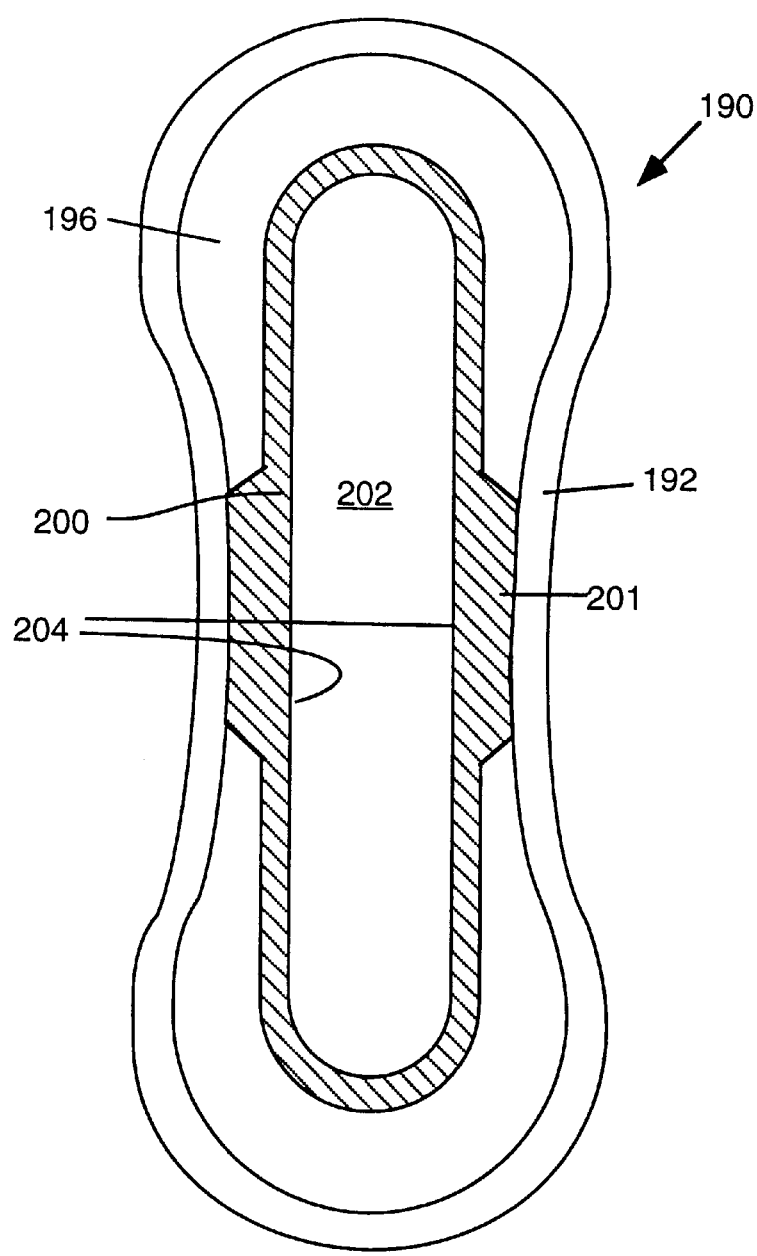
FIG. 8 is a top view of a sanitary napkin having a central absorbent member concentrically surrounded by an outer absorbent member.

When viewed from above with the topsheet removed or translucent, as in FIG. 8, an absorbent article 190 such as a feminine pad or other absorbent article of the present invention can show a loop of wicking barrier material 200 surrounding the central absorbent member 202 and lying within the bounds of a surrounding outer absorbent member 196. The outer absorbent member 196 in this case is said to surround the central absorbent member 202 because, when viewed from above, the outer absorbent member 196 has portions lying outside of the longitudinal edges 204 of the central absorbent member 202. Additionally, as shown in FIG. 8, it can be said that all sides of the central absorbent member 202 are surrounded by the outer absorbent member 196 when viewed from above, but the fact that the outer absorbent member 196 extends beyond the central absorbent member in the transverse direction of the absorbent article when viewed from above is sufficient to meet the requirements of the term "surrounding" as used herein. Indeed, the outer absorbent member need not surround the outer absorbent member along any transverse cross-section, but should surround the central absorbent member in the crotch region of the absorbent article, where leakage is most problematic and where it is most desirable to have an outer absorbent member with a wicking barrier to reduce or prevent fluid transport from the central absorbent member to the outer absorbent member.

The absorbent core of the article 190 in FIG. 8 comprises the central absorbent member 202 and the outer absorbent member 196 and the wicking barrier 200. Beneath the absorbent core is the backsheet 192, which is connected to the topsheet (not shown) and which is larger than the absorbent core to form a rim around the absorbent article.

When viewed from above, as in FIG. 8, the visible portion of the wicking barrier 200 primarily is the horizontal component of the wicking barrier which extends a distance along the body-side surface of the absorbent core. The horizontal component in the crotch region 201 extends to a greater horizontal distance than elsewhere in the wicking barrier, such that the crotch region of the outer absorbent member 196 is substantially covered by the horizontal component of the wicking barrier 200.

Figure 9:
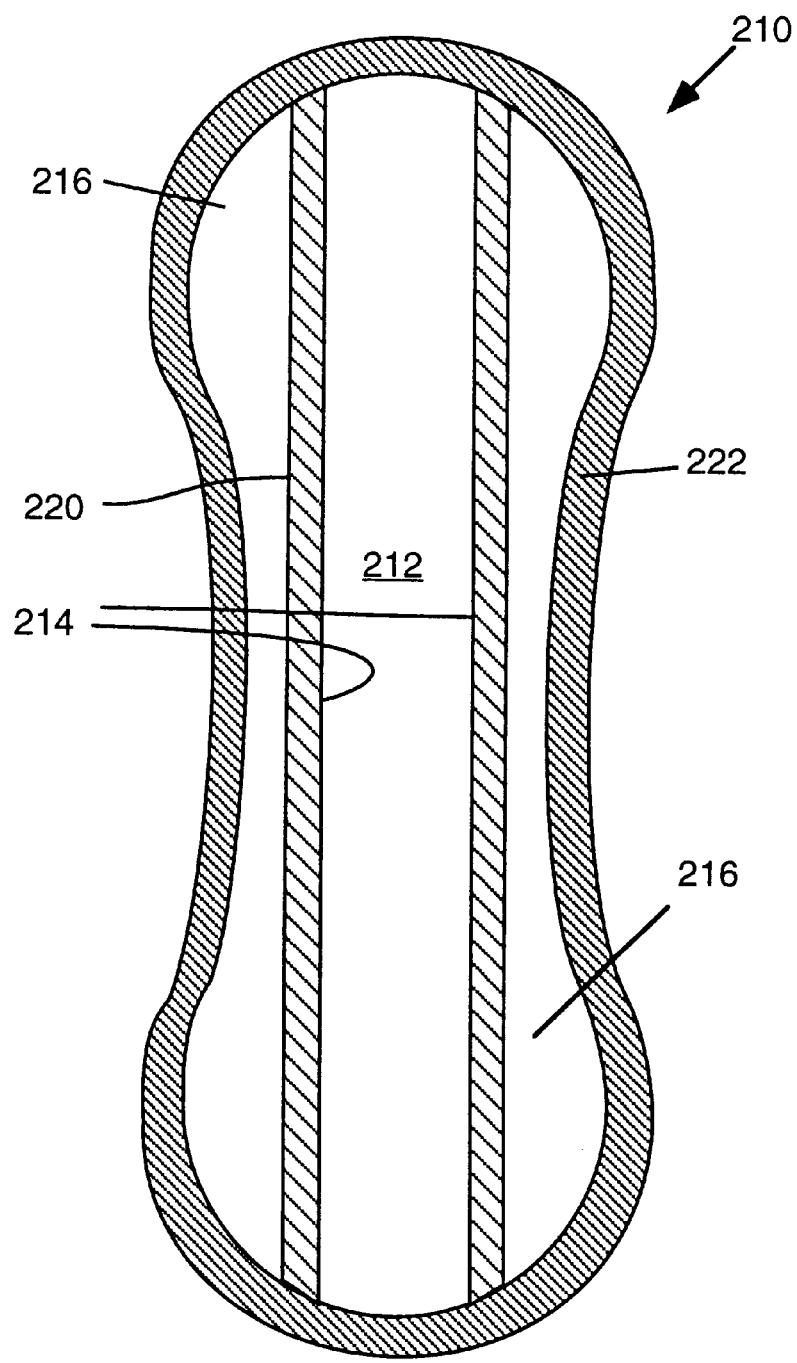
FIG. 9 is a top view of a sanitary napkin having a central absorbent member separated from the outer absorbent member by longitudinal barrier zones.

To achieve the desired reduction in lateral wicking to the edges of the article, it is obviously not necessary for the barrier to form a complete loop around the central absorbent member, as shown in FIG. 9, where a top view of another absorbent article 210 according to the present invention is depicted with the topsheet removed for clarity. The absorbent article 210 in the form of a feminine pad comprises a central absorbent member 212 having longitudinal edges 214, depicted as linear though they can be curved or contoured. The edges 214 of the central absorbent member 212 are separated from the edges of the surrounding outer absorbent member 216 by longitudinal bands of barrier material forming the wicking barrier 220, whose visible horizontal component traverses horizontal distance on the body-side surface of the outer absorbent member 216, and whose vertical component (not shown) spans a vertical distance along the edges of the central absorbent member 212 to reduce lateral wicking flow. The backsheet 222 can extend beyond the outer edges of the outer absorbent member 216, as depicted in FIG. 9, where it is bonded to the topsheet (not shown) and forms a rim around the absorbent core.

Figure 10:
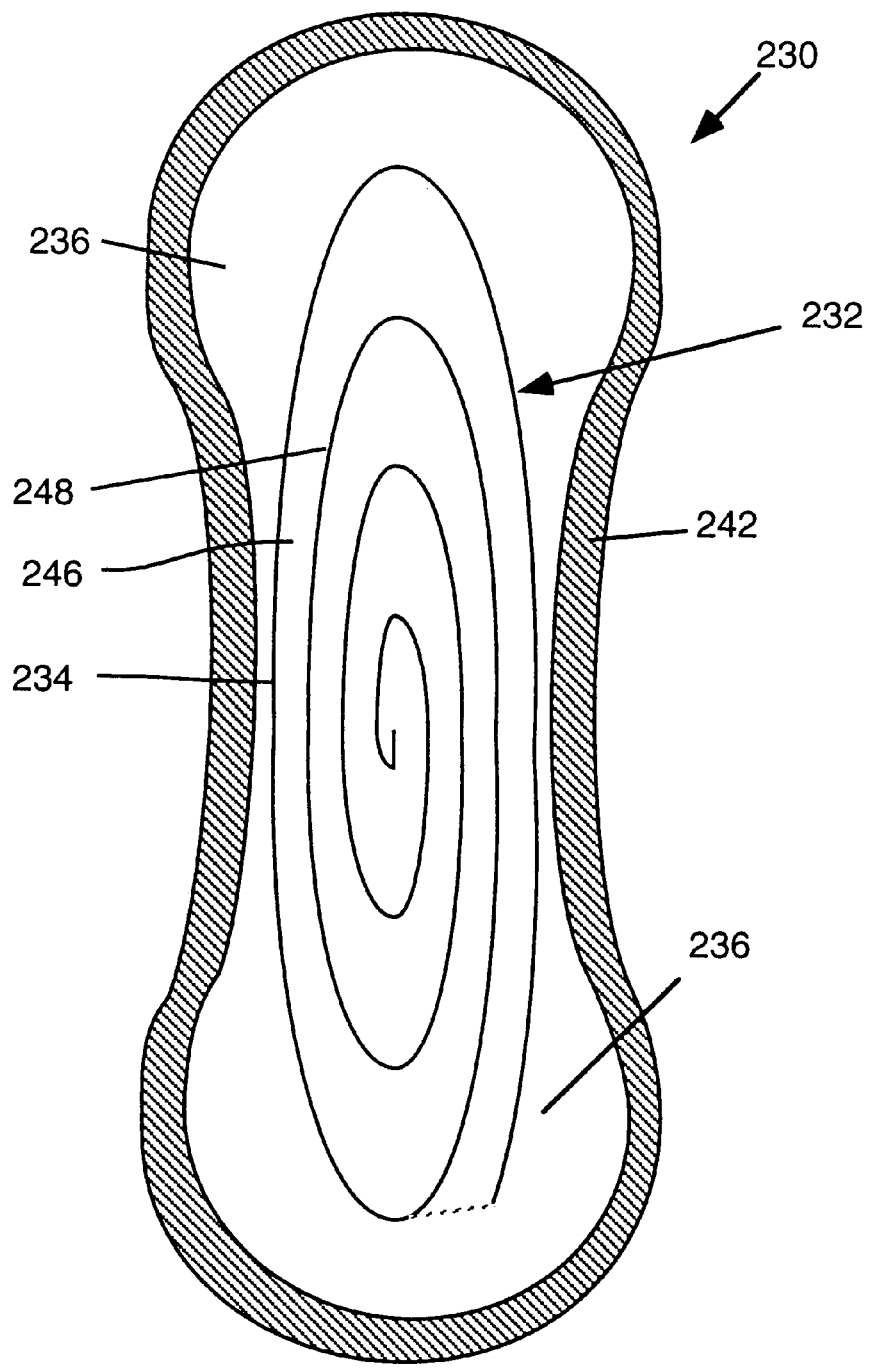
FIG. 10 is a top view of a sanitary napkin comprising a spiral wound composite with barrier material between successive layers.

FIG. 10 shows an embodiment of the present invention wherein an absorbent article 230 comprises an outer absorbent member 236 and a central absorbent member comprising concentric absorbent structure 232 in the form of a spiral wound composite. The spiral wound composite 232 lies inside the outer absorbent member 236 and may reside in a depression therein or on the surface thereof, and has an outer perimeter 234. The spiral wound composite 232 comprises at least one layer of barrier material 248 rolled in spiral form with at least one layer of absorbent material 246. A backsheet 242 is connected to the topsheet (not shown) at the outer periphery of the article 230 and passes under the absorbent core.

Figure 11:
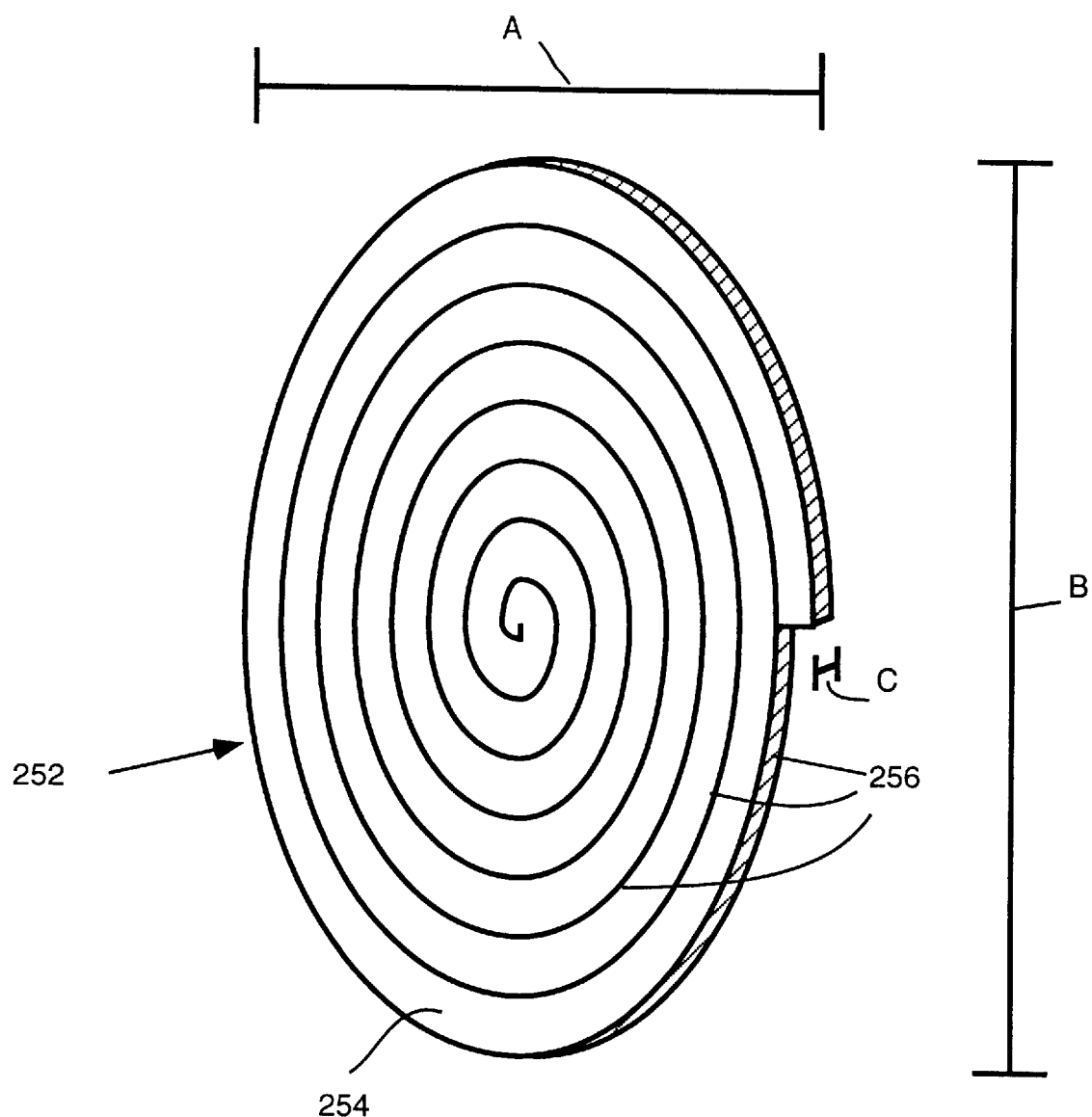
FIG. 11 shows a layer of a spiral wound composite.

Details of a spiral wound composite are shown in FIG. 11. The spiral wound composite 252 comprises substantially concentric alternating rings or windings of barrier material 256 and absorbent material 254. The barrier material 256 can be a continuous strip, as can be the absorbent material 254. The spiral wound composite as depicted in FIG. 11 has a characteristic thickness (z-direction dimension) C, a width A and a length B which can be substantially greater than width A. The z-direction dimension C may be greater than about 1 mm, preferably between about 3 mm and 20 mm, and more preferably between about 4 mm and 15 mm. The in-plane distances A and B may both independently be greater than about 20 mm, preferably greater than about 30 mm, and most preferably between about 25 mm and 100 mm. The concentric absorbent structure can serve as an outer absorbent member or as a component of an outer absorbent member in an absorbent article. In one embodiment, at least one side of the barrier material is not adhesively bonded to any adjacent web, film, or other layer such that the unbonded side of the barrier material can move under physical force relative to the adjacent cellulosic layer to which it is not bonded, thus permitting portions of the concentric absorbent structure to flex out of the plane, similar to a telescoping effect. The "telescoping" ability of the wound layers in the concentric absorbent structure to move in the z-direction relative to one another enables the concentric absorbent structure to conform to the human body when used as a component of an absorbent article for absorbing body fluids. The "telescoping" ability of the concentric absorbent structure also reduces the bending stiffness of the structure because it can yield and flex more easily when subjected to a bending moment or lateral compressive stress. This can be particularly valuable in sanitary napkins for feminine care, where conformability to the body is required for best absorbent performance and protection against leakage.

The absorbent material 254 of the concentric absorbent structure 252 can comprise a cellulosic web that can be formed from any cellulosic papermaking fibers known in the art, including hardwood and softwood, chemically pulped fibers and mechanically or chemimechanically pulped fibers, wood fibers and nonwood fibers such as bagasse, or kenaf. The cellulosic web can be a composite material such as a mixture of cellulose fibers with other materials such as superabsorbent particles, zeolites, activated silica, alumina, baking soda, chitin or chitosan, activated carbon in the form of fibers or granules, anti-microbial agents, thermosetting polymer fibers, latex binder, wet strength agents, surfactants or agents to modify the viscosity of menses or other fluids. Addition of solid particles and fibers into the cellulosic structure is often practical and feasible when airlaying of fiberized pulp and particles is performed. Non-cellulosic fibers can also be added to the aqueous fiber slurry that is used to form a wet laid structure, and some chemical agents such as strength agents can be added to the fiber slurry. Particles can also be added to wet-laid tissue by air entrainment to add particles to the web when it is relatively dry (e.g., over 30% solids and preferably over 60% solids) or particles can be added by other processes known in the art. In one embodiment, materials are coated or printed on a dry tissue web to serve as the absorbent material 254. Desirably, the tissue web is a three-dimensional structure such as a molded uncreped through-dried web, and superabsorbents or others particles or materials can be added adhesively or deposited in pockets of the three-dimensional tissue structure. Exemplary three-dimensional structures suitable for the present invention are disclosed in U.S. Pat. No. 5,429,686 issued to Chiu et al.; U.S. Pat. No. 5,672,248 issued to Wendt et al.; U.S. Pat. No. 5,607,551 issued to Farrington et al.; and U.S. Pat. No. 5,048,589 issued to Cook and Westbrook.

The barrier material between successive layers of absorbent material in the multi-layered structure (layered with respect to the radial direction) can have a low coefficient of friction to permit easy flexing and deformation of the spiral wound composite in the thickness direction to enhance the previously mentioned telescoping effect in which the centermost portions become more elevated than the surrounding regions.

The spiral wound composite can function in an absorbent article as an absorbent layer, as a central absorbent member in a void or depression of a surrounding outer absorbent member, or as an outer absorbent member.

Figure 12:
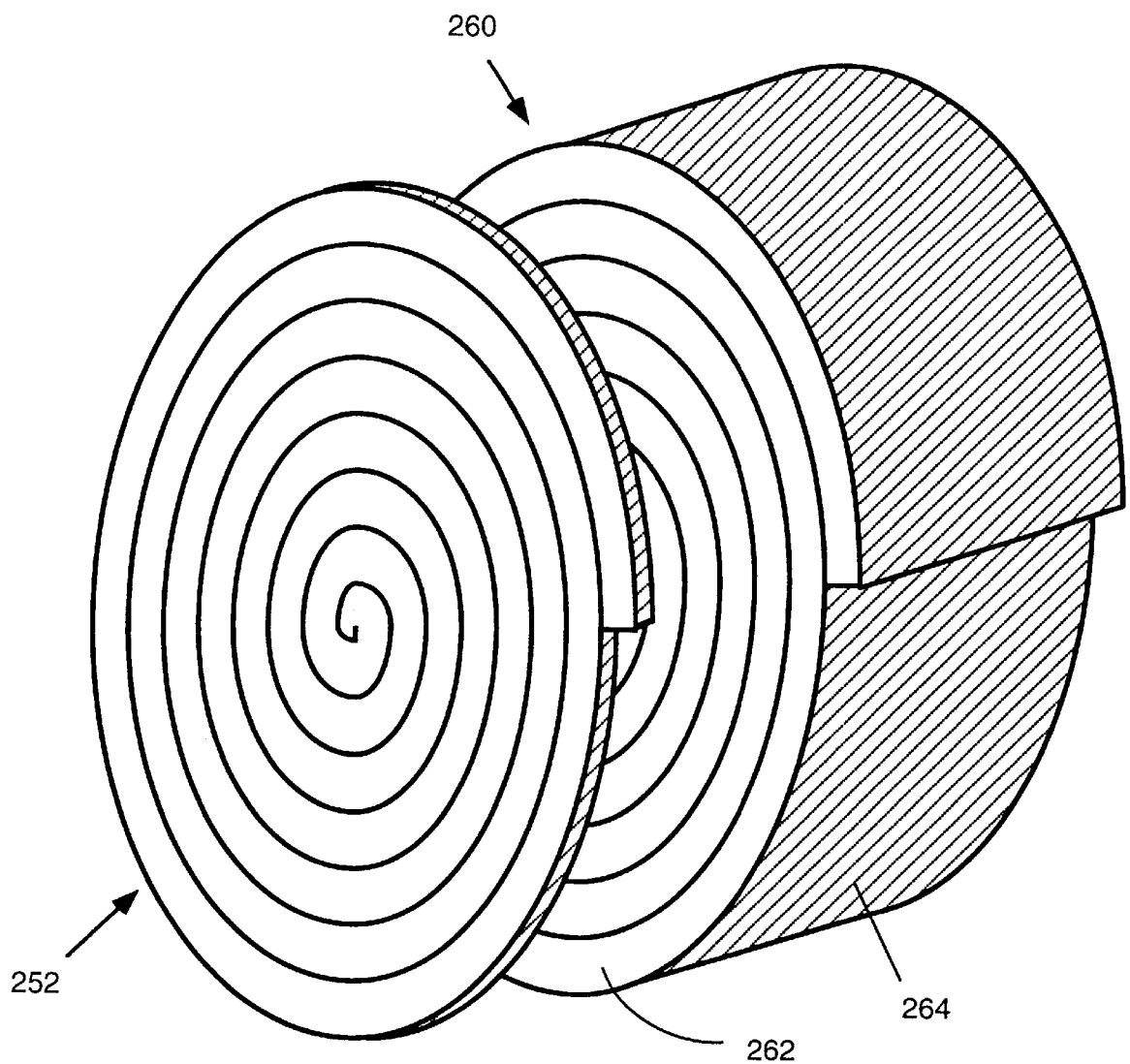
FIG. 12 shows a spiral wound roll from which a spiral wound composite is cut.

FIG. 12 illustrates one aspect of a method of producing a spiral wound composite 252, which is cut from a roll 260 formed by rolling a layer of barrier material 264 on which an absorbent web 262 of desirably cellulosic material has been placed. When wound, the barrier material desirably forms the outer surface of the roll. Cutting or slicing a slice from the roll substantially normal to the axis of the roll yields a spiral wound composite layer.

The slicing or cutting can be performed with high speed circular saws, including diamond saws and the rotating-arm circular saws commonly used to slice logs of wound bath tissue into individual rolls of bath tissue. Cutting by means of high velocity water jets, band saws, guillotine cutters, or wire saws can be done as well.

More than one layer of tissue can be used. For example, a parent roll can be formed by placing two or more plies of tissue on top of a barrier material in the form of a web or film and then rolling said two or more plies of tissue and said barrier material to form a single roll from which concentric absorbent structures can be cut or sliced. Multiple plies of tissue in each band disposed between bands of barrier material can enhance the absorptive properties of the concentric absorbent structure by providing additional interply pore space for wicking and fluid intake. Particularly when wet resilient uncreped, through air dried structures are used with a high degree of molding, the interply contribution to fluid permeability can be significant, as disclosed by Chen et al. in the copending U.S. application of Chen et al., Ser. No. 08/912,906, "Wet Resilient Webs and Disposable Articles Made Therewith," filed Aug. 15, 1997.

The barrier material can be any material which can be used to hinder wicking from one absorbent layer to the next in the wound spiral structure (i.e., it reduces radial wicking of fluid); alternatively, the barrier material may be selected primarily for its ability to reduce friction between adjacent cellulosic layers to enable a telescoping effect for good body conformability. Preferably, the barrier material provides both reduced radial wicking and reduced friction between neighboring cellulosic layers. Materials suitable as barrier materials include smooth polymeric films such as polyolefins, cellophane, or vinyl, preferably having adhesive on one side to attach to the cellulose.

The barrier material can also comprise waxes, adhesives, latexes, sealants, hydrophobic powders, and other hydrophobic materials applied to one surface of the tissue web to provide the desired barrier function. For example, waxes may be applied to selected portions of a tissue web to provide the desired gradient effect, with a partially permeable wax coating applied to regions of the web that will comprise the center of the concentric absorbent structure, and a more impermeable coating applied to regions of the tissue that will be near the outer edge (outer bands) of the concentric absorbent structure. In one embodiment, the application of hydrophobic matter to a three-dimensional tissue web can be practiced according to any of the methods disclosed in the commonly owned copending U.S. application Ser. No. 08/997,287, "Dual-zoned Absorbent Webs," filed Dec. 22, 1997, by Chen et al.

The spiral-wound parent roll can be shaped into a variety of forms other than circles or ovals. For example, it can be shaped to be substantially rectangular or triangular in cross-section. For effective shaping, the central portion of the parent roll may need to be hollow to provide void space for collapse of portions of the concentric absorbent structure to assume the desired shape. Providing a central space in the parent roll can be done by winding the tissue and barrier material about a roll or shaped bar having relatively low friction, such as a bar coated with polytetrafluoroethylene, and then removing the bar from the parent roll after winding is complete. The parent roll may then be shaped by compression of the sides to yield the desired shape.

Figure 13:
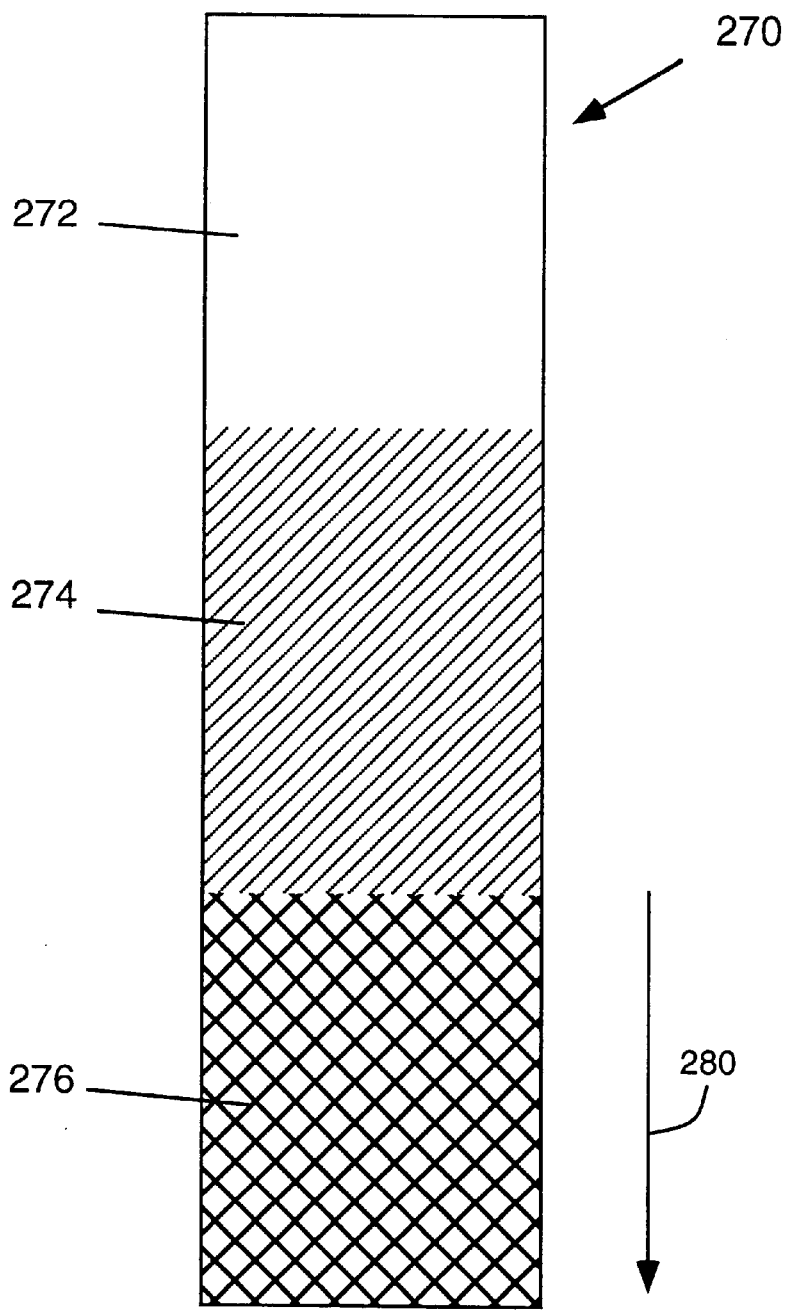
FIG. 13 shows a length of heterogeneous barrier material having multiple permeability or wicking zones for use in a spiral wound composite.

The barrier material can vary in its properties with radial distance from the center of the spiral wound composite by using a heterogeneous web of barrier material as illustrated in FIG. 13. The length of barrier material 270 comprises three zones having different properties, a first zone 272, a second zone 274, and a third zone 276. The length of barrier material 270 will be wound while adjacent to a layer of absorbent material (not shown) in the direction shown by arrow 280, resulting in a roll with the first zone 272 at the most central portion of the roll, the second zone 272 in the intermediate portion of the roll, and the third zone 276 at the outermost portion of the roll. The first zone 272 can be substantially permeable or apertured to permit radial flow of fluid in the concentric absorbent structure formed by the spiral wound composite. Desirably, the second zone 274 provides increased resistance to radial fluid flow in a spiral wound composite and the third zone 276 can be substantially impermeable or have a permeability or porosity or degree of wettability substantially less than that of the second zone 274 to provide increased impedance to lateral flow, especially radial wicking, in the spiral wound composite as used in an absorbent article.

A heterogeneous film or web used as a barrier material need not have step changes in material properties, as shown in FIG. 13, but may have gradual gradients, or may have less than or more than the three distinct zones shown.

Such gradients or changes in material properties along the length of a barrier material can be made by adding holes or pores in the material, particularly when it is a film, in varying degree over a finite length. For example, pores or holes of varying size or number density may be provided in a film by punching, stamping, perf-embossing, chemically etching, laser drilling, needling, slitting, or ultrasonically perforating. Desirably, any holes or perforations added to the film have dimensions smaller than the z-direction thickness of the concentric absorbent structure (thickness C in FIG. 11) such that the barrier material remains continuous in the concentric absorbent structure after it has been sliced or cut off of the wound parent roll. Alternatively, the barrier material need not be continuous in the concentric absorbent structure if it is fixedly attached to the cellulosic web, such as by adhesively joining the film or other barrier material to a tissue web or airfelt layer prior to cutting or slicing off concentric absorbent structures.

Figure 14:
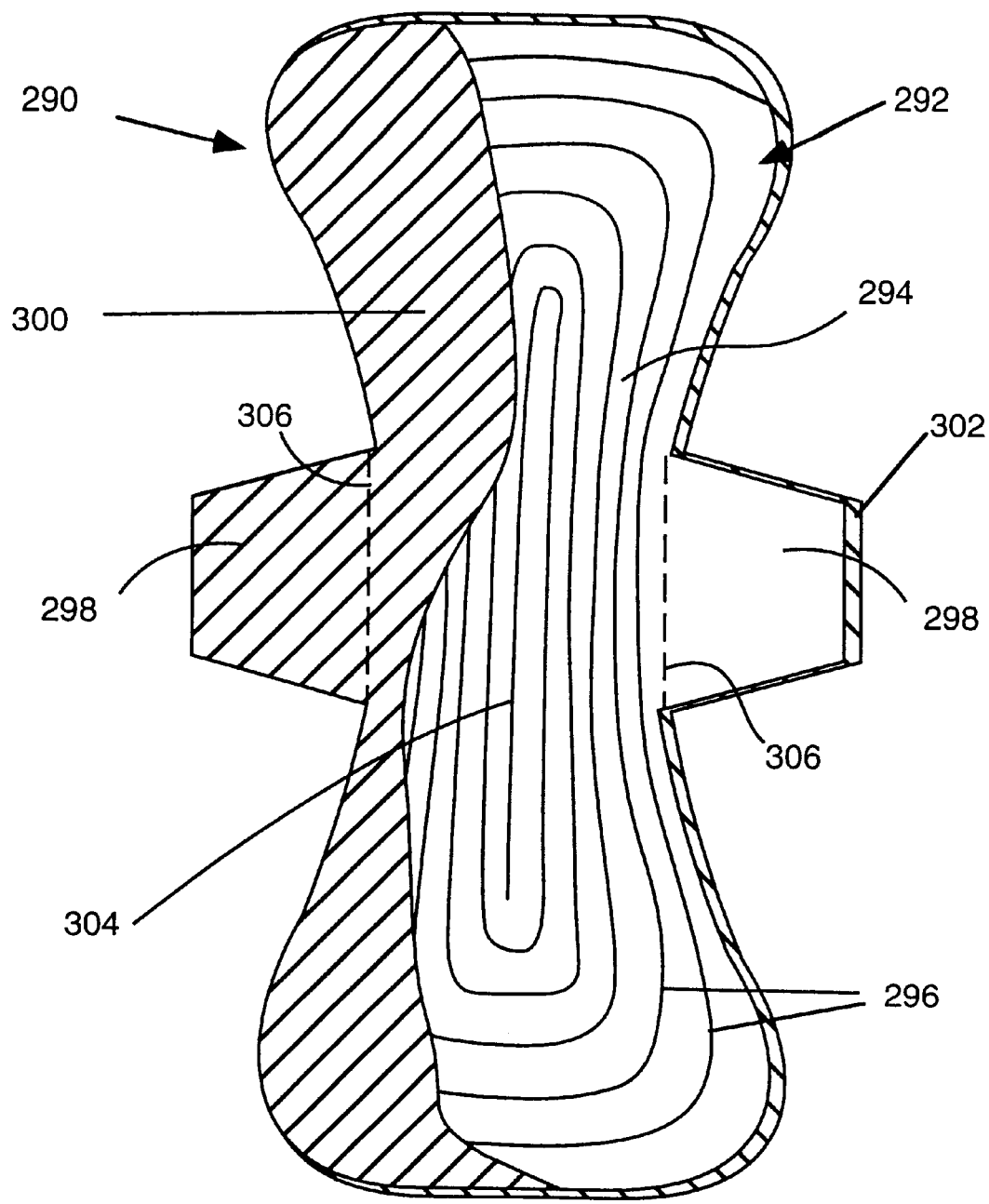
FIG. 14 shows a feminine care pad with wings having a shaped spiral wound composite layer.

FIG. 14 depicts a cutaway view of sanitary napkin 290 for feminine care as an exemplary absorbent article comprising a shaped concentric absorbent structure 292, which is a spiral wound composite in this embodiment. As with many absorbent articles for absorbing body fluids known in the art, sanitary napkin 290 comprises an impervious backsheet 302 and a soft, liquid pervious topsheet 300. The topsheet 300 can be a thin nonwoven web comprising polyolefin fibers or an apertured film or a composite topsheet such as those of Chen et al. in commonly owned U.S. patent application Ser. No. 08/997,287. Topsheet 300 is depicted in a cutaway view to reveal the absorbent internal layer comprising a concentric absorbent structure 292 deposed between said impervious backsheet 302 and said topsheet 300. The concentric absorbent structure 292 comprises a spiral wound composite located in the main target area of the absorbent article 290 where the highest influx of body fluids are expected. The absorbent internal layer may further comprise multiple layers or portions of other absorbent material, including fluff pulp, air laid strips, meltblown strips, or superabsorbent particles.

When fluid contacts the concentric absorbent structure 292 near its center, it is preferentially wicked in the z-direction, with relatively less wicking occurring in the radial direction. If the barrier material 296 is desirably porous near the center of the concentric absorbent structure 292 and relatively impervious near the outer edges of the structure, then radial wicking from one layer of the absorbent material 294 to the next in the spiral wound composite 292 can occur in the central regions of the structure for effective distribution of the fluid but radial wicking is impaired for fluid near the edges of the structure to reduce the risk of leakage.

FIG. 14 also depicts the presence of wings 298 on the sides of the absorbent article 290 for attachment of the article to the wearer's undergarments. The concentric absorbent structure 292 may extend to the bending lines 306 where the wings 298 fold. In this embodiment, the concentric absorbent structure 292 is shown to be shaped to more fully correspond to the shape and size of the absorbent article 290, resulting in more efficient use of space. Essentially all of the central absorbent member or outer absorbent member can be comprised by the spiral wound composite 292 when so shaped. To form the shaped spiral wound composite as shown, the absorbent material 294 and the barrier material 296 would not be wound into a circular structure, but would be folded successively over a flat length of the composite that forms the first band 304 in the center of the concentric absorbent structure.

Figure 15:
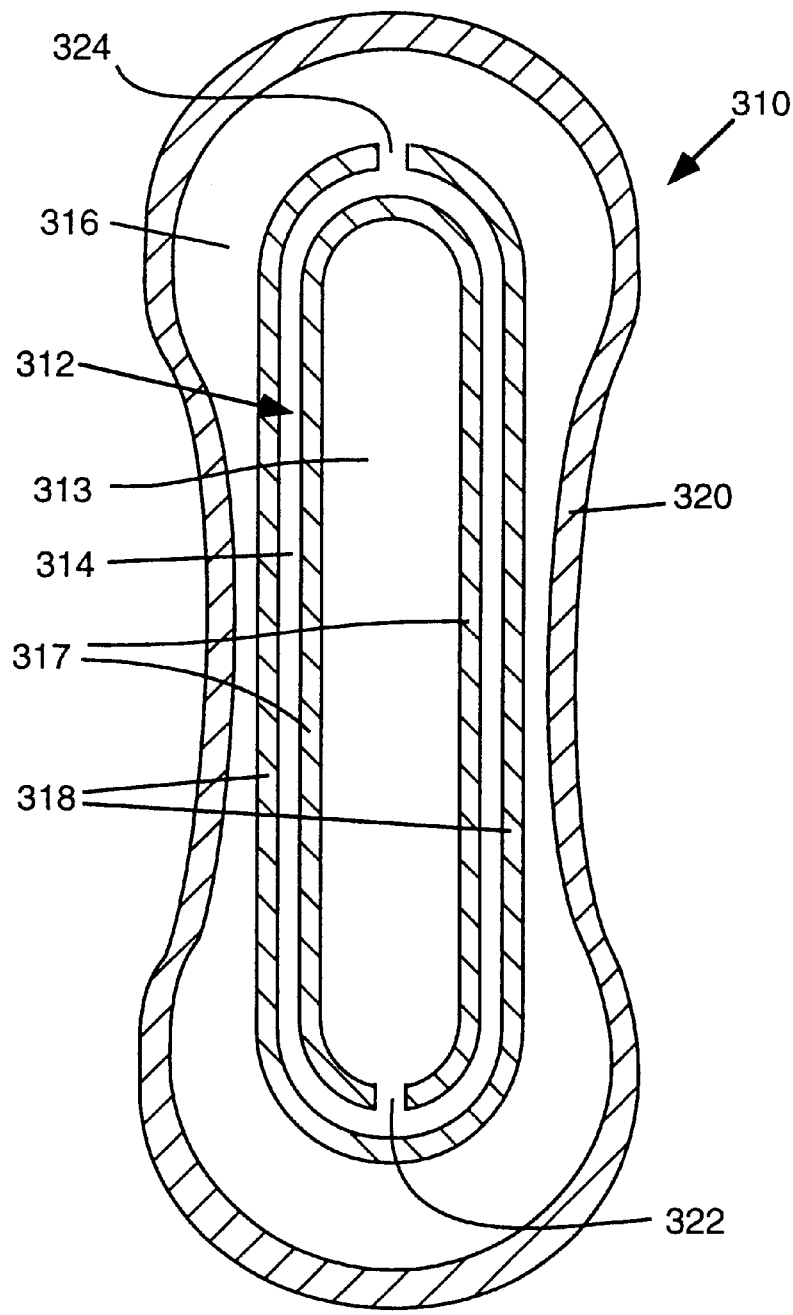
FIG. 15 shows a top view of a sanitary napkin with multiple wicking barriers arranged to provide a labyrinth-like tortuous pathway for radially outward wicking from the target area of the central absorbent member.

FIG. 15 shows a top view of a sanitary napkin 310 having a central absorbent member 312 surrounded by an outer absorbent member 316 with multiple wicking barriers 317, 318 arranged therebetween to provide a labyrinth-like tortuous pathway in the plane of the article for fluid from wicking out from the target area of the central absorbent member 312. Both wicking barriers 317, 318 comprise a vertical component (not shown) extending vertically into the thickness of the absorbent article and a horizontal component (the visible part of wicking barriers 317, 318) extending a horizontal distance along the body-side surface of the outer absorbent member 316. The wicking barriers 317, 318 may be attached to the topsheet (not shown for clarity), which in turn is attached to the backsheet 320 at the periphery of the article 310. The inner wicking barrier 317 forms a ring around the inner portion 313 of the central absorbent member 312. Fluid can flow in the plane of the article from the inner portion 313 to the outer portion 314 of the central absorbent member 312 via a first opening 322 in the inner wicking barrier 317 located at a transverse edge of the inner portion 313 of the central absorbent member 312. From the outer portion 314 of the central absorbent member 312, fluid can further flow to the outer absorbent member 316 via a second opening 324 in the outer wicking barrier 318. The tortuous in-plane pathway from the center of the inner portion 313 of the central absorbent member 312 to the outer absorbent member 316 permits the absorbency of the outer absorbent member 316 to be available to fluid in the absorbent article 310, but only when the central absorbent member 312 has been sufficiently wetted to permit wicking flow across the long, tortuous pathway so established. Additional pathways may be provided by apertures (not shown) in the wicking barriers 317, 318 remote from the body-side surface of the article.

Figure 16A:
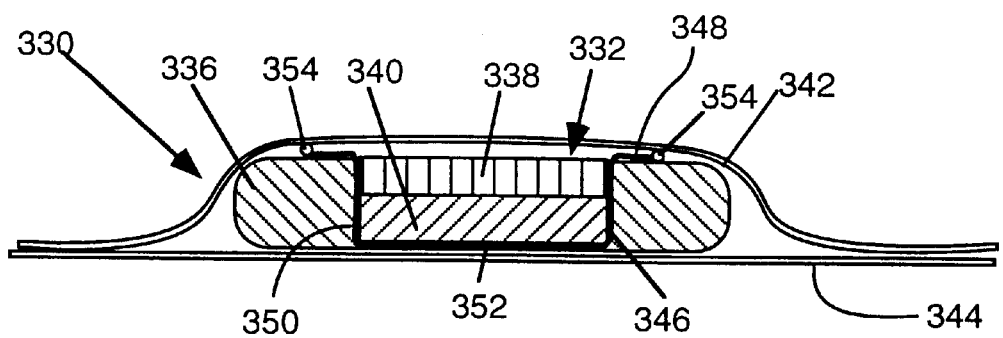
FIG. 16 shows a cross-section of an absorbent article according to the present invention wherein the central absorbent member can expand substantially when wetted.
Figure 16B:
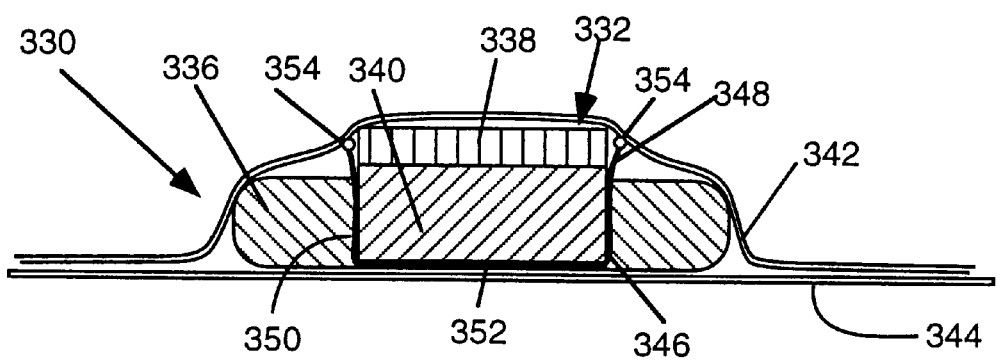

FIGS. 16A and 16B show a cross-section of an absorbent article 330 according to the present invention wherein the central absorbent member 332 can expand substantially when wetted. As in several other embodiments, the central absorbent member 332 resides in a hole defined within an outer absorbent member 336. The central absorbent member 332 comprises two layers, and upper intake layer 338 and a swelling layer 340 which can expand substantially in the vertical direction upon being wetted. The central absorbent member 332 is lined by a wicking barrier 346, desirably a flexible, substantially impervious polymeric film, comprising a vertical component 350, a horizontal component 348 on the surface of the outer absorbent member 336, and a lower portion 352 beneath the central absorbent member 332 and in contact with the backsheet 344. The wicking barrier 346 is attached to the topsheet 342 by adhesive 354. FIG. 16A depicts the article 330 prior to being wetted. FIG. 16B depicts the article 330 after wetting, when the swelling layer 340 has taken in enough fluid to expand. significantly and modify the fit of the article 330 against the wearer's body. The central absorbent member 332 has been elevated by virtue of the expanding layer 340, resulting in improved contact with the body at a time when the absorbent material might otherwise be collapsing and providing less fit against the body. Sections or cubes cut from compressed chemithermomechanical pulp (CTMP), such as compressed flash-dried bales of softwood bleached chemithermomechanical pulp (BCTMP), are capable of expanding five to eight times their initial thickness when wetted and can be useful in the absorbent article 330. Superabsorbents or mixtures of superabsorbents and cellulose, compressed chemically crosslinked fibers, calendered uncreped through-air dried sheets, compressed sponges of regenerated cellulose, or other materials can also be used to form the expanding layer 340.

Figure 17:
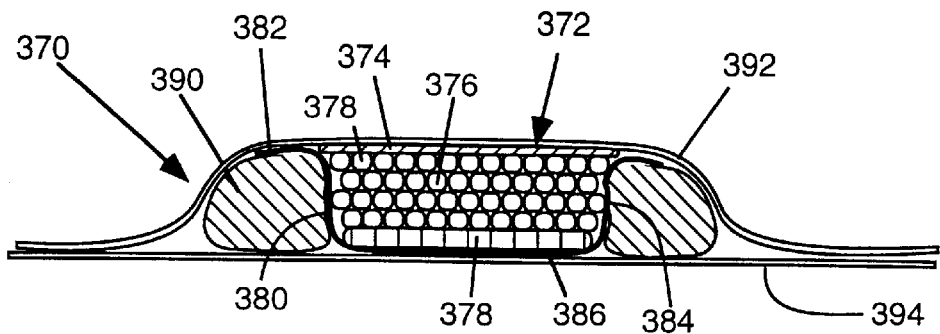
FIG. 17 shows a cross-section of an absorbent article according to the present invention wherein the central absorbent member comprises multiple longitudinal bands of absorbent material for improved wicking in the longitudinal direction.

FIG. 17 shows a cross-section of an absorbent article 370 according to the present invention with a central absorbent member 372 deposed in a central void of an outer absorbent member 390 between a topsheet 392 and a backsheet 394. The central void of the outer absorbent member 390 passes completely through the outer absorbent member 390. A wicking barrier 380 separates the two absorbent members 372, 390. The wicking barrier 380 comprises a vertical component 384, a horizontal component 382, and a backsheet-contacting component 386 between the central absorbent member 372 and the backsheet 394. The central absorbent member 372 comprises a top intake layer 374, which may be a tissue layer or other absorbent material adapted for rapid intake of fluid, a longitudinal wicking layer 376, and a lower fluid retention layer 378, which may comprise superabsorbent material, densified pulp fibers, microstrained pulp sheets, tissue, coform, or peat moss. The longitudinal wicking layer 376 comprises a plurality of absorbent strips or filaments 378. The strips or filaments can comprise elongated sponge elements, such as those of U.S. Pat. No. 4,490,147, issued Dec. 25, 1984 to Pierce et al., herein incorporated by reference, or absorbent fibers, desirably in tow form or in twisted or braided form having a preferential fiber orientation in the longitudinal direction of the article to promote wicking and fluid transport in the longitudinal direction. The elements can have cross-sectional dimensions less than about 10 mm, desirably less than about mm, and can have a length of 50 mm or greater, more specifically 100 mm or greater. The longitudinal wicking layer 376 can also provide low stiffness and good conformability due to deformation or motion of the filaments 378 relative to each other during compression or bending. In one embodiment, the longitudinal wicking layer 376 can be prepared from a wet resilient material such as uncreped through-air dried tissue or meltblown webs treated for hydrophilicity, which has been cut into longitudinal strips or sufficiently provided with slits to serve as individual filaments or strips running in the longitudinal direction. Desirably, the material used in the longitudinal wicking layer 376 has a fiber orientation that is distinctly preferential in the longitudinal direction.

The horizontal component 382 of the wicking barrier 380 may completely cover the body-side surface of the outer absorbent member 390 or may cooperate with the backsheet 394 to completely wrap or encase the outer absorbent member 390 with substantially impervious material.

Figure 18A:
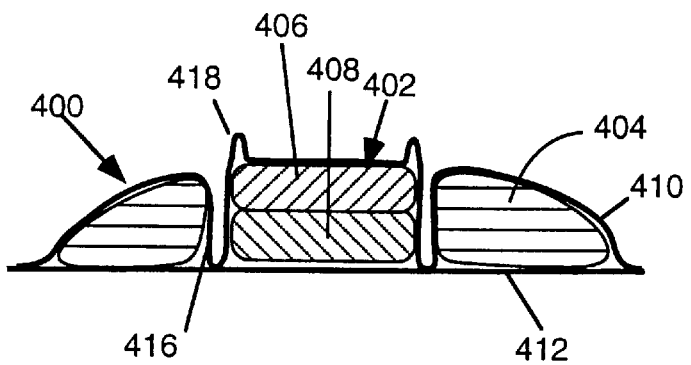
FIG. 18 shows cross-sections of an absorbent article comprising a protruding loop of cover material to form a runoff barrier near the periphery of the central absorbent member.
Figure 18B:
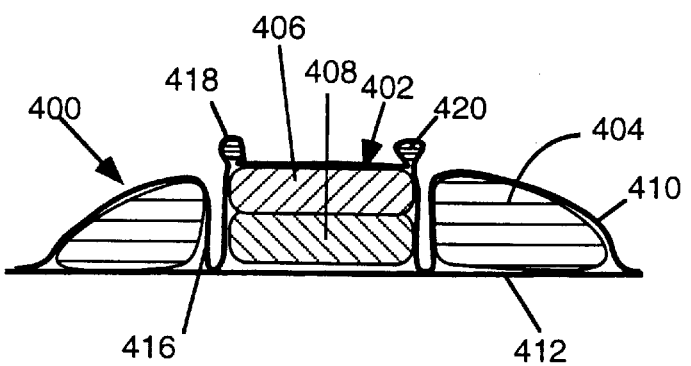

FIGS. 18A and 18B show cross-sections of an absorbent article 400 comprising a central absorbent member 402 with an upper layer 406 and a lower layer 408, surrounded by an outer absorbent member 404 split into two segments by a central void. A nonwoven or apertured film topsheet 410 also serves as a wicking barrier. A downward loop 416 of the topsheet 410 separates the central absorbent member 402 from the outer absorbent member 404 and desirably extends to contact the backsheet 412, as depicted, where it is attached for good integrity. On the body-side surface, a protruding loop 418 of the topsheet 410 forms a runoff barrier near the periphery of the central absorbent member 402. In FIG. 18A, the protruding loop 418 is air filled, while in FIG. 18B, the protruding loop 418 is filled with a soft, pliable material 420 such as a strip of a lofty nonwoven web, loose hydrophobic fibers, a yarn, or a pliable foam. A filled protruding loop can improve the gasketing effect of the runoff barrier and improve conformability to the body. Desirably, the topsheet 410 is treated to be less wettable and/or less permeable in the loop regions 416,418 than elsewhere on the topsheet 410. Such treatment can be achieved by coating with water repellents, heat treating to seal pores in the topsheet, or by addition of impervious material to the loop regions 416, 418.

FIGS. 19A and 19B show cross-sections of an absorbent article 430 comprising multiple protruding loops 441, 443, 445 of cover material from the topsheet 436 to form runoff barriers on the body-side surface of the article. The article 430 comprises a central absorbent member 432 occupying a complete central void within an outer absorbent member 434 such that the outer absorbent member 434 is completely segregated into two sections, at least when viewed in transverse cross-sections as shown near within the crotch region of the article. The central absorbent member 432 is segregated from the outer absorbent member 434 by a wicking barrier 440 comprising a horizontal component defining a ledge 442, a vertical component 444, and an optional underlying component 446 beneath the central absorbent member facing the backsheet 438. Longitudinal folds in the topsheet 436 create longitudinal protruding loops 441, 443, 445 that act as runoff barriers, one of which runoff barrier 445 is within the perimeter of the central absorbent member 432, another of which runoff barriers 443 at least partially overlaps the boundary between the central absorbent member 432 and the outer absorbent member 434, and another of which runoff barrier 441 is disposed above the outer absorbent member 434 towards the longitudinal sides 450 of the article. In FIG. 19A, the loops 441, 443,445 are air-filled, while in FIG. 19B loop 443 is filled with a soft, pliable material 447 such as a strip of a lofty nonwoven web or a pliable foam to better serve as a gasket and body fit element.

Loop 443 could also comprise multiple folds of the topsheet 436 material to provide a structure of increased bulk, thickness, and resiliency. Examples of loops comprising multiple folds of material are shown in FIGS. 20A and 20B, respectively, where a spiral-wound loop 450 is shown as well as pleated loop 452. Many other geometrical configurations could be used, with or without additional materials enclosed within the loops for softness, resiliency, and comfort.

In embodiments with a runoff barrier formed by a pleat or fold of material from the topsheet, it is desirable that there be at least two longitudinal runoff barriers superposed over at least a portion of the boundary between the central absorbent member and the outer absorbent member. The runoff barrier can be considered to be superposed over the boundary if any portion of the runoff barrier is within about 4 mm of the boundary.

FIGS. 21–32 are discussed in the Examples below.

EXAMPLES

Several examples of absorbent articles were made with the materials listed in Table 1 below:

TABLE 1

Basic materials used in construction of absorbent articles for the Examples.

| Component | Manufacturer | Description |
| --- | --- | --- |
| Topsheet | | |
| Spunbond material | Kimberly-Clark Corp. | 0.6 osy polypropylene spunbond web, "Delta" version, treated with 0.3% add-on of surfactant (described below) |
| Surfactant treatment | ICI Americas, Inc | 45% (w) polyethoxlated hydrogenated ethoxylated castor oil; 55% (w) sorbitan monooleate |
| Adhesive | National Starch and Chemical Co. | NS-34-5610: slot-coated, pinstripe pattern, applied at a level of about 5 gsm or less. |
| Fluff | Kimberly-Clark Corp. | Coosa River CR56 debonded softwood pulp comminuted with a hammermill |
| Densified airlaid webs | | |
| Completed web | Concert Fabrication Ltee | 90% softwood fibers and 10% binder fibers with overall densities of 0.1–0.2 g/cc. |
| Fibers | Weyerhaeuser Co. | NB-416: bleached southern softwood kraft |
| Binder fibers | Hoechst Celanese Corp. (Trevira Company) | Celbond #255: PET core, activated co-polyethylene sheath, 50/50 core/sheath ratio, concentric, 2.8 dpf, with T-255 fiber finish |
| Impervious wicking barrier | | |
| Polyolefin film, colored | Edison Plastics Co. | A low density polyethylene, 20 gsm, rose color, 1 mil initially, 2 mil gauge after embossed with pattern MFST (male fine square taffeta), contact adhesive on one side |
| Polyolefin film, white | | Low density polyethylene, 18 gsm, opaque with added white pigment, about 1 mil |
| Pervious wicking barrier | | |
| Spunbond web | Kimberly-Clark Corp | 0.8 osy 2.7 denier, rose color, no surfactant |
| Backsheet | | |
| Polyolefin film | Edison Plastics Co. | A low density polyethylene, 20 gsm, rose color, 2 mil gauge after embossed with pattern MFST (male fine square taffeta), coated with contact adhesive on one side |
| Adhesive | National Starch and Chemical Co. | NS-34-5610, less than 15 gsm added, slot-coated, pinstripe pattern |
| Garment adhesive | National Starch and Chemical Co. | NS-34-5602, less than 45 gsm applied, slot coated, two 15 mm side lines of adhesive with a 19 mm space between them |

TABLE 1-continued

Basic materials used in construction of absorbent articles for the Examples.

| Component | Manufacturer | Description |
| --- | --- | --- |
| Release paper | Akrosil Inc. | White base sheet, one side coated with silicone release agent, other side printed |

Examples 1–7

Figure 21:
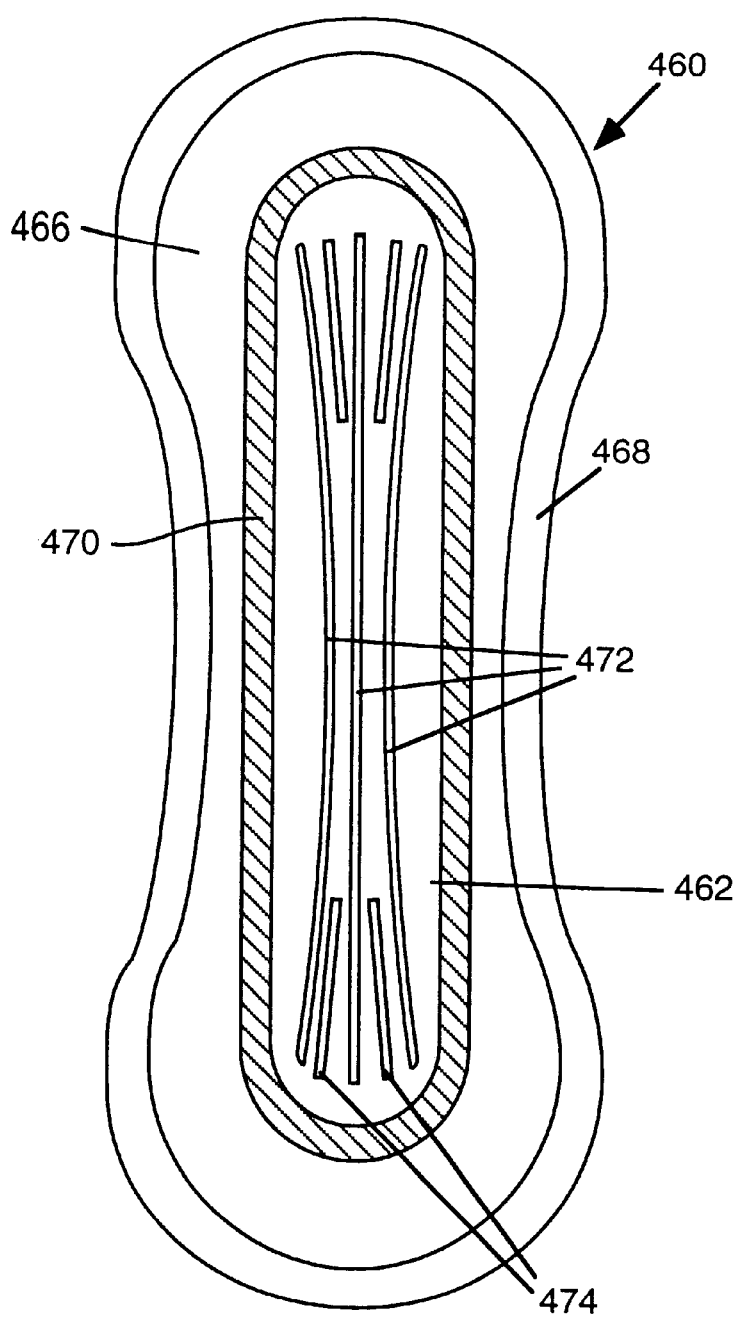
FIG. 21 shows the top view of several sanitary napkins described in the Examples, also showing embossed lines.

Example 1 and other examples described herein were made to have a top view appearance according to FIG. 21. FIG. 21 depicts a central absorbent member 462 surrounded by a hydrophobic ledge 470 and a larger absorbent member 466, which may be an outer absorbent member having a central void or depression or an underlying absorbent member without a central void or depression. The absorbent core comprising the central absorbent member 462 and the outer or underlying absorbent member 466 are enclosed by an underlying backsheet 468, with larger dimensions than the absorbent core to form a rim therearound, and a topsheet (not shown) which is attached to the backsheet 468 at the rim. Optionally, the central absorbent member 462 can be provided with embossed lines as shown in FIG. 21 comprising three long lines 472 and four short lines 474 each about 2 mm wide and approximately 0.4 mm deep.

Example 1 was a control pad made without a vertical wicking barrier but with a horizontal wicking barrier; i.e., with a polymeric film disposed horizontally between two superposed absorbent layers. Thus, in Example 1, the horizontal ledge 470 is the exposed horizontal component of a purely horizontal wicking barrier (the impervious wicking barrier of Table 1) which lies in a plane between an upper central absorbent member 462 and an underlying outer absorbent member 466, which is merely a planar absorbent member which lies beneath the central absorbent member (in other examples according to the present invention, the outer absorbent member has a central void into which the central absorbent member is inserted).

In Example 1, a 175 gsm airlaid densified web (as described in Table 1) served as the lower layer of the absorbent core, i.e., as the outer absorbent member 466 but without a central void or depression. The 175 gsm airlaid outer absorbent member was cut to a dumbbell shape with a length of about 21.5 cm and a width at the transverse centerline of about 6 cm. The dumbbell-shaped outer absorbent member was placed on the backsheet (as described in Table 1) comprising a polymer film provided with contact adhesive. Over the central portion of the outer absorbent member of the control samples was placed a cut rounded rectangular section of spunbond film (the same material as the pervious wicking barrier of Table 1) to serve as a horizontal wicking barrier. The horizontal wicking barrier had a length of 20.3 cm and a width of 4.7 cm. Above the horizontal wicking barrier was placed a rectangular rounded central strip of a densified airlaid web having dimensions smaller than the cut spunbond film (18.7 cm long and 3.7 cm wide). The densified airlaid strip was as described in Table 1, with a density of about 0.1 g/cc and a basis weight of about 175 gsm. This central strip was provided with the curved embossing lines depicted in FIG. 21 while the underlying outer absorbent member remained unembossed. A slit about 10 cm long was provided through the longitudinal center of the central strip in the longitudinal axis. The spunbond topsheet as described in Table 1 was then placed over the entire article, with edges extending well beyond the outer absorbent member. The laminated structure was then cut with a dumbbell-shaped die having dimensions greater than the outer absorbent member (24.4 cm long, 8 cm wide at the transverse centerline) to provide a rim of backsheet material and cover material around the outer absorbent member in an absorbent article having good integrity provided in part by the contact adhesive on the polymeric film. After cutting, the pad was heat-embossed to provide several embossing lines in the central strip of the pad as shown in FIG. 21.

For Examples 2 to 5, feminine pads according to the present invention were made generally following the procedures above for Example 1, with the exceptions that 1) a central region of the outer absorbent member was removed by a die cutting operation to provide a central void in the outer absorbent member having substantially the same dimensions as the central absorbent member (about 18.7 cm long and 3.7 cm wide); 2) a cut polymer film (the rose-colored impervious wicking barrier of Table 1) die cut to be a rounded rectangle 20.3 cm long by 4.7 cm in width was placed over the central void, replacing the similarly shaped spunbond web of Example 1, thus serving as a barrier material for a wicking barrier; and 3) an absorbent insert having a shape and dimensions essentially the same as the central void was placed over the cut polymer film to define a central absorbent member in the void surrounded by the remaining portions of the outer absorbent member.

After the topsheet was attached and the entire article was die cut to provide a sealed article having a rim of backsheet and topsheet material surrounding the outer absorbent member, a ring of the colored barrier material was visible through the translucent topsheet (the horizontal component of a vertical wicking barrier). The articles were also heat embossed as with the control to provide several substantially longitudinal embossment lines in the central absorbent member.

Several different combinations of material were used to produce the central absorbent member. For most examples, the lower layer of the central absorbent member consisted of the 175 gsm outer absorbent member material that was cut out of the outer absorbent member while providing a central void therein.

In Example 2, the central absorbent member comprised an upper layer consisting of a 250-gsm densified airlaid mat (as described in Table 1) having a density of 0.14 g/cc and a lower layer consisting of the cut-out portion from the 175-gsm airlaid material of the outer absorbent member having a density of about 0.1 g/cc which was previously removed to provide a central void. As with the control sample (Example 1), the upper layer of the central absorbent member was embossed and provided with a longitudinal slit.

In Example 3, the upper portions of the central absorbent member comprised two layers of an uncreped through-air dried tissue of spruce BCTMP pulp each having a basis weight of 30 gsm and added permanent wet strength agent (Kymene added at about 50 pounds per ton of fiber), molded onto a Lindsay Wire T-116-3 through-air drying fabric and produced with about 27% rush transfer onto a Lindsay Wire T-216-3 transfer fabric (i.e., 27% differential velocity in going from a forming fabric to the textured transfer fabric, from which it was then transferred to the through-drying fabric), according to the teachings of Chen et al. in commonly owned U.S. patent application Ser. No. 08/912,906, "Wet Resilient Webs and Disposable Articles Made Therewith," filed Aug.15, 1997. The tissue has a bulk of about 33 cc/g (density of 0.03 g/cc) and a wet:dry tensile strength ratio of 43%. Beneath the uncreped tissue layers was the 175 gsm densified airlaid web of the outer absorbent member (0.1 g/cc density) which had been previously cut out from the outer absorbent member.

Example 4 followed Example 3 except that three layers of the uncreped tissue were used in place of the two layers from Example 3 to create the upper layers of the central absorbent member above the 175 gsm airlaid lower layer. The three layers were calendered to provide the same thickness together as the two layers did in Example 3.

In Example 5 a 200-gsm layer of softwood fluff pulp (described in Table 1) with a diamond embossment thereon was placed above the 175 gsm densified airlaid material of the outer absorbent member to form the central absorbent member. No central longitudinal slit was provided in the upper layer of the central absorbent member. The fluff pulp was prepared by splitting a 400-gsm pad of fluff. The formerly interior portion of the 400 gsm appeared substantially uniform, while the opposing surface (formerly an exterior surface of the 400 gsm pad) showed the diamond embossing pattern clearly. The latter side was placed downward, toward the backsheet, in assembling the pad.

In Example 6 a maxipad was prepared with an unembossed 600 gsm fluff pulp pad (described in Table 1) as the absorbent material for both the outer absorbent member and the central absorbent member. The cut out portion from the central void (same dimensions as in previous Examples) was lined with polymeric film (the colored impervious wicking barrier of Table 1) having a width of about 5.5 cm instead of 4.7 cm as in previous Examples, and then replaced in the void, with the polymeric film defining a vertical wicking barrier between the central absorbent member and the surrounding outer absorbent member. In this case, the central absorbent member consisted essentially of the same material as the surrounding outer absorbent member.

In Example 7, a control maxi pad was produced using an unembossed 600 gsm fluff pulp mat with no wicking barrier and with no central void provided therein.

Testing of Examples 1–5 was done using insults of saline solution containing a small quantity of blue dye. In one group of tests, a 15 ml insult of the blue fluid were added to the center portion. In another group of tests, the insult was 7 ml. In both cases, some of the blue fluid escaped from the edges of the central strip in the control pad of Example 1, wetting the surrounding outer absorbent member. For both the 7 ml and 15 ml insult tests, the pads of the present invention held the fluid in the central absorbent member without substantial spread of the blue liquid into the surrounding outer absorbent member, thus achieving center-fill performance.

Testing with the maxipads of Example 6 and 7 by insulting blue saline solution into the center of the pad showed that the wicking barrier in Example 6 was successful in preventing fluid from migrating toward the longitudinal sides of the sides compared to Example 7.

Under light compression by hand (estimated at about 0.1 psi) of the wetted pads, the pads of the present invention also showed improved ability to retain their fluid in the central absorbent member compared to the control pad of Example 1.

Examples 8–10

Examples 8 to 10 were made according to Examples 3 to 5, respectively, except that the central absorbent member was inverted in each case. Thus, in Example 8, the upper layer of the central absorbent member was the cut-out portion of the 175-gsm densified airlaid web, while the lower two layers were the uncreped through-dried tissue layers, with the airlaid strip still isolated from the outer absorbent member by the vertical wicking barrier with its vertical component (the vertical wall between the members) and its horizontal component (the ledge resting on a portion of the body-side surface of the outer absorbent member). In Example 9, three layers of uncreped tissue were below the airlaid web in the central absorbent member. In Example 10, the central strip of densified airlaid web rested above a section of 200-gsm fluff pulp.

Examples 11–13

Examples 11 to 13 were made according to Examples 1, 2, and 4 above, respectively, with the exception that a dogbone-shaped 175-gsm densified airlaid web prior to cutting out a central void was provided with 5 equidistantly spaced apart parallel embossing lines running about 80% of the length of the pad, having a width of about 2 mm each. Further, the central absorbent member was not provided with the curved embossing lines of FIG. 21 or any other form of embossment, except for the embossments present in the cut-out central densified airlaid strip which was used to form part of the central absorbent member in each case. Thus, Example 11 is identical to Example 1 except for embossment in the lower layer (the underlying outer absorbent member) and lack of embossment in the upper layers (central absorbent member). Example 12 is likewise identical to Example 2 except for embossing differences. Example 13 has a central absorbent member with three unembossed layers of uncreped tissue superposed on a cut-out section of the 175-gsm densified airlaid web with longitudinal embossing lines therein.

Example 14

Example 14 is identical to Example 2 except that a clear polyethylene film of about 1 mil thickness was used to form the vertical wicking barrier instead of the rose film of Example 2.

Example 15

Example 15 is a maxipad with fluff pulp as the primary absorbent material made according to Example 6, with the exception that the central absorbent member comprises a strip of a dual-zoned web made according to the principles taught by Chen et al. in Ser. No. 08/997,287, "Dual-zoned Absorbent Webs," filed Dec. 22, 1997. Specifically, a 40 gsm web of uncreped through-air dried tissue made from bleached kraft eucalyptus fibers (Aracruz, Brazil) was textured on a three-dimensional Lindsay Wire T-116-1 through-drying fabric with about 15% rush transfer, resulting in a bulk of about 14 cc/g, largely due to the three-dimensional texture of the web. Kymene 557H wet strength agent (Hercules, Wilmington, Del.) was added at a level of about 7 kg/ton dry fiber. The uppermost portions of the dried web that had contacted the through-drying fabric (the wire-side) were coated with Dow Corning DAP® Silicone Auto/Marine Sealant applied at a total area-averaged level of 5 gsm (estimated to be about 12 gsm on the peaks that received the material). After curing, the coated side of the tissue had a soft, rubbery feel due to the rubbery silicone material being on the highest portions. Though the silicone is impervious and hydrophobic, the coated web is still hydrophilic and able to take liquid in readily due to the untreated lower portions of the web.

The dual-zoned web was provided with an array of spaced apart apertures, each about 0.5 cm apart from its nearest neighbor, each aperture having a diameter of about 0.5 mm. The apertures were stamped by hand into the web, with stamping occurring from the coated side toward the uncoated side. Based on tests with egg white solution as a menses simulant, the apertures were found to be helpful in transporting viscoelastic material through the dual-zoned web to the underlying absorbent material for an improved dry feel on the surface of the article.

A strip of the silicone-treated textured uncreped tissue web was cut to the same size as the central absorbent members of previous examples and placed over the cut-out section of 600 gsm fluff pulp within the central void lined with the wicking barrier (rose-colored impervious wicking barrier as in Table 1). The coated side of the treated web was facing up (toward the body side). To permit the treated dual-zoned web to serve as a cover material as well as an intake layer, a rounded rectangle 3.3 cm wide and 10.5 cm long was cut out of the spunbond web normally used as a topsheet, such that the rounded rectangular hole in the topsheet was centered over the dual-zoned web of the central absorbent member, thus providing direct access to permit the dual-zoned web to touch the body of the wearer and serve as a dry-feel cover material and intake material. The dual-zoned web cover materials of the aforementioned patent application of Chen et al. permit a cover to provide the dry feel of a hydrophobic plastic film while also providing intrinsic hydrophilicity and softness.

The resulting maxipad was thus composed of 600 gsm fluff pulp with a rose-colored wicking barrier surrounding a cut-out section of the fluff pulp, providing a vertical barrier and a visible horizontal ledge around the central absorbent member. The ledge and longitudinal sides of the dual-zoned web were covered by the spunbond topsheet, but most of the area of the dual-zoned web was exposed through the hole cut in the topsheet. Adhesive on the topsheet held the edges of the hole in place on the dual-zoned web.

Example 16

Example 16 was made according to Example 12 except that the central absorbent member was entirely replaced with about 3.3 grams of lose "nits" made of bleached kraft eucalyptus fibers which had been mechanically curled and dispersed to form small dense flocs about 1 mm in diameter. The nits were prepared by taking about 20 grams of dry eucalyptus pulp that had been curled in a Maule disperser, than moistening the pulp to a consistency of 20% and beating in a Hobart mixer for 1.5 hours to create dense nits. The moist nits were then spread out on a surface and air dried. The dry, loose nits were placed over the wicking barrier film inside the void of the outer absorbent member and covered with the topsheet, which served to hold them in place.

Example 17

Example 17 was made according to Example 2 except that the topsheet was pleated to provide longitudinal loops of cover material directly over the edge of the central absorbent member. The air-filled loops were heat sealed with an Impulse Sealer by American Electronics, designed for sealing plastic bags. The heat-sealed loops were thus rendered largely impervious and slightly glossy in appearance, though not uncomfortably stiff. The longitudinal loops raised about 0.4 cm from the surface of the absorbent article.

Example 18

Figure 22A:
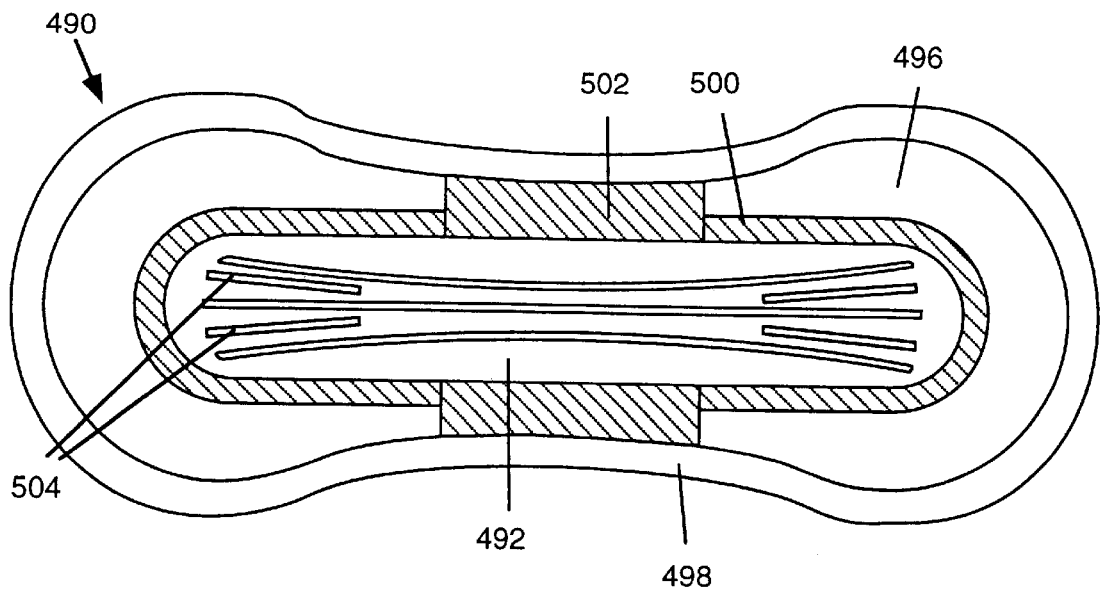
FIG. 22 depicts an absorbent article with two layers of film serving as the wicking barrier.
Figure 22B:
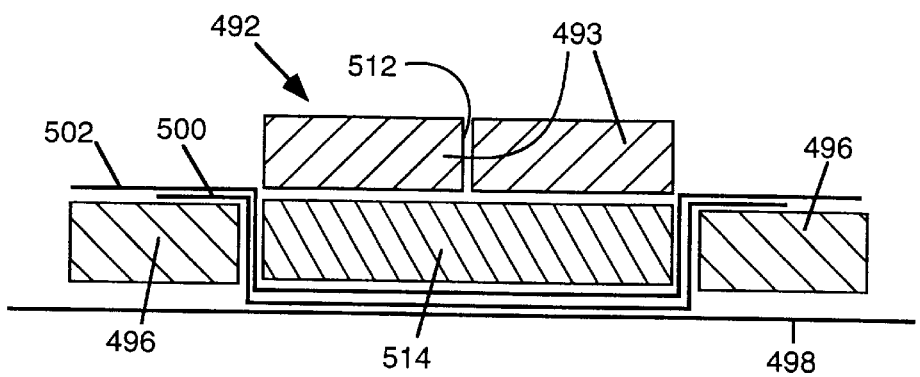

A pad was made according to Example 2 except that an additional rectangular section of barrier material was superposed over the rounded rectangular cut-out section of barrier material in Example 2 to ensure that a portion of the horizontal component of the wicking barrier extended to the longitudinal sides of the absorbent core. The resulting design is depicted in FIG. 22, where the top view is shown in FIG. 22A and the transverse cross-section (minus the topsheet) is shown in FIG. 22B. A strip of white impervious wicking barrier material 502 (as in Table 1), 100 mm in length and wide enough to extend from one longitudinal side of the absorbent core to the other, was placed over the rounded rectangular wicking barrier 500 lining the central void in the outer absorbent member 496 before inserting the densified airlaid layers that formed the central absorbent member 492. In the central absorbent member 492, the lower layer 514 was a 175 gsm densified airlaid web with a density of 0.1 g/cc (the same material used in the outer absorbent member 496, as in Table 1). The upper layer 493 was a densified airlaid web having a density of 0.14 gsm and basis weight of 250 gsm, further comprising a longitudinal slit 512 that was 100 mm in length through the longitudinal centerline. Both layers in the central absorbent member 492 were embossed with longitudinal embossing lines 504. An impervious backsheet 498 and a spunbond topsheet (not shown), both as described in Table 1, were used.

In this embodiment, the extended horizontal component of the upper ply 502 of the wicking barrier spanned the transverse width of the absorbent core in the crotch region, having a length of 100 mm.

Example 19

Figure 23:
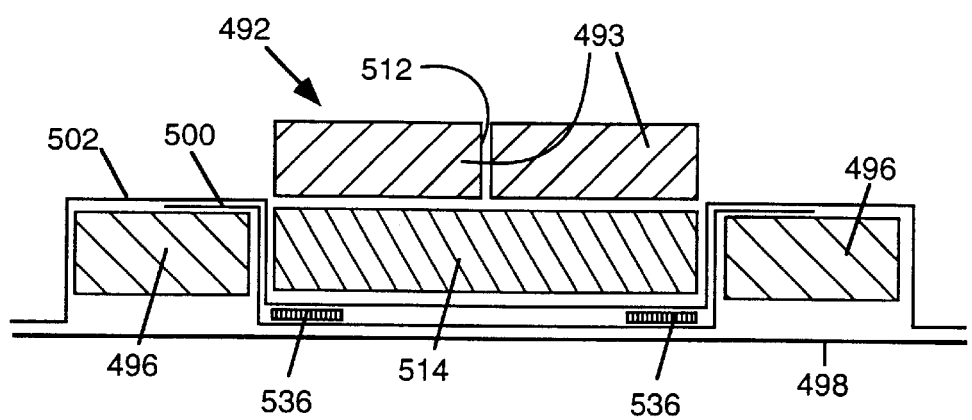
FIG. 23 depicts an absorbent article with two layers of film serving as the wicking barrier, wherein the outer absorbent member is largely encased in impervious material.

A cross-section (minus the topsheet) for Example 19 is shown in FIG. 23. Example 19 followed Example 18 except that the upper ply of wicking barrier material 502 in the crotch region was long enough to wrap the longitudinal sides of the article and make sealing contact with the backsheet 498. Thus, the outer absorbent member 496 is largely encased in impervious material (the backsheet 498 and the upper ply of wicking barrier material 502) such that it remains dry and able to provide a shaping function.

Additionally, two 10-cm long strips of two-sided adhesive tape 536 were used to join the lower ply 500 of wicking barrier material to the upper ply 502 in the crotch region, as shown in FIG. 23.

This embodiment was tested by menstruating adult users. Examination of the wetted pads showed excellent center fill performance and improved leakage reduction compared to other commercial products. It is believed that in addition to prevent wicking of fluid toward the longitudinal sides, the present design also helps direct flow toward the central absorbent member 492, preventing surface leakage or surface smearing. Further, it is believed that the discrete central absorbent member 492 and outer absorbent member 496 with a wicking barrier therebetween naturally promotes a W-shaped fold in the article when attached to the wearer's panties and compressed between the thighs of the user. The W-shape fold, which is also facilitated by the central slit 512 in the upper layer of the central absorbent member 492, provides an elevated central portion of the article to contact the wearer's body to directly receive menses and prevent flow along the user's body.

Example 20

Figure 24A:
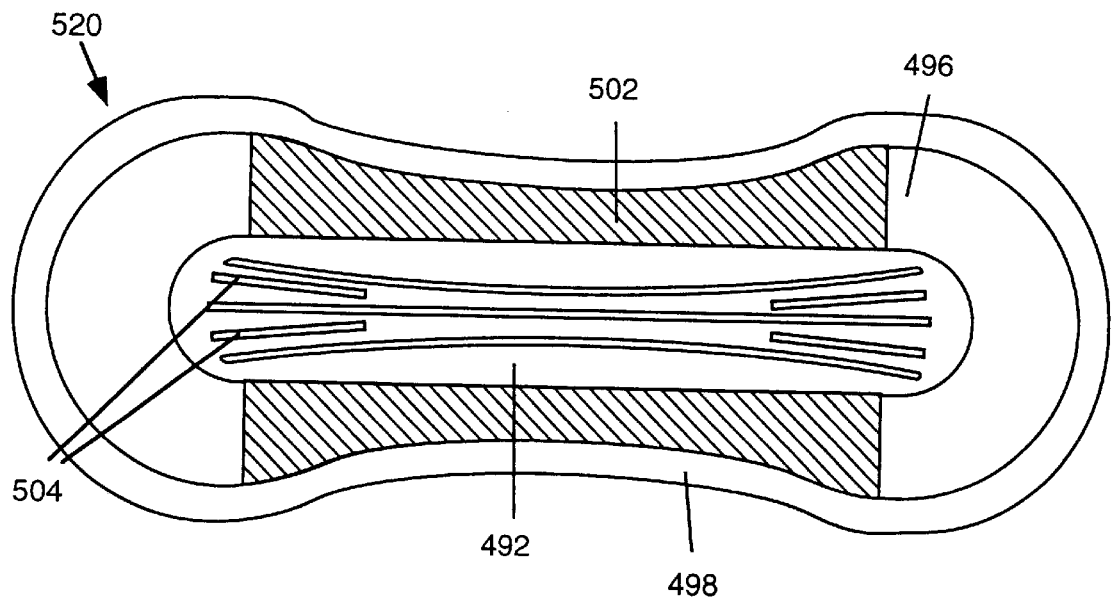
FIG. 24 depicts an absorbent article with a single wicking barrier extending to the longitudinal sides of the absorbent core in the crotch region.
Figure 24B:
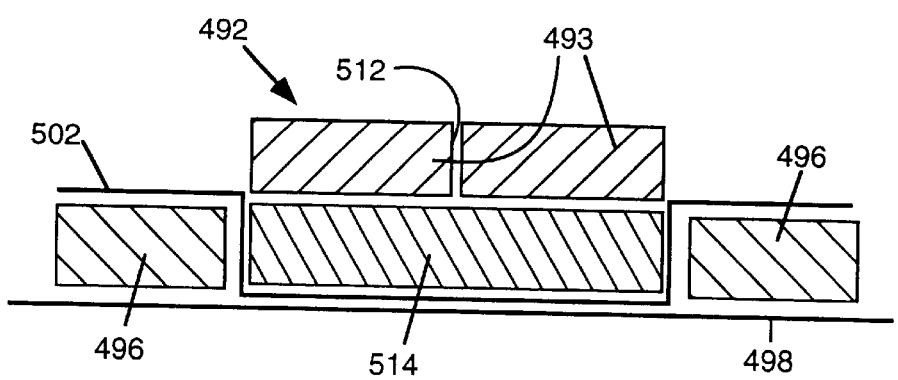

Example 20 is a hypothetical example depicted in FIG. 24, where a top view is shown in FIG. 24A and a transverse cross-section in FIG. 24B. This example follows the geometry of Example 18 and FIG. 22, with the exceptions that the lower layer of wicking barrier material 500 in FIG. 22 has been removed, and the longitudinal length of the crotch-section wicking barrier 502 was extended to about 160 mm.

Related embodiments are possible wherein the wicking barrier does not completely surround the central absorbent member, but is only present in or near the crotch region where leakage to the sides tends to be most problematic. Indeed, the outer absorbent member need not surround the central absorbent member everywhere, but may be present only near the transverse centerline or in the crotch region, where the outer absorbent member is largely separated from the central absorbent member by a wicking barrier.

Example 21

Example 21 is a feminine care maxipad that followed the geometry of FIG. 21, as described for Example 2, except that no embossing was performed and the horizontal component of the wicking barrier was extended to cover substantially all of the body-side surface of the outer absorbent member. Further, the absorbent material in both the central absorbent member and the outer absorbent member was 620 gsm fluff pulp. A white impervious wicking barrier of unembossed 1 mil polyethylene film was used. A central void in the outer absorbent member was formed by stamping a hole through the outer absorbent member. The cut-out fluff pulp was replaced after the hole was lined with the wicking barrier. No slit was made in the central absorbent member. This sample was tested with menstruating users and resulted in unexpected leakage, apparently because the central absorbent member did not come close to the body but deflected away from the body in use. It is believed that the better performance observed in other embodiments is due to various factors that promote a W-fold shape or elevate the central absorbent member toward the body. Such factors include slits in the central absorbent member, a raised central absorbent member relative to the outer absorbent member, and lower thickness of the absorbent members than was found with 620 gsm fluff pulp.

Example 22

Example 22 is a feminine care "ultra-thin" pad that followed the geometry of FIG. 24, except that the horizontal component of the wicking barrier was extended to cover substantially all of the body-side surface of the outer absorbent member. The upper layer 493 of the central absorbent member 492 was a densified airlaid web with a basis weight of 250 gsm and a density of 0.14 g/cc, with a 100-mm long central slit 512, while the lower layer 514 was a densified airlaid web with a basis weight of 175 gsm and a density of 0.1 g/cc, the same as the material used to form the outer absorbent member 496. The wicking barrier 502 was a white 1 mil polyethylene web. A central void in the outer absorbent member was formed by stamping a hole through the outer absorbent member. The cut-out densified airlaid web was replaced in the void after the hole was lined with the wicking barrier. This sample was tested with menstruating users and resulted in excellent center-fill performance and leakage prevention relative to other commercial products and relative to the control sample of Example 1.

Example 23

Example 23 followed that of Example 22 except the 228 gsm coform comprising 70% southern softwood and 30% polypropylene was used as the absorbent material for the outer absorbent member, the lower layer of the central absorbent member, and the slit upper layer of the central absorbent member.

Example 24

Figure 25A:
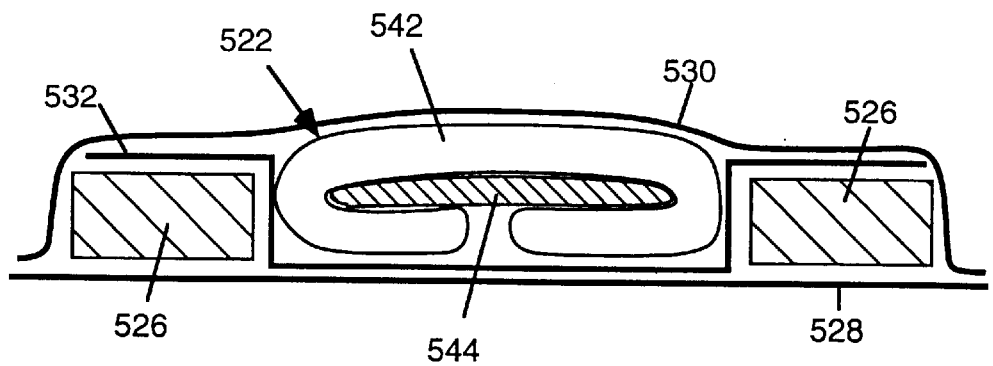
FIG. 25 depicts embodiments in which the central absorbent member comprises an absorbent layer wrapped around a second layer of absorbent material.
Figure 25B:
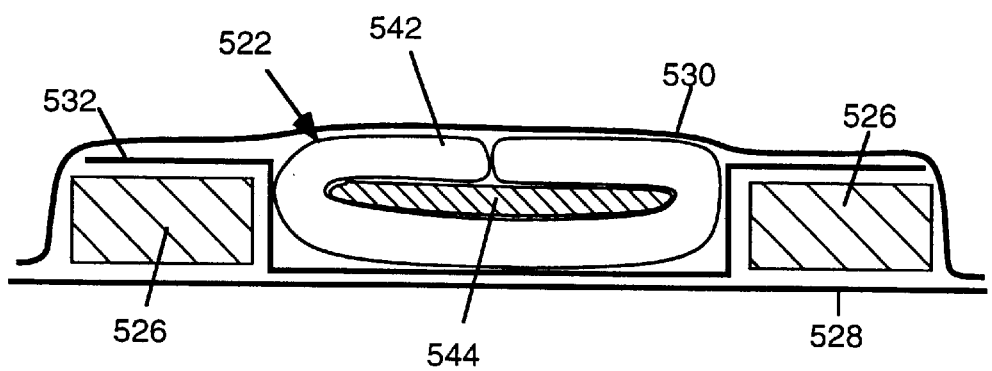

Example 24 is a hypothetical example depicted in two alternative forms in FIGS. 25A and 25B, showing a transverse cross-section of a sanitary napkin. Here a central absorbent member 522 comprises a first layer 542 folded around a second layer 544 in a C-fold configuration, with the C-fold being away from the body side in FIG. 25A and toward the body-side in FIG. 25B. The central absorbent member 522 is lined beneath by a wicking barrier 532 and above by a topsheet 530, which is attached to a backsheet 528 at the periphery of the absorbent article. The outer absorbent member 526 surrounds the central absorbent member 522. The second layer 544 of the central absorbent member can be a densified material with higher capillary pressure (smaller pore size) than the first layer 542, such that it preferentially absorbs fluids from the body. Exemplary materials for the second layer 544 include peat moss, a densified airlaid web, a regenerated cellulose sponge, coform, densified fluff pulp, one or more layers of wet laid paper or tissue, optionally combined with shaping elements such that the central absorbent member folds along the longitudinal centerline in use to rise toward the body. Thus, the second layer 544 may be slit or scored, for example, to enhance folding along the longitudinal centerline in use. The first layer 542 may be fluff, an airlaid web, coform, wet laid tissue, or a nonwoven surge layer preferably treated to be hydrophilic.

Example 25

Example 25 was made according to Example 2, only the central absorbent member and outer absorbent member were made of Coosa River 1654 softwood pulp in fluff pulp form having a basis weight of 250 gsm and densified to 0.14 g/cc. Two layers of the densified fluff pulp were used to form the central absorbent member, and were provided with a central longitudinal slit 10 comprises in length. The central absorbent member, being thicker and stiffer than the outer absorbent member by virtue of having twice as much material, appeared to readily yield a useful w-fold geometry when compressed from the sides.

Example 26

Example 26 followed Example 25 except that the two layers of the central absorbent member were embossed together with longitudinal flare lines, similar to the lines shown in FIG. 22A.

Example 27

Example 27 followed Example 26 except that a layer of 20-gsm softwood creped tissue comprising wet strength agents was placed underneath each layer of fluff pulp in the central absorbent member, thus helping to maintain separation of the two layers in use. Thus, when the central absorbent member is bunched together by the legs of the user in use, the tissue layers help prevent interlocking or entanglement of fibers in the two adjacent fluff pulp payers and thus help prevent wadding of the central absorbent member. The central absorbent member thus becomes more resilient or capable of resisting collapse and maintaining its form. Desirably, tissue layers separating adjacent absorbent layers in the central absorbent member will have a wet strength to dry strength ratio of at least 0.1.

Example 28

Figure 26:
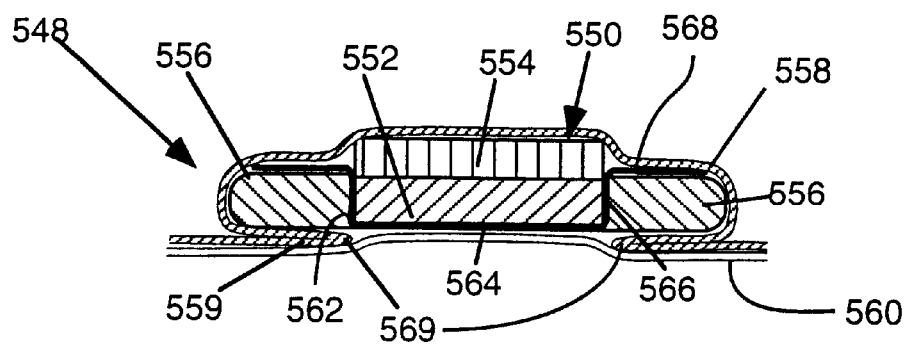
FIG. 26 depicts an absorbent article in which the topsheet wraps the edges and undersides of the outer absorbent member to permit the outer edges of the absorbent core to flex away from the backsheet.

Example 28 was made according to article 548 shown in FIG. 26, following the structure and materials given in Example 2. The central absorbent member 550 comprised a top layer 554 of 250 gsm densified airlaid web at a density of 0.1 g/cc, and a bottom layer 552 comprising a layer of 175-gsm densified airlaid web at a density of 0.14 g/cc. The two layers of the central absorbent member 550 were provided with a longitudinal slit to encourage a W-fold shape when compressed laterally by the legs of the user. A single layer of 175-gsm densified airlaid web at a density of 0.14 g/cc was used to form the outer absorbent member 556. A clear polymer film was used to form the wicking barrier 562, comprising a vertical component 566, a horizontal component 568 on the body side surface of the outer absorbent member 556, and an underlying portion 564 beneath the central absorbent member 550. The wicking barrier 562 was cut when the outer perimeter of the outer absorbent member 556 was cut to have approximately the same surface area and shape, when viewed from above. A distinct feature of the embodiment in Example 28 is the configuration of the topsheet 558, which wraps the outer edges of the outer absorbent member 556 and runs along the bottom thereof before folding back on itself at a hinge point 559, where the topsheet 558 is doubled, one layer in adhesive contact with the backsheet 560 and the other layer in contact with the lower side of the outer absorbent member 556. This configuration allows the outer absorbent member 556, which can be relatively thinner than FIG. 26 indicates (not being drawn to scale), to be able to serve as a barrier, cuff, or flap, which can rise upward toward the body or into the fold between the crotch and the user's legs, independently of the position of the backsheet 560. For example, the backsheet 560 may be further attached to wings or tabs (not shown) which wrap around the edges of the user's panties, folding away from the body, yet the hinged structure created with the topsheet 558 wrapping around the outer absorbent member 556 creates an added level of flexibility in the article 548 to permit the outer absorbent member 556 to remain close to the body.

The wicking barrier 562 in this embodiment does not wrap the outer absorbent member 556. Thus, the outer longitudinal sides and bottom side of the outer absorbent member 556 can absorb any fluid that may contact the topsheet 558 in those regions. Thus, if a gush of fluid bypasses the central absorbent member 550 and flows toward the longitudinal sides of the article 548, it can be adsorbed by the surfaces of the outer absorbent member that are not covered with the wicking barrier 562. Particularly when the article 548 is compressed from the sides and the article assumes a W-fold shape, the surfaces of the outer absorbent member 556 that are not covered by the wicking barrier 562 can serve to absorb fluid in unusual circumstances that might otherwise leak or flow past the edges of the article 548. But under normal conditions of use, fluid absorption into the central absorbent member 550 with shielding from the outer absorbent member 556 by means of the wicking barrier 562 should be adequate for good center fill performance and leakage control.

The backsheet 560 was adhesively attached to the underlying portion 564 of the wicking barrier 562 beneath the central absorbent member 550.

Example 29

Figure 27:
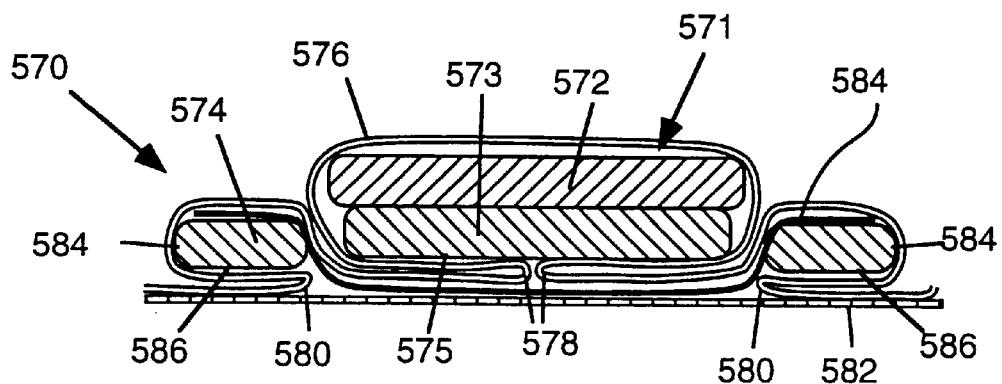
FIG. 27 depicts an embodiment similar to FIG. 26 in which the topsheet further wraps the edges and underside of the central absorbent member to permit its edges to flex away from the backsheet.

Example 29 is depicted in FIG. 27 and was made according to Example 27, except that the topsheet 576 of article 570 also wrapped around the edges and lower surface 575 of the central absorbent member 571, approaching the longitudinal centerline where the topsheet material 576 then folded back upon itself at hinge points 578 before extending toward the outer absorbent member 574. Thus, the central absorbent member 571, comprising a first layer 572 and a second layer 573 of densified airlaid web material, could fold away from the central restraints formed by the adhesive attachment to hinge points 578 such that the longitudinal sides of the central absorbent member 571 could move upward toward the body in the shape of a V. As in Example 27, a wicking barrier 584 prevented wicking of fluid from the central absorbent member 571 to the outer absorbent member 574. The topsheet 576 rose from underneath the central absorbent member 571, following the wicking barrier 584, to cover the outer absorbent member 574. The topsheet 576 further wrapped the outer longitudinal edges 584 and underside 586 of the outer absorbent member 574, contacting the backsheet 582 at hinge points 580 where the topsheet folded back upon itself to extend to the outer edges of backsheet 582, to which the topsheet 576 was adhesively attached.

In this embodiment, the outer edges of both the central absorbent member 571 and the outer absorbent member 574 were free to move up toward the body independently of the position of the backsheet 582, thus providing more flexibility, more opportunities for body conformability, especially if wings or tabs were affixed (not shown), and also providing additional surfaces not covered with wicking barrier material 584 for absorbing gushes or fluid that might not effectively reach the central absorbent member 571.

It is envisioned that many related embodiments could be made with multiple zones of absorbent material wrapped with the topsheet or other porous material such as tissue to permit the outer edges of the absorbent zones to deflect upward, away from the backsheet, thus providing flap-like or cuff-like structures formed from absorbent material, yet with the wicking barrier defining central and outer absorbent members and promoting central fill of the article. The flap-like structures, nevertheless, can serve to prevent leakage during gushes or fluid insults and can provide additional surface area for absorption of fluid.

Gaps between the central absorbent member and the outer absorbent member in such embodiments may be created to provide open channels for flow into the space between the members. Such gaps can be created by making the outer longitudinal sides of the central absorbent member to have a wavy shape, while the inner sides of the outer absorbent member could be relatively straight, thus providing imperfect fit with resulting periodic gaps or openings, desirably on the order of 0.1 to 2 mm. Either or both edges could be made irregular to provide occasional openings or gaps between the members, such that even when the article is lying flat, not in a W-folded shape, fluid could still reach the underside of the central absorbent member.

Embossments along the longitudinal centerline of the central absorbent member 571 can be helpful in causing the outer edges of the central absorbent member 571 to naturally deflect upward toward the body.

Example 30

Example 30 was made according to Example 29 as shown in FIG. 27 except that the topsheet did not wrap the underside of the outer absorbent member 574, but directly contacted the backsheet 582 after descending down the outer longitudinal sides of the outer absorbent member 574, as in FIG. 3.

Example 31

Figure 28:
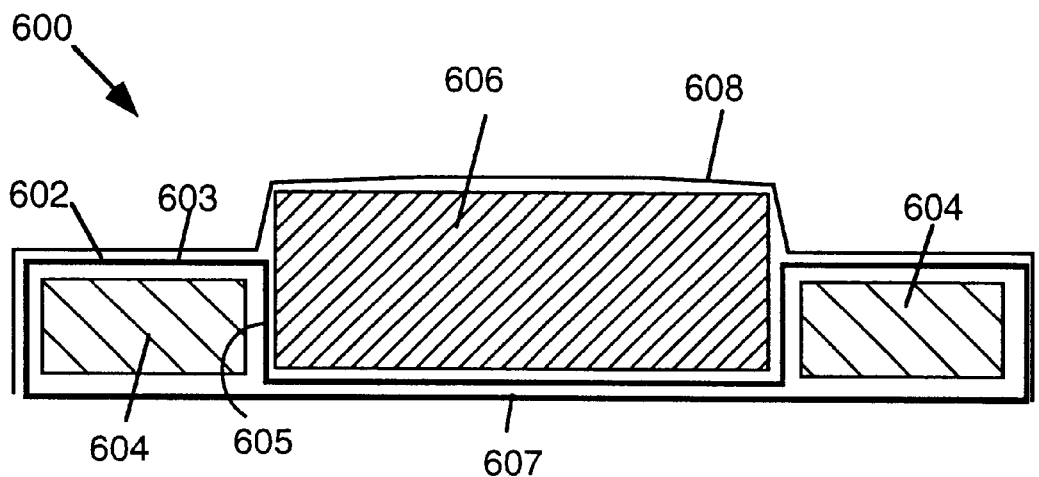
FIG. 28 depicts a cross-section of an absorbent article wherein the wicking barrier wraps around the outer absorbent member and runs along the garment side of the article, serving as a backsheet.

Example 31, as depicted in FIG. 28, is a hypothetical example of an article 600 according to the present invention wherein the wicking barrier 602 also serves as a backsheet, or visa versa, because a sheet of polymeric material covers the garment side of the article, providing a backsheet component 607, then wraps around the longitudinal sides and body side of the outer absorbent members 604, serving the function of a horizontal component 603 in the wicking barrier 602, and further penetrates or descends into the absorbent core (between the outer absorbent members 604 and the central absorbent member 606) to provide a vertical component 605 of the wicking barrier 602. Desirably, the wicking barrier 602 also passes beneath the central absorbent member 606, as shown. The topsheet 608 can be attached to the wicking barrier at the longitudinal sides of the article. Obviously, the topsheet should be more permeable and wettable than the backsheet or wicking barrier.

In FIG. 28 and other figures herein, the garment side of the absorbent core is generally depicted as planar with any nonuniformity in thickness in the members of the absorbent core resulting in height variations on the body side surface of the article. However, for some embodiments, it is possible to assemble the components to maintain a more planar body side surface with thickness variations resulting in height variations or contours on the garment side of the article. Such configurations may be considered in optimizing body fit and the geometrical response of the article when worn.

Example 32

Figure 29:
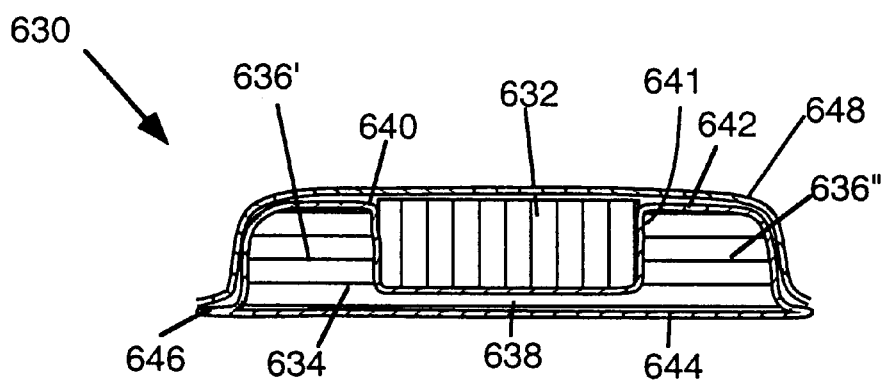
FIG. 29 depicts a cross-section of an absorbent article having a unitary shaping member surrounding a central absorbent member.

Example 32, as depicted in FIG. 29, is a hypothetical example of an article 630 according to the present invention comprising a topsheet 648, a unitary shaping member 634 comprising an outer shaping member 636 with a first portion 636' and a second portion 636" and a relatively thinner bridging portion 638 joining the first portion 636' and second portion 636" of the outer shaping member. Above the bridging portion 638 is a void or depression defined within the shaping member 634 which receives the central absorbent member 632, which may be provided with multiple slits and may comprise multiple layers (not shown). The body-side surface of the unitary shaping member 634 is provided with a substantially impervious or low permeability wicking barrier 640, which may be integral with the unitary shaping member 634, such as the outer skin on a shaped foamed article or the surface layer of a closed-cell foam, or a layer of thermoplastic film which has been adhered onto the surface of the shaping member 634. The wicking barrier 640 comprises a vertical component 641 and a horizontal component 642, which serve to prevent fluid wicking from the central absorbent member 632 and serve to direct fluid toward the central absorbent member 632. In one embodiment, no backsheet is necessary, or, as shown, an outer backsheet 644, desirably a liquid impervious layer, may be provided by the outer surface of the shaping member 634, which surface can be the skin on a foam, a polymeric coating, an adjoining film, a section of topsheet material wrapped around the article 630, or a film adhered to the shaping member 634.

Example 33

Figure 30:
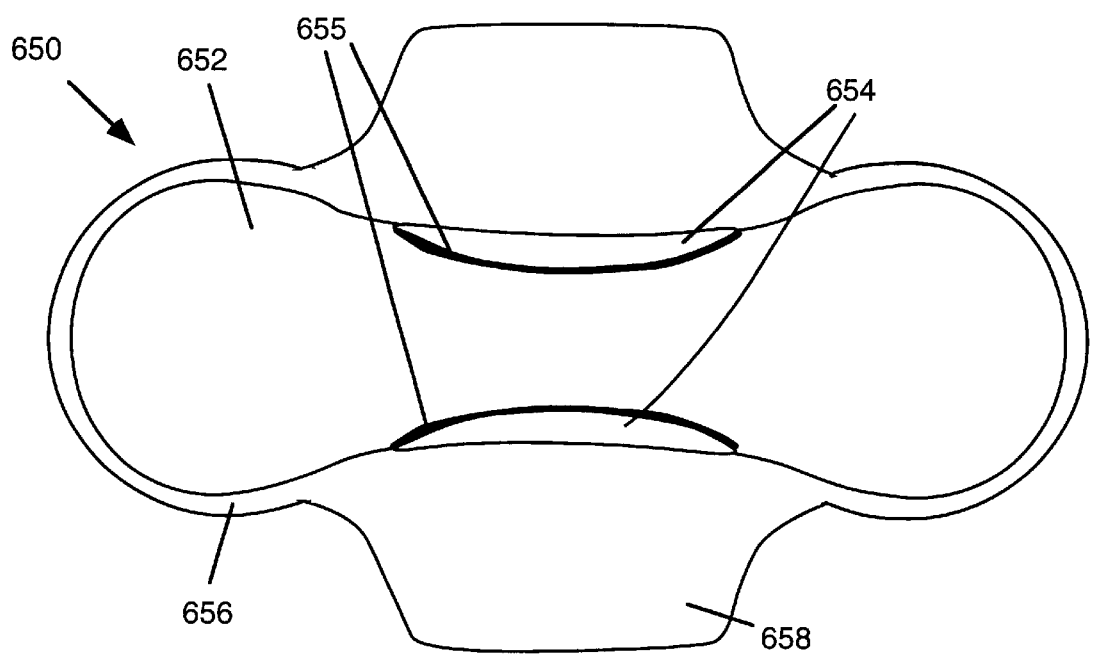
FIG. 30 depicts a commercial maxipad.

Example 33 was made using a commercially available maxipad, the ALWAYS® Maxi with Wings with a DRI-WEAVE™ apertured film cover, manufactured by Procter and Gamble (Cincinnati, Ohio) and taken from a package of 20. This product also features "side channels" which are crescent-shaped, highly densified regions along the longitudinal sides in the crotch region joined to the central high bulk, high thickness fluff pad that extends across the longitudinal length of the article. According to the package, the product was made under one of more of the following U.S. Pat. Nos. 4,342,314 and 4,463,045, previously incorporated by reference, and U.S. Pat. Nos. 4,556,146; 4,573,986; 4,589,876; 4,687,478; and 5,267,992, all of which are herein incorporated by reference in their entireties. FIG. 30 depicts the original pad 650 as purchased, showing a central high-bulk fluff pad region 652, densified outer zones 654 having a lower basis weight than the central region 652, with highly densified embossment lines 655 joining the central region 652 to the densified outer zone 654. The topsheet (not shown) joins the backsheet to form an outer rim 656, which is also attached to wings 658.

Figure 31:
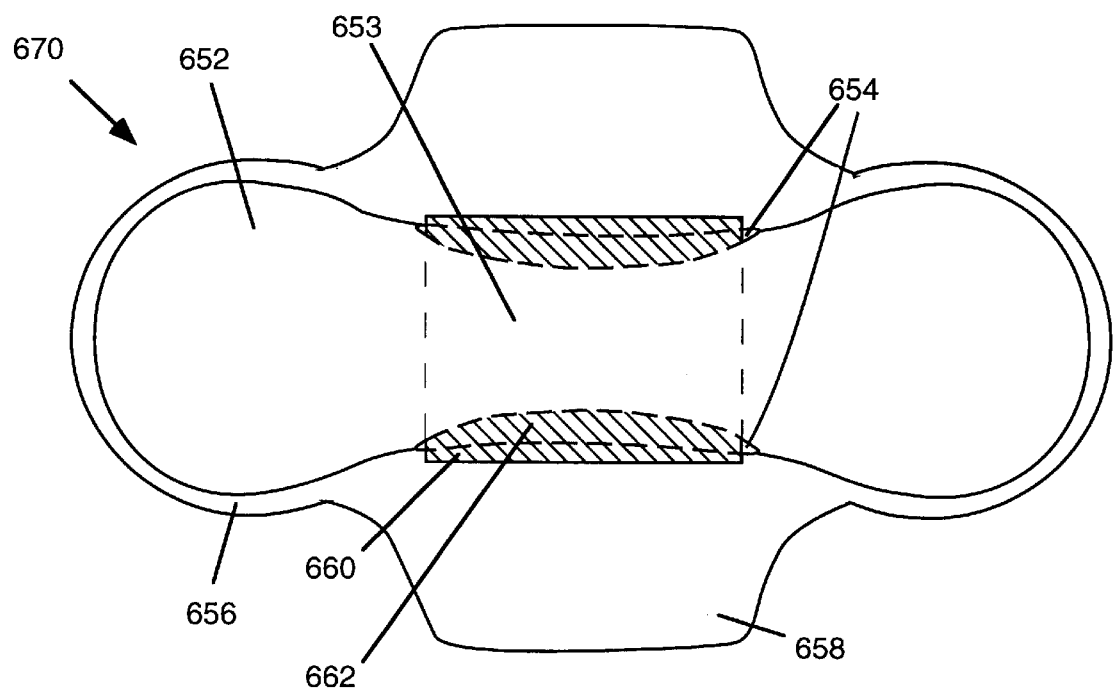
FIG. 31 depicts the modified maxipad of FIG. 30 after a wicking barrier has been added according to the present invention.

To convert the commercial article into a pad according to the present invention, the apertured film topsheet was slit near the outer perimeter of the wings 658 of the article, and by hand the densified outer zones 654 were separated from the central high-bulk region 652 by tearing along the embossment lines 655. Then a 20 gsm 1-mil pink poly film with a width of 5 cm was pulled into the slit and placed under the central high-bulk region 652 such that it covered the top surfaces of both of the densified outer zones 654 but went completely beneath the central high-bulk region 652 in the crotch region. The poly film was trimmed to just slightly extend past the outer perimeter of the densified outer zones 654, as depicted in FIG. 31, which follows the numbering scheme of FIG. 30 but shows a wicking barrier 660 comprising the poly film resting on the body-side surface 662 of the densified outer zones 654. In this embodiment, the densified outer zones 654 now serve collectively as the outer absorbent member having first and second portions with a void therebetween which has received a central absorbent member 653 comprising the central high-bulk region 652. The wicking barrier 660 has a horizontal component 662 on the outer absorbent member 654 and spans a vertical distance of about 5 mm from the top of the densified outer zones 654 to the backsheet (not shown) beneath the central high-bulk region 652 in the crotch region.

This modification of a commercial product, according to the present invention, can effectively reduce leaking to occur as fluid is wicked or otherwise transported from the high-bulk region 652 to the densified outer zones 654, and can reduce bending stiffness and enhance the folding geometry of the article when worn. Similar modifications may be made with other commercial articles, such as pantiliners.

Example 34

Figure 32:
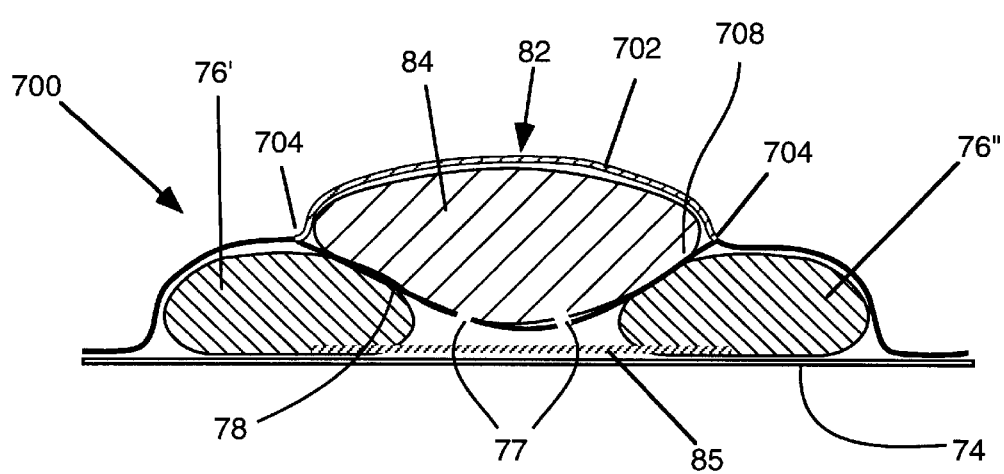
FIG. 32 depicts a cross-section of a sanitary napkin along the transverse centerline adapted generally following the embodiment depicted in FIG. 4B.

Example 34 is a hypothetical example depicted in FIG. 32, which shows a cross-section of a sanitary napkin 700 along the transverse centerline adapted generally following the embodiment depicted in FIG. 4B. The same numbering scheme as in FIG. 4B is used, except for modified elements.

In this embodiment, an abbreviated topsheet 702 extends primarily over the central absorbent member 82 but not completely over the outer absorbent member 76. Instead, the topsheet 702 is attached to an extended wicking barrier 708 which spans the underside of the central absorbent member 82 and wraps around the body-side surfaces of the outer absorbent member 76, which has a first portion 76' and a second portion 76". The extended wicking barrier 708 extends past the outer absorbent member 76 and joins to the backsheet 74. The wicking barrier 708 is also attached to the topsheet 702 at junctures 704. Thus, while the topsheet 708 is not directly attached to the backsheet 74, it can be considered to be indirectly attached to the backsheet 74 by means of a portion of the wicking barrier 708 serving as a joining element.

The abbreviated topsheet 702 permits fluid to readily enter the central absorbent member 84, while the wicking barrier 708 on the exposed surfaces of the outer absorbent member 76 will resist fluid intake and, more importantly, resist fluid transfer from the central absorbent member 82 to the outer absorbent member 76. Fluid can still pass from the absorbent material 84 of the central absorbent member 82 by means of a tortuous pathway comprising apertures or openings 77 in the wicking barrier 708 and an absorbent strip of material 85 that helps provide fluid communication between the region near the apertures 77 and the outer absorbent member 76.

Of course, one could define the combination of the abbreviated topsheet 702 and the portions of the wicking barrier 708 on the exposed body-side surfaces of the outer absorbent member 76 as the topsheet, which would then be a composite topsheet attached to a wicking barrier having a vertical component and a horizontal component (the ledge just outside the central absorbent member 82).

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent article having a longitudinal direction, a transverse direction, a vertical direction substantially normal to both the longitudinal and traverse directions, a pair of longitudinal ends, and a body side, the absorbent article comprising:
    a) an absorbent core having a body side surface, the absorbent core comprising an outer absorbent member having a body side surface and a central absorbent member, the outer absorbent member having a central void open toward the body side of the absorbent article, the central absorbent member having an average thickness, the central absorbent member disposed over and extending into the central void; and
    b) a wicking barrier disposed between the outer absorbent member and the central absorbent member, the wicking barrier having a vertical component and a horizontal component, the vertical component spanning a vertical distance between the outer absorbent member and the central absorbent member of at least about 20 percent of the average thickness of the central absorbent member, and the horizontal component spanning a horizontal distance on the body side surface of the absorbent core and covering at least a portion of the body side surface of the outer absorbent member.

2. The absorbent article of claim 1 further comprising a backsheet attached to the absorbent core.

3. The absorbent article of claim 2 further comprising a topsheet disposed over the absorbent core and attached to the backsheet.

4. The absorbent article of claim 1 wherein the central void vertically extends completely through the outer absorbent member.

5. The absorbent article of claim 4 wherein the central void extends longitudinally between the pair of longitudinal ends of the absorbent article and divides the outer absorbent member into two noncontiguous sections.

6. The absorbent article of claim 1 wherein the central void has a width and the central absorbent member has a width less than or equal to the width of the central void.

7. The absorbent article of claim 1 wherein the central absorbent member comprises at least about 50 percent papermaking fibers by weight.

8. The absorbent article of claim 1 wherein the wicking barrier is a liquid impervious material.

9. The absorbent article of claim 8 wherein the liquid impervious material is selected from a polymeric film, a nonwoven web, a flexible foam, a silicone layer, a tissue treated with a hydrophobic material and a spunbond web.

10. The absorbent article of claim 1 wherein the wicking barrier is a polymeric web that lines the central void beneath the central absorbent member.

11. The absorbent article of claim 1 wherein the vertical component of the wicking barrier spans a vertical distance between the central absorbent member and the outer absorbent member of at least about 50 percent of the average thickness of the central absorbent member.

12. The absorbent article of claim 1 wherein the vertical component of the wicking barrier spans a vertical distance between the central absorbent member and the outer absorbent member of at least about 70 percent of the average thickness of the central absorbent member.

13. The absorbent article of claim 1 wherein the vertical component of the wicking barrier spans a vertical distance between the central absorbent member and the outer absorbent member substantially equal to the average thickness of the central absorbent member.

14. The absorbent article of claim 1 wherein the horizontal component of the wicking barrier spans a horizontal distance of at least about 1 mm.

15. The absorbent article of claim 1 wherein the central absorbent member has a body side surface and wherein the horizontal component of the wicking barrier spans less than the entire body side surface of the central absorbent member.

16. An absorbent article having a longitudinal direction, a transverse direction, a vertical direction substantially normal to both the longitudinal and transverse directions, a pair of longitudinal ends, and a body side, the absorbent article comprising:
    a) an absorbent core having a body side surface, the absorbent core comprising an outer absorbent member and a central absorbent member having a body side surface and a garment side surface opposite the body side surface, the outer absorbent member having a central void, the central void having a depth, the central void open toward the body side of the absorbent article, the central absorbent member disposed over and extending into the central void; and b) a wicking barrier disposed between the outer absorbent member and the central absorbent member and a portion of the wicking barrier disposed on the garment side surface of the central absorbent member, the wicking barrier having a vertical component and a horizontal component, the vertical component comprising spanning a vertical distance between the outer absorbent member and the central absorbent member of at least about 50 percent of the depth of the central void, and the horizontal component spanning a horizontal distance on the body side surface of the absorbent core.

17. The absorbent article of claim 16 further comprising a backsheet attached to the absorbent core.

18. The absorbent article of claim 17 further comprising a topsheet disposed over the absorbent core and attached to the backsheet.

19. The absorbent article of claim 16 wherein the central void vertically extends completely through the outer absorbent member.

20. The absorbent article of claim 19 wherein the central void extends longitudinally between the pair of longitudinal edges of the absorbent article and divides the outer absorbent member into two noncontiguous sections.

21. The absorbent article of claim 16 wherein the central void has a width and the central absorbent member has a width less than or equal to the width of the central void.

22. The absorbent article of claim 16 wherein the vertical component of the wicking barrier substantially spans the entire depth of the central void.

23. The absorbent article of claim 16 wherein the central absorbent member comprises at least about 50 percent papermaking fibers by weight.

24. The absorbent article of claim 16 wherein the wicking barrier is a liquid impervious material.

25. The absorbent article of claim 24 wherein the liquid impervious material is selected from a polymeric film, a nonwoven web, a flexible foam, a silicone layer, a tissue treated with a hydrophobic material, and a spunbond web.

26. The absorbent article of claim 16 wherein the wicking barrier is a polymeric web which lines the central void beneath the central absorbent member.

27. The absorbent article of claim 16 wherein the horizontal component of the wicking barrier spans a horizontal distance of at least about 1 mm.

28. The absorbent article of claim 16 wherein the central absorbent member has a body side surface and wherein the horizontal component of the wicking barrier spans less than the entire body side surface of the central absorbent member.

29. An absorbent article having a longitudinal direction, a transverse direction, a transverse axis, a vertical direction substantially normal to both the longitudinal and transverse directions, a pair of longitudinal ends, and a body side, the absorbent article comprising:

a) an absorbent core having a body side surface, the absorbent core comprising an outer absorbent member and a central absorbent member, the outer absorbent member having a body side surface and a central void open toward the body side of the absorbent article, the central absorbent member disposed over and extending into the central void; and b) a wicking barrier disposed between the outer absorbent member and the central absorbent member, the wicking barrier having a vertical component and a horizontal component, the vertical component spanning a vertical distance between the outer absorbent member and the central absorbent member, the horizontal component covering at least about 30 percent of the body side surface of the outer absorbent member along the transverse axis.

30. The absorbent article of claim 29 further comprising a backsheet attached to the absorbent core.

31. The absorbent article of claim 30 further comprising a topsheet disposed over the absorbent core and attached to the backsheet.

32. The absorbent article of claim 29 wherein the central void vertically extends completely through the outer absorbent member.

33. The absorbent article of claim 32 wherein the central void extends longitudinally between the pair of longitudinal ends of the absorbent article and divides the outer absorbent member into two noncontiguous sections.

34. The absorbent article of claim 29 wherein the central void has a width and the central absorbent member has a width equal to or less than the width of the central void.

35. The absorbent article of claim 29 wherein the central void has a depth and the vertical component of the wicking barrier spans a vertical distance of at least about 50 percent of the depth of the central void.

36. The absorbent article of claim 29 wherein the central void has a depth and the vertical component of the wicking barrier is substantially equal to the depth of the central void.

37. The absorbent article of claim 29 wherein the central absorbent member comprises at least about 50 percent papermaking fibers by weight.

38. The absorbent article of claim 29 wherein the wicking barrier is a liquid impervious material.

39. The absorbent article of claim 38 wherein the liquid impervious material is selected from a polymeric film, a nonwoven web, a flexible foam, a silicon, layer, a tissue treated with a hydrophobic material, and a spunbond web.

40. The absorbent article of claim 29 wherein the wicking barrier is a polymeric web that lines the central void beneath central absorbent member.

41. The absorbent article of claim 29 wherein the horizontal component of the wicking barrier covers at least about 50 percent of the body side surface of the outer absorbent member along the transverse axis.

42. The absorbent article of claim 29 wherein the horizontal component of the wicking barrier covers at least about 80 percent of the body side surface of the outer absorbent member along the transverse axis.

43. The absorbent article of claim 29 wherein the horizontal component of the wicking barrier covers about 100 percent of the body side surface of the outer absorbent member along the transverse axis.

44. The absorbent article of claim 29 wherein the central absorbent member has a body side surface and wherein the horizontal component of the wicking barrier covers less than the entire body side surface of the central absorbent member.

45. An absorbent article having a transverse axis, a longitudinal direction, a transverse direction, a vertical direction substantially normal to both the longitudinal and transverse directions, a pair of longitudinal ends, and a body side, the absorbent article comprising;

a) an absorbent core having a body side, the absorbent core including an outer absorbent member and a central absorbent member, the outer absorbent member having a body side surface and a central void open to the body side of the absorbent article, the central absorbent member having an average thickness, the central absorbent member disposed over and extending into the central void; and b) a liquid impervious single ply film barrier disposed between the outer absorbent member and the central absorbent member, the barrier having a vertical component and a horizontal component, the vertical component spanning a vertical distance of between the outer absorbent member and the central absorbent member of at least about 20 percent of the average thickness of the central member, and the horizontal component covering at least about 30 percent of the body side surface of the outer absorbent member along the transverse axis.

46. The absorbent article of claim 43 further comprising a backsheet attached to the absorbent core.

47. The absorbent article of claim 46 further comprising a topsheet disposed over the absorbent core and attached to the backsheet.

48. The absorbent article of claim 43 wherein the central void vertically extends completely through the outer absorbent member.

49. The absorbent article of claim 48 wherein the central void extends longitudinally between the pair of longitudinal ends of the absorbent article and divides the outer absorbent member into two noncontiguous sections.

50. The absorbent article of claim 43 wherein the central absorbent member comprises at least about 50 percent papermaking fibers by weight.

51. The absorbent article of claim 43 wherein the wicking barrier lines the central void beneath the central absorbent member.

52. The absorbent article of claim 45 wherein the vertical component of the wicking barrier spans a vertical distance between the outer absorbent member and the central absorbent member of at least about 50 percent of the average thickness of the central absorbent member.

53. The absorbent article of claim 45 wherein the vertical component of the wicking barrier spans a vertical distance between the outer absorbent member and the central absorbent member of at least about 70 percent of the average thickness of the central absorbent member.

54. The absorbent article of claim 45 wherein the vertical component of the wicking barrier spans a vertical distance between the outer absorbent member and the central absorbent member that is substantially equal to the average thickness of the central absorbent member.

55. The absorbent article of claim 45 wherein the horizontal component of the wicking barrier covers at least about 50 percent of the body side surface of the outer absorbent member along the transverse axis.

56. The absorbent article of claim 45 wherein the horizontal component of the wicking barrier covers at least about 80 percent of the body side surface of the outer absorbent member along the transverse axis.

57. The absorbent article of claim 45 wherein the horizontal component of the wicking barrier covers about 100 percent of the body side surface of the outer absorbent member along the transverse axis.

* * * * *